(12) United States Patent
Kelley et al.

(10) Patent No.: US 11,466,087 B2
(45) Date of Patent: Oct. 11, 2022

(54) ANTI-CLL-1 ANTIBODIES AND METHODS OF USE

(71) Applicant: Genentech, Inc., South San Francisco, CA (US)

(72) Inventors: Robert F. Kelley, Petaluma, CA (US); Steven R. Leong, Berkeley, CA (US); Wei-Ching Liang, Foster City, CA (US); Mary Mathieu, San Francisco, CA (US); Andrew G. Polson, San Francisco, CA (US); Bing Zheng, Mountain View, CA (US); Xiaocheng Chen, Foster City, CA (US); Cecilia Pui Chi Chiu, San Carlos, CA (US); Mark S. Dennis, San Carlos, CA (US); Allen Ebens, San Carlos, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 368 days.

(21) Appl. No.: 16/658,706

(22) Filed: Oct. 21, 2019

(65) Prior Publication Data
US 2020/0148774 A1 May 14, 2020

Related U.S. Application Data

(62) Division of application No. 15/182,327, filed on Jun. 14, 2016, now Pat. No. 10,501,545.

(60) Provisional application No. 62/307,003, filed on Mar. 11, 2016, provisional application No. 62/180,376, filed on Jun. 16, 2015.

(51) Int. Cl.
| | | |
|---|---|---|
| A61K 39/395 | (2006.01) |
| C07K 16/28 | (2006.01) |
| C07K 16/30 | (2006.01) |
| A61K 45/06 | (2006.01) |
| A61K 39/00 | (2006.01) |

(52) U.S. Cl.
CPC ...... *C07K 16/2851* (2013.01); *A61K 39/3955* (2013.01); *A61K 45/06* (2013.01); *C07K 16/2803* (2013.01); *C07K 16/2809* (2013.01); *C07K 16/2827* (2013.01); *C07K 16/3061* (2013.01); *A61K 2039/505* (2013.01); *A61K 2039/507* (2013.01); *A61K 2039/57* (2013.01); *C07K 2317/14* (2013.01); *C07K 2317/24* (2013.01); *C07K 2317/31* (2013.01); *C07K 2317/33* (2013.01); *C07K 2317/34* (2013.01); *C07K 2317/40* (2013.01); *C07K 2317/41* (2013.01); *C07K 2317/52* (2013.01); *C07K 2317/526* (2013.01); *C07K 2317/55* (2013.01); *C07K 2317/56* (2013.01); *C07K 2317/73* (2013.01); *C07K 2317/76* (2013.01); *C07K 2317/77* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 5,624,821 | A | 4/1997 | Winter et al. |
| 5,648,260 | A | 7/1997 | Winter et al. |
| 5,731,168 | A | 3/1998 | Carter et al. |
| 5,821,337 | A | 10/1998 | Carter et al. |
| 5,869,046 | A | 2/1999 | Presta et al. |
| 6,194,516 | B1 | 2/2001 | Kusakabe et al. |
| 6,194,551 | B1 | 2/2001 | Idusogie et al. |
| 6,248,516 | B1 | 6/2001 | Winter et al. |
| 6,455,043 | B1 | 9/2002 | Grillo-Lopez |
| 6,602,684 | B1 | 8/2003 | Umana et al. |
| 6,737,056 | B1 | 5/2004 | Presta et al. |
| 7,332,581 | B2 | 2/2008 | Presta |
| 7,371,826 | B2 | 5/2008 | Presta |
| 7,682,612 | B1 | 3/2010 | White et al. |
| 7,695,936 | B2 | 4/2010 | Carter et al. |
| 7,799,900 | B2 | 9/2010 | Adams et al. |
| 8,219,149 | B2 | 7/2012 | Lafata et al. |
| 8,562,992 | B2 | 10/2013 | Adams et al. |
| 8,709,421 | B2 | 4/2014 | Heiss |
| 8,969,526 | B2 | 3/2015 | Baehner et al. |
| 9,000,130 | B2 | 4/2015 | Bhakta et al. |
| 9,308,257 | B2 | 4/2016 | Sharma et al. |
| 9,315,567 | B2 | 4/2016 | Chang et al. |

(Continued)

FOREIGN PATENT DOCUMENTS

| | | |
|---|---|---|
| CN | 102369214 A | 3/2012 |
| EP | 1 870 459 A1 | 12/2007 |

(Continued)

OTHER PUBLICATIONS

Anderson et al., "G19.4(alpha CD3)×B43(alpha CD19) monoclonal antibody heteroconjugate triggers CD19 antigen-specific lysis of t(4;11) acute lymphoblastic leukemia cells by activated CD3 antigen-positive cytotoxic T cells" Blood 80(11):2826-34 ( 1992).

(Continued)

*Primary Examiner* — Mark Halvorson
(74) *Attorney, Agent, or Firm* — Clark & Elbing LLP; Thomas J. Takara

(57) ABSTRACT

The present invention relates to anti-CLL-1 antibodies including anti-CLL-1 antibodies comprising a CLL-1 binding domain and a CD3 binding domain (e.g., anti-CLL-1/CD3 T cell dependent bispecific (TDB) antibody) and methods of using the same.

17 Claims, 33 Drawing Sheets
Specification includes a Sequence Listing.

(56) References Cited

U.S. PATENT DOCUMENTS

| | | |
|---|---|---|
| 9,587,021 B2 | 3/2017 | Huang et al. |
| 9,657,102 B2 | 5/2017 | Smith et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0031613 A1 | 2/2005 | Nakamura et al. |
| 2005/0095243 A1 | 5/2005 | Chan et al. |
| 2005/0123546 A1 | 6/2005 | Umana et al. |
| 2006/0177451 A1 | 8/2006 | van den Oudenrijn et al. |
| 2007/0134759 A1 | 6/2007 | Nishiya et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0285037 A1 | 11/2010 | Arbo et al. |
| 2010/0331527 A1 | 12/2010 | Davis et al. |
| 2011/0020322 A1 | 1/2011 | Wilkins et al. |
| 2011/0256157 A1 | 10/2011 | Howard et al. |
| 2012/0251531 A1 | 10/2012 | Baehner et al. |
| 2013/0028917 A1 | 1/2013 | Howard et al. |
| 2013/0129723 A1 | 5/2013 | Blankenship et al. |
| 2013/0165638 A1 | 6/2013 | Hsu et al. |
| 2013/0171095 A1 | 7/2013 | Bernett |
| 2013/0266595 A1 | 10/2013 | Flygare et al. |
| 2013/0287774 A1 | 10/2013 | Zugmaier et al. |
| 2014/0088295 A1 | 3/2014 | Smith et al. |
| 2014/0112914 A1 | 4/2014 | Nezu et al. |
| 2014/0187753 A1 | 7/2014 | Blein et al. |
| 2014/0288280 A1 | 9/2014 | Bhakta et al. |
| 2014/0294868 A1 | 10/2014 | Howard |
| 2014/0302064 A1 | 10/2014 | Moore et al. |
| 2014/0341902 A1 | 11/2014 | Maecker et al. |
| 2014/0377270 A1 | 12/2014 | Moore et al. |
| 2015/0098900 A1 | 4/2015 | Ebens et al. |
| 2015/0110791 A1 | 4/2015 | Zhang et al. |
| 2015/0133640 A1 | 5/2015 | Blein et al. |
| 2015/0165063 A1 | 6/2015 | Flygare et al. |
| 2015/0166661 A1 | 6/2015 | Chen et al. |
| 2015/0266966 A1 | 9/2015 | Smith et al. |
| 2016/0017058 A1 | 1/2016 | Kim et al. |
| 2016/0074527 A1 | 3/2016 | Flygare et al. |
| 2016/0075785 A1 | 3/2016 | Ast et al. |
| 2016/0075787 A1 | 3/2016 | Zheng et al. |
| 2016/0090416 A1 | 3/2016 | Gunde et al. |
| 2016/0159906 A1 | 6/2016 | Sun et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0158773 A1 | 6/2017 | Adams et al. |
| 2017/0204194 A1 | 7/2017 | Chen et al. |
| 2017/0224818 A1 | 8/2017 | Lindhofer et al. |
| 2017/0267783 A1 | 9/2017 | Nezu et al. |
| 2018/0057593 A1 | 3/2018 | Dennis et al. |
| 2018/0134798 A1 | 5/2018 | Chu et al. |

FOREIGN PATENT DOCUMENTS

| | | |
|---|---|---|
| EP | 1 870 459 A4 | 12/2007 |
| EP | 1 870 459 B1 | 12/2007 |
| EP | 2 578 230 | 4/2013 |
| EP | 2 647 707 A1 | 9/2013 |
| EP | 2 647 707 A4 | 9/2013 |
| EP | 2647707 A4 | 4/2014 |
| JP | 2008-291036 | 12/2008 |
| JP | 2009-539413 | 11/2009 |
| JP | 2012-511329 A | 5/2012 |
| JP | 2013-515509 | 5/2013 |
| JP | 2013/529084 | 7/2013 |
| JP | 6449295 B2 | 1/2019 |
| WO | 91/03493 | 3/1991 |
| WO | WO-91/03493 A1 | 3/1991 |
| WO | 94/29351 A2 | 12/1994 |
| WO | 96/01126 | 1/1996 |
| WO | 96/027011 A1 | 9/1996 |
| WO | 97/30087 A1 | 8/1997 |
| WO | 98/050431 A2 | 11/1998 |
| WO | 98/050431 A3 | 11/1998 |
| WO | 98/58964 A1 | 12/1998 |
| WO | 99/22764 A1 | 5/1999 |
| WO | 99/51642 A1 | 10/1999 |
| WO | 00/61739 A1 | 10/2000 |
| WO | 01/29246 A1 | 4/2001 |
| WO | 02/31140 A1 | 4/2002 |
| WO | 03/011878 A2 | 2/2003 |
| WO | 03/084570 A1 | 10/2003 |
| WO | 03/085107 A1 | 10/2003 |
| WO | 03/085119 | 10/2003 |
| WO | 2004/056312 A2 | 7/2004 |
| WO | 2005/035586 A1 | 4/2005 |
| WO | 2005/035778 A1 | 4/2005 |
| WO | 2005/053742 A1 | 6/2005 |
| WO | 2005000894 A3 | 6/2005 |
| WO | 2005/100402 A1 | 10/2005 |
| WO | 2006/029879 A2 | 3/2006 |
| WO | 2007/042261 | 4/2007 |
| WO | 2007/110205 | 10/2007 |
| WO | 2007/146968 A2 | 12/2007 |
| WO | 2008/077546 A1 | 7/2008 |
| WO | 2008/119566 | 10/2008 |
| WO | 2008/119567 A2 | 10/2008 |
| WO | 2009/070642 | 6/2009 |
| WO | 2010/077643 | 7/2010 |
| WO | WO-2010/077634 A1 | 7/2010 |
| WO | 2010/114940 | 10/2010 |
| WO | WO-2010/115589 A1 | 10/2010 |
| WO | 2011/028952 A1 | 3/2011 |
| WO | 2011/061492 A2 | 5/2011 |
| WO | 2011/090762 A1 | 7/2011 |
| WO | 2011/130598 | 10/2011 |
| WO | 2011/131746 A2 | 10/2011 |
| WO | 2011/131746 A3 | 10/2011 |
| WO | 2011/143545 | 11/2011 |
| WO | 2011/156328 A1 | 12/2011 |
| WO | 2012/058768 A1 | 5/2012 |
| WO | 2012/058768 A8 | 6/2012 |
| WO | 2012/073985 | 6/2012 |
| WO | 2012/143524 A2 | 10/2012 |
| WO | 2012/158818 | 11/2012 |
| WO | 2012/162067 | 11/2012 |
| WO | 2013/055987 A1 | 4/2013 |
| WO | 2013/165940 | 11/2013 |
| WO | 2013/169625 | 11/2013 |
| WO | 2014/022540 A1 | 2/2014 |
| WO | 2014/028560 A2 | 2/2014 |
| WO | 2014/028560 A3 | 2/2014 |
| WO | 2014/047231 A1 | 3/2014 |
| WO | 2014/051433 | 4/2014 |
| WO | WO-2014/051433 A1 | 4/2014 |
| WO | 2014/122251 A2 | 8/2014 |
| WO | 2014/122251 A3 | 8/2014 |
| WO | 2014/141152 A3 | 9/2014 |
| WO | 2014/153002 A1 | 9/2014 |
| WO | 2014/159981 A2 | 10/2014 |
| WO | 2014/141152 A2 | 12/2014 |
| WO | 2014/191113 A1 | 12/2014 |
| WO | 2014/191113 A8 | 12/2014 |
| WO | 2014/193973 | 12/2014 |
| WO | 2015/006749 A2 | 1/2015 |
| WO | 2015/023355 A1 | 2/2015 |
| WO | 2015/095124 A1 | 6/2015 |
| WO | 2015/095212 A1 | 6/2015 |
| WO | 2015/095392 | 6/2015 |
| WO | 2015181559 | 12/2015 |
| WO | 2016/020065 A1 | 2/2016 |
| WO | 2016/036678 | 3/2016 |
| WO | 2016040868 A1 | 3/2016 |
| WO | 2016044560 | 3/2016 |
| WO | 2016/081490 | 5/2016 |
| WO | 2016090050 | 6/2016 |

(56) References Cited

FOREIGN PATENT DOCUMENTS

| WO | 2016/110576 | A1 | 7/2016 |
|---|---|---|---|
| WO | 2016/179003 | | 11/2016 |
| WO | 2016/191750 | A1 | 12/2016 |
| WO | 2016/204966 | | 12/2016 |
| WO | 2016/205520 | | 12/2016 |
| WO | 2016/205531 | A2 | 12/2016 |
| WO | 2017/132279 | | 8/2017 |
| WO | 2018/093821 | | 5/2018 |

OTHER PUBLICATIONS

Atwell et al., "Stable heterodimers from remodeling the domain interface of a homodimer using a phage display library" J Mol Biol 270(1):26-35 ( 1997).
Baeuerle and Reinhardt, "Bispecific T-cell engaging antibodies for cancer therapy" Cancer Res 69(12):4941-4944 ( 2009).
Bortoletto et al., "Optimizing anti-CD3 affinity for effective T cell targeting against tumor cells" Eur J Immunol 32(11):3102-7 ( 2002).
Brekke et al., "Human IgG Isotype-Specific Amino Acid Residues Affecting Complement-Mediated Cell Lysis and Phagocytosis." Eur J Immunol 24(10):2542-2547 (Oct. 1994).
Brown, M. et al., "Tolerance to single, but not multiple, amino acid replacements in antibody VH CDR 2: a means of minimizing B cell wastage from somatic hypermutation?" The Journal of Immunology (cited in RU examination report), 156:3285-3291 ( 1996).
Brueggemann et al., "Comparison of the effector functions of human immunoglobulins using a matched set of chimeric antibodies"0 J. Exp. Med. 166:1351-1361 ( 1987).
Carter, "Bispecific human IgG by design" J Immunol Methods 248(1-2):7-15 (Feb. 1, 2001).
Clark, L. A. et al., "Affinity enhancement of an in vivo matured therapeutic antibody using structure-based computational design" Prot Sci 15:949-960 ( 2006).
Clynes et al., "Fc receptors are requirement in passive and active immunity to melanoma" P Natl Acad Sci USA 95(2):652-656 (Jan. 1998).
Communication pursuant to Article 94(3) dated Apr. 10, 2017, for Chen et al., "Anti-CD3 Antibodies and Methods of Use," European Patent Application No. 14828608.1, filed Dec. 17, 2014 (7 pages)., pp. 7 Dec. 17, 2014.
Communication pursuant to Article 94(3) dated Aug. 2, 2018, for Chen et al., "Anti-CD3 Antibodies and Methods of Use," European Patent Application No. 14828608.1, filed Dec. 17, 2014 (10 pages)., pp. 10 Dec. 17, 2014.
Communication pursuant to Article 94(3) dated Nov. 5, 2018, for Dennis, "Masked Anti-CD3 Antibodies and Methods of Use," European Patent Application No. 16724772.5, pp. 10 Apr. 29, 2016.
Communication pursuant to Article 94(3) dated Nov. 8, 2017, issued in European Patent Application No. 16733812.8, pp. 7.
Communication pursuant to Article 94(3) dated Nov. 9, 2018, "Anti-CD3 Antibodies and Methods of Use," European Patent Application No. 14828608, pp. 11 Nov. 8, 2017.
Cragg et al., "Antibody specificity controls in vivo effector mechanisms of anti-CD20 reagents" Blood 103(7):2738-2743 ( 2004).
Donaldson et al., "Design and development of masked therapeutic antibodies to limit off-target effects: application to anti-EGFR antibodies" Cancer Biol Ther 8(22):2145-50 ( 2009).
Duncan et al., "The binding site for C1q and IgG" Nature 332(6166):738-40 ( 1988).
Edelman et al., "The covalent structure of an entire yG immunoglobulin molecule" Proc. Natl. Acad. Sci. USA 63:78-85 ( 1969).
Examination Report dated Aug. 24, 2018, for Chen et al., "Anti-CD3 Antibodies and Methods of Use," Singaporean Patent Application No. 10201800250X, filed Dec. 17, 2014 (4 pages)., pp. 4 Dec. 17, 2014.
Examination Report dated Nov. 12, 2018, for Chen et al., "Anti-CD3 Antibodies and Methods of Use," New Zealand Patent Application No. 721309, filed Dec. 17, 2014 (5 pages)., pp. 5 (ER dated Nov. 12, 2018 for New Zealand Patent Application No. 721309 dated Nov. 12, 2018).
Extended European Search Report dated May 29, 2017, for Chen et al., "Anti-CD3 Antibodies and Methods of Use," European Patent Application No. 17156352.1, filed Dec. 17, 2014 (10 pages)., pp. 10 Dec. 17, 2014.
Gazzano-Santoro et al., "A non-radioactive complement-dependent cytotoxicity assay for anti-CD20 monoclonal antibody" J Immunol Methods 202:163-171 ( 1997).
Guyer et al., "Immunoglobulin binding by mouse intestinal epithelial cell receptors" J Immunol 117(2):587-593 (Aug. 1976).
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Holliger et al., "Diabodies': Small bivalent and bispecific antibody fragments" P Natl Acad Sci USA 90:6444-6448 (Jul. 1993).
Holliger et al., "Specific killing of lymphoma cells by cytotoxic T-cells mediated by a bispecific diabody" Protein Engineering 9(3):299-305 ( 1996).
Honeychurch et al., "Bispecific Ab therapy of B-cell lymphoma: target cell specificity of antibody derivatives appears critical in determining therapeutic outcome" Cancer Immunol Immunother 45:171-173 ( 1997).
Hosseini et al., "Abstract B043: Systems pharmacology modeling of anti-CD20/CD3 T-cell dependent bispecific antibody and its application to clinical trial design" Proceedings of the Second CRI-CIMT-EATI-AACR International Cancer Immunotherapy Conference: Translating Science into Survival, New York USA, pp. 4 ( Sep. 25-28, 2016).
Hosseini et al., "Systems pharmacology modeling of anti-CD20/CD3 T-cell dependent bispecific antibody and its application to clinical trial design" Poster American Conference on Pharmacometrics 7, Bellevue USA, pp. 1 ( Oct. 25, 2016).
Hudson et al., "Engineering antibodies" Nature Medicine 9(1):129-134 (Jan. 2003).
Idusogie et al., "Mapping of the C1q Binding Site on Rituxan, A Chimeric Antibody with a Human IgG1 Fc" J Immunol 164(8):4178-4184 ( 2000).
Igawa et al., "VH/VL interface engineering to promote selective expression and inhibit conformational isomerization of thrombopoietin receptor agonist single-chain diabody," Protein Engineering, Design & Selection 23(8):667-677 (2010).
International Preliminary Report on Patentability dated Dec. 19, 2017, for Hotzel et al., "Humanized and Affinity Matured Antibodies to FCRH5 and Methods of Use," International Patent Application No. PCT/US2016/037879, filed Jun. 16, 2016 (12 pages)., pp. 12 (12 Jun. 16, 2016).
International Preliminary Report on Patentability dated Jun. 21, 2016, for Chen et al., "Anti-CD3 Antibodies and Methods of Use," International Patent Application No. PCT/US2014/070951, filed Dec. 17, 2014 (19 pages)., pp. 19 Dec. 17, 2014.
International Preliminary Report on Patentability dated Nov. 7, 2017, for Dennis, "Masked Anti-CD3 Antibodies and Methods of Use," International Patent Application No. PCT/US2016/030127, filed Apr. 29, 2016 (9 pages)., pp. 9 Apr. 29, 2016.
International Search Report and Written Opinion dated Aug. 3, 2016 for Dennis, "Masked Anti-CD3 Antibodies and Methods of Use," International Patent Application No. PCT/US2016/030127, filed Apr. 29, 2016 (15 pages)., pp. 15 dated Aug. 3, 2016.
International Search Report and Written Opinion dated Feb. 23, 2018, for Li et al., "Dosing for Treatment With Anti-CD20/Anti-CD3 Bispecific Antibodies," International Patent Application No. PCT/US2017/061683, filed Nov. 15, 2017 (14 pages)., pp. 14 Nov. 15, 2017.
International Search Report and Written Opinion dated May 28, 2015, for Chen et al., "Anti-CD3 Antibodies and Methods of Use," International Patent Application No. PCT/US2014/070951, filed Dec. 17, 2014 (33 pages)., pp. 33 Dec. 17, 2014.

(56) References Cited

OTHER PUBLICATIONS

International Search Report and Written Opinion dated Nov. 4, 2016, for Hotzel et al., "Humanized and Affinity Matured Antibodies to FCRH5 and Methods of Use," International Patent Application No. PCT/US2016/037879, filed Jun. 16, 2016 (20 pages)., pp. 20 Jun. 16, 2016.

Invitation to Pay Additional Fees mailed Apr. 9, 2015, for Chen et al., "Anti-CD3 Antibodies and Methods of Use," International Patent Application No. PCT/US2014/070951, filed Dec. 17, 2014 (12 pages)., pp. 12 Dec. 17, 2014.

Invitation to Pay Additional Fees mailed Sep. 12, 2016, for Hotzel et al., "Humanized and Affinity Matured Antibodies to FCRH5 and Methods of Use," International Patent Application No. PCT/US2016/037879, filed Jun. 16, 2016 (8 pages)., pp. 12 Jun. 16, 2016.

Jager et al., "The Trifunctional Antibody Ertumaxomab Destroys Tumor Cells That Express Low Levels of Human Epidermal Growth Factor Receptor 2" Cancer Res 69(10):4270-76 ( 2009).

Junttila et al., "Antitumor Efficacy of a Bispecific Antibody That Targets HER2 and Activates T Cells" Cancer Res 74(19) ( 2014).

Kanda et al., "Comparison of cell lines for stable production of fucose-negative antibodies with enhanced ADCC" Biotechnol Bioeng 94(4):680-688 (Jul. 5, 2006).

Kegg Drug Database, "Drug: Trastuzumab," <https://www.genome.jp/dbget-bin/www_bget?dr:D03257>, retrieved on Jan. 8, 2019 (2 pages)., pp. 2 (Drug: Trastuzumab Jan. 8, 2019).

Kiewe et al., "Phase 1 trial of the trifunctional anti-HER2×anti-CD3 antibody ertumaxomab in metastatic breast cancer" J Clin Oncol 23(16(s)):2530 ( 2005).

Kiewe et al., "Phase 1 trial of the trifunctional anti-HER2×anti-CD3 antibody ertumaxomab in metastatic breast cancer" Clin Cancer Res 12(10):3085-91 ( 2006).

Kim et al., "Localization of the site of the murine IgG1 molecule that is involved in binding to the murine intestinal Fc receptor" Eur J Immunol 24(10):2429-2434 (Oct. 1994).

Kipriyanov et al., "Bispecific Tandem Diabody for Tumor Therapy with Improved Antigen Binding and Pharmacokinetics" J. Mol. Biol. 293:41-56 ( 1999).

Klein et al., "Progress in overcoming the chain association issue in bispecific heterodimeric IgG antibodies" Landes Bioscience 4(6):653-663 ( 2012).

Kontermann, "Dual targeting strategies with bispecific antibodies" mAbs (Mar./Apr. 2012), 4(2):182-197.

Law et al., "Expression and characterization of recombinant soluble human CD3 molecules: presentation of antigenic epitopes defined on the native TCR-CD3 complex" Int Immunol 14(4):389-400 (2002).

Leabman et al., "Effects of altered FcgammaR binding on antibody pharmacokinetics in cynomolgus monkeys" MAbs 5(6):896-903 (2013).

Li et al., "Successful QSP modeling in drug development starts with the right questions" American Conference on Pharmacometrics 8, Fort Lauderdale USA, pp. 20 (2017).

Lippow et al., "Computational design of antibody affinity improvement beyond in vivo maturation" Nat Biotechnol 25(10):1171-6 (2007).

Lum et al., "Targeting T Cells 1-25, with Bispecific Antibodies for Cancer Therapy" Biodrugs 25(6):365-79 ( 2011).

Liu et al., "Improvement in soluble expression levels of a diabody by exchanging expression vectors," Protein Expr Purif. 62(1):15-20 (2008) (6 pages).

Merchant et al., "An efficient route to human bispecific IgG" Nat Biotechnol 16(7):677-681 ( 1998).

Metz, S. et al., "Bispecific antibody derivatives with restricted binding functionalities that are activated by proteolytic processing" Protein Engineering, Design & Selection 25(10):571-580 ( 2012).

Moore et al., "Application of dual affinity retargeting molecules to achieve optimal redirected T-cell killing of B-cell lymphoma" Blood 117(17):4542-51 ( 2011).

Nagorsen et al., "Immunomodulatory therapy of cancer with T cell-engaging BiTE antibody" Exp Cell Res. 317(9):1255-60 (2011).

Notice for Reasons for Rejection for Japanese Patent Applcation No. 2017-221759, dated Dec. 11, 2018 (6 pages)., pp. 6 (Notice for Reasons for Rejection for Japanese Patent Application No. 2017-221759 dated Dec. 11, 2018).

Notice of Reasons for Rejection dated Dec. 19, 2017, for Chen et al., "Anti-CD3 Antibodies and Methods of Use," Japanese Patent Application No. 2016-539276, filed Dec. 17, 2014 (6 pages)., pp. 6 dated Dec. 19, 2017.

Notice of Reasons for Rejection dated Jul. 31, 2018, for Chen et al., "Anti-CD3 Antibodies and Methods of Use," Japanese Patent Application No. 2016-539276, filed Dec. 17, 2014 (6 pages), dated Jul. 31, 2018.

Office Action for Eurasian Patent Application No. 201691266, dated Dec. 5, 2018 (14 pages)., pp. 14 (Office Action for Eurasian Patent Application No. 201691266, dated Dec. 5, 2018 dated Dec. 5, 2018).

Office Action for Chinese Patent Application No. 201480075726.X, dated Dec. 29, 2018 (11 pages).

Okazaki et al., "Fucose depletion from human IgG1 oligosaccharide enhances binding enthalpy and association rate between IgG1 and FcgammaRIIIa" J Mol Biol 336(5):1239-1249 (Mar. 5, 2004).

Pessano et al., "The T3/T cell receptor complex: antigenic distinction between the two 20-kd T3 subunits" EMBO Journal 4(2):337-344 ( 1985).

Petkova et al., "Enhanced half-life of genetically engineering human IgG1 antibodies in a humanized FcRn mouse model: potential application in humorally mediated autoimmune disease" Int Immunol 18(12):1759-69 (Dec. 2006).

Ravetch et al., "Fc receptors" Annu Rev Immunol 9:457-492 (1991).

Ridgway et al., "Knobs-into-holes' Engineering of Antibody C$\setminus\setminus\setminus$subscript:H$\setminus\setminus\setminus$3 Domains for Heavy Chain Heterodimerization" Protein Eng 9(7):617-621 ( 1996).

Riedle et al., "In Vivo Activation and Expansion of T Cells by a Bi-Specific Antibody Abolishes Metastasis Formation of Human Melanoma Cells" Int. J. Cancer 75:908-918 ( 1998).

Ripka et al., "Two chinese hamster ovary glycosylation mutants affected in the conversion of GDP-mannose to GDP-fucose" Arch Biochem Biophys 249(2):533-545 (Sep. 1986).

Search Report dated Aug. 24, 2018, for Chen et al., "Anti-CD3 Antibodies and Methods of Use," Singaporean Patent Application No. 10201800250X, filed Dec. 17, 2014 (3 pages)., pp. 3 Dec. 17, 2014.

Search Report dated Aug. 25, 2018, for Chen et al., "Anti-CD3 Antibodies and Methods of Use," Taiwanese Patent Application No. 103144203, filed Dec. 17, 2014 (2 page)., pp. 2 Dec. 17, 2014.

Search Report dated Aug. 8, 2017, for Chen et al., "Anti-CD3 Antibodies and Methods of Use," Singaporean Patent Application No. 11201604990P, filed Dec. 17, 2014 (6 pages)., pp. 6 dated Aug. 8, 2017.

Seimetz et al., "Development and approval of the trifunctional antibody catumaxomab (anti-EpCAM×anti-CD3) as a target cancer immunotherapy" Cancer Treatment Reviews 36:458-467 ( 2010).

Shalaby et al., "Bispecific HER2×CD3 Antibodies Enhance T-Cell Cytotoxity in Vitro and Localize to HER2-Overexpressing Xenografts in Nude Mice" Clin Immunol Immunop 74(2):185-192 ( 1995).

Shen et al., "Preparation and characterization for bispecific antibodies of anti-CD3×anti-idiotype to B cell lymphocytic leukemia," J Tongji Med Univ. 19(3):166-9 (1999) (4 pages).

Shields et al. et al., "High resolution mapping of the binding site on human IgG1 for Fc gamma RI, Fc gamma RII, Fc gamma RIII, and FcRn and design of IgG1 varients with improved binding to the Fc gamma R" J Biol Chem 276(9):6591-6604 (Mar. 2, 2001).

Sondermann et al., "The 3.2-A crystal structure of the human IgG1 Fc fragmet-Fc gammaRIII complex" Nature 406(6793):267-273 (2000).

Spiess et al., "Bispecific antibodies with natural architecture produced by co-culture of bacteria expressing two distinct half-antibodies" Nature Biotechnology 31(8):753-758 (Aug. 2013).

(56) References Cited

OTHER PUBLICATIONS

Stubenrauch et al., "Impact of molecular processing in the hinge region of therapeutic IgG4 antibodies on disposition profiles in cynomolgus monkeys" Drug Metab Dispos. 38(1):84-91 (Jan. 2010).
Sun et al., "Anti-CD20/CD3 T cell-dependent bispecific antibody for the treatment of B cell malignancies" Science Trans Med 7(287):287ra70 (2015).
Westin et al., "Safety and activity of PD1 blockade by pidilizumab in combination with rituximab in patients with relapsed follicular lymphoma: a single group, open-label, phase 2 trial" The Lancet, Oncology 15(1):69-77 (Jan. 2014).
Wright et al., "Effect of glycosylation on antibody function: implications for genetic engineering" Trends Biotechnol. 15(1):26-32 (1997).
Written Opinion dated Aug. 8, 2017, for Chen et al., "Anti-CD3 Antibodies and Methods of Use," Singaporean Patent Application No. 11201604990P, filed Dec. 17, 2014 (7 pages)., pp. 7 Dec. 17, 2014.
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Zhenping, "Small data transmission" Int J Cancer 62:1-6 ( 2011).
Zhu et al., "Identification of heavy chain residues in a humanized anti-CD3 antibody important for efficient antigen binding and T cell activation." J Immunol 155:1903-10 ( 1995).
Zhu, Z. et al. et al., "Engineering High Affinity Humanized Anti-p185HER2/Anti-CD3 Bispecific F(ab')2 for Efficient Lysis of p185HER2 Overexpressing Tumor Cells" Int J Cancer 62:319-324 ( 1995).
International Search Report and Written Opinion for International Patent Application No. PCT/US2015/049794, dated 2016.
Osada et al., "CEA/CD3-bispecific T cell-engaging (BiTE) antibody-mediated T lymphocyte cytotoxicity maximized by inhibition of both PD1 and PD-LI" Cancer Immunology and Immunotherapy 64(6):677-688 (Jun. 1, 2015).
McClanahan et al., "PD-L1 checkpoint blockade prevents immune dysfunction and leukemia development in a mouse model of chronic lymphocytic leukemia" Blood 126(2):203-211 (Jul. 9, 2015).
Lu et al., "Targeting human C-type lectin-like molecule-1 (CLL1) with a bispecific antibody for immunotherapy of acute myeloid leukemia" Angewandte Chemie International Edition 53(37):9841-9845 (Sep. 8, 2014).
George et al., "Differential Effects of Anti-B2-Glycoprotein I Antibodies on Endothelial Cells on the Manifestations of Experimental Antiphospholipid Syndrome" Circulation 97:900-906 ( 1998).
Brusa et al., "The PD-1/PD-L1 axis contributes to T-cell dysfunction in chronic lymphocytic leukemia" Haematologica, The Hematology Journal 98(6):953-963 (Jan. 8, 2013).
International Search Report and Written Opinion for International Patent Application No. PCT/US2016/037381, pp. 1-13 ( dated Jun. 16, 2015).
Lippincott-Schwartz, "Antibodies in Cell Biological Tools" Current Protocols in Cell Biology:16.0.1-16.0.2 ( 2002).
Baeuerle et al., "Bispecific T-cell engaging antibodies for cancer therapy," Cancer Res. 69(12):4941-4 (2009).
Brueggemann et al., "Comparison of the effector functions of human immunoglobulins using a matched set of chimeric antibodies," J Exp Med. 166(5):1351-1361 (1987).
Cragg et al., "Antibody specificity controls in vivo effector mechanisms of anti-CD20 reagents," Blood. 103(7):2738-43 (2004).
Gazzano-Santoro et al., "A non-radioactive complement-dependent cytotoxicity assay for anti-CD20 monoclonal antibody," J Immunol Methods. 202(2):163-71 (1997).
Guyer et al., "Immunoglobulin binding by mouse intestinal epithelial cell receptors," J Immunol. 117(2):587-93 (1976).
Igawa et al., "VH/VL interface engineering to promote selective expression and inhibit conformational isomerization of thrombopoietin receptor agonist single-chain diabody," Protein Eng Des Sel. 23(8):667-77 (2010).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Ridgway et al., "Knobs-into-holes' Engineering of Antibody CH3 Domains for Heavy Chain Heterodimerization," Protein Eng. 9(7):617-621 (1996).
Shen et al., "Preparation and characterization of bispecific antibodies of anti-CD3×anti-idiotype to B cell lymphocytic leukemia," J Tongji Med Univ. 19(3):166-9 (1999) (4 pages).
Communication pursuant to Article 94(3) dated Nov. 8, 2017, issued in European Patent Application No. 16733712.8.
Extended European Search Report for European Patent Application No. 19219511.3 dated Jul. 15, 2020 (12 pages).
First Office Action and Search Report for Chinese Patent Application No. 201680033064.9, dated Jan. 21, 2021 (13 pages).
Notice of Reasons for Rejection for Japanese Patent Application No. 2017-513781, dated Feb. 18, 2020 (13 pages).
Notice of Reasons for Rejection for Japanese Patent Application No. 2017-513781, dated Nov. 17, 2020 (4 pages).
Notice of Reasons for Rejection for Japanese Patent Application No. 2017-563291, dated Mar. 9, 2021 (7 pages).
Notice of Reasons for Rejection for Japanese Patent Application No. 2017-563291, dated Jun. 2, 2020 (6 pages).
English Translation of Office Action and Search Report for Chinese Application No. 201680033064.9, dated Aug. 16, 2021 (14 pages).

| EC$_{50}$ (ng/ml) | Control<br>gD:38E4v1 | Very High<br>Affinity<br>h6E7:38E4v11 | High Affinity<br>h6E7A:38E4v11 | Low Affinity<br>h6E7A:40G5 |
|---|---|---|---|---|
| EOL-1 | >5000 ng/ml | 6 | 9 | 105 |
| THP-1 | >5000 ng/ml | 11 | 21 | 856 |
| HL-60 | >5000 ng/ml | 11 | 20 | 172 |

*FIG. 8D*

| h6E7 | Biacore nM | (V1) EC$_{50}$ ng/ml | (40G5c) EC$_{50}$ ng/ml |
|---|---|---|---|
| N54A | 3.1 | 14 | 287 |
| N54D | 113.2 | 91 | 13044 |
| N54S | 14.1 | 23 | 2458 |
| N54E | 5.1 | 22 | 131 |
| N54Q | ND | 12 | 345 |

*FIG. 8G*

Light Chain, Kappa: Humanized Antibody Aligned to 38E4v1

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 38E4v1  | D | I | V | M | T | Q | S | P | D | S | L | A | V | S | L | G | E | R | A | T | I | N | C | K | S | S | Q | S | L | L | N | S | R | T | R | K | N | Y | L | A | W | Y |
| 38E4v11 | D | I | V | M | T | Q | S | P | D | S | L | A | V | S | L | G | E | R | A | T | I | N | C | K | S | S | Q | S | L | L | N | S | R | T | R | K | N | Y | L | A | W | Y |
| 40G5c   | D | I | V | M | T | Q | S | P | D | S | L | A | V | S | L | G | E | R | A | T | I | N | C | K | S | S | Q | S | L | L | N | S | R | T | R | K | N | Y | L | A | W | Y |

CDR L1: positions 24–34 (KSSQSLLNSR...NYLA)

| Kabat Number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|
| 38E4v1  | Q | Q | K | P | G | Q | S | P | K | L | L | I | Y | W | T | S | T | R | K | S | G | V | P | D | R | F | S | G | S | G | S | G | T | D | F |
| 38E4v11 | Q | Q | K | P | G | Q | S | P | K | L | L | I | Y | W | T | S | T | R | K | S | G | V | P | D | R | F | S | G | S | G | S | G | T | D | F |
| 40G5c   | Q | Q | K | P | G | Q | P | P | K | L | L | I | Y | W | A | S | T | R | E | S | G | V | P | D | R | F | S | G | S | G | S | G | T | D | F |

CDR L2: positions 50–56

| Kabat Number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|
| 38E4v1  | T | L | T | I | S | S | L | Q | A | E | D | V | A | V | Y | Y | C | K | Q | S | F | H | L | . | . | R | T | F | G | Q | G | T | K | V | E | I | K |
| 38E4v11 | T | L | T | I | S | S | L | Q | A | E | D | V | A | V | Y | Y | C | K | Q | S | F | H | L | . | . | R | T | F | G | Q | G | T | K | V | E | I | K |
| 40G5c   | T | L | T | I | S | S | L | Q | A | E | D | V | A | V | Y | Y | C | K | Q | S | F | H | L | . | . | R | T | F | G | G | G | T | K | V | E | I | K |

CDR L3: positions 89–97

FIG. 16A

Heavy Chain: Humanized Antibody Aligned to 38E4v1

FIG. 16B

| Group | Cmax (µg/mL) | AUC All (Day*µg/mL) | CL (mL/Day/kg) | Vss (mL/kg) |
|---|---|---|---|---|
| h6E7A x h40G5c | 8.7 | 51.9 | 9.4 | 118.8 |
| h6E7A x 38E4v1 | 8.9 | 49.1 | 10.4 | 147.4 |
| h6E7A x 38E4v11 | 8.9 | 44.4 | 11.5 | 155.3 |
| anti-gD/40G5 | 7.7 | 53.6 | 9.2 | 145.6 |
| anti-gD/38E4v1 | 7.8 | 36.8 | 13.5 | 179.9 |

--- Compared to Vehicle Group Avg ---

| 15-0196B | % Avg Mono / EOS | % Avg Granulocytes |
|---|---|---|
| Vehicle | 100 | 100 |
| anti-PD-L1 | 74 | 48 |
| CLL-1 TDB 0.5 mg/kg | 6 | 25 |
| Combo | 2 | 13 | hCLL-1 non-detectable memb expression; results suggests an antigen-independent MOA

FIG. 22A

| 15-0196C | % Avg Mono / EOS | % Avg Granulocytes |
|---|---|---|
| Vehicle | 100 | 100 |
| anti-PD-L1 | 50 | 37 |
| CLL-1 TDB 0.5 mg/kg | 6 | 33 |
| Combo - High | 2* | 14* |
| CLL-1 TDB 0.1 mg/kg | 12 | 16 |
| Combo - Low | 18 | 19 | hCLL-1 non-detectable memb expression; results suggests an antigen-independent MOA Note: granulocyte gate based on CD11b$^+$ hCLL-1 negativity and SSC / FSC; small amount of monocytes in gate also CLL-1 negative
* Outlier #396 removed from analysis (suspect dosing)

FIG. 22B

SEQUENCE LISTING

<160> NUMBER OF SEQ ID NOS: 110

<210> SEQ ID NO 1
<211> LENGTH: 265
<212> TYPE: PRT
<213> ORGANISM: Homo sapiens

<400> SEQUENCE: 1

Met Ser Glu Glu Val Thr Tyr Ala Asp Leu Gln Phe Gln Asn Ser Ser

```
              1               5              10              15
            Glu Met Glu Lys Ile Pro Glu Ile Gly Lys Phe Gly Glu Lys Ala Pro
                            20              25              30

Pro Ala Pro Ser His Val Trp Arg Pro Ala Ala Leu Phe Leu Thr Leu
                        35              40              45

Leu Cys Leu Leu Leu Leu Ile Gly Leu Gly Val Leu Ala Ser Met Phe
                    50              55              60

His Val Thr Leu Lys Ile Glu Met Lys Met Asn Lys Leu Gln Asn
            65              70              75              80

Ile Ser Glu Glu Leu Gln Arg Asn Ile Ser Leu Gln Leu Met Ser Asn
                            85              90              95

Met Asn Ile Ser Asn Lys Ile Arg Asn Leu Ser Thr Thr Leu Gln Thr
                        100             105             110

Ile Ala Thr Lys Leu Cys Arg Glu Leu Tyr Ser Lys Glu Gln Glu His
                    115             120             125

Lys Cys Lys Pro Cys Pro Arg Arg Trp Ile Trp His Lys Asp Ser Cys
                130             135             140

Tyr Phe Leu Ser Asp Asp Val Gln Thr Trp Gln Glu Ser Lys Met Ala
            145             150             155             160

Cys Ala Ala Gln Asn Ala Ser Leu Leu Lys Ile Asn Asn Lys Asn Ala
                            165             170             175

Leu Glu Phe Ile Lys Ser Gln Ser Arg Ser Tyr Asp Tyr Trp Leu Gly
                        180             185             190

Leu Ser Pro Glu Glu Asp Ser Thr Arg Gly Met Arg Val Asp Asn Ile
                    195             200             205

Ile Asn Ser Ser Ala Trp Val Ile Arg Asn Ala Pro Asp Leu Asn Asn
                210             215             220

Met Tyr Cys Gly Tyr Ile Asn Arg Leu Tyr Val Gln Tyr Tyr His Cys
            225             230             235             240

Thr Tyr Lys Lys Arg Met Ile Cys Glu Lys Met Ala Asn Pro Val Gln
                            245             250             255

Leu Gly Ser Thr Tyr Phe Arg Glu Ala
                        260             265

<210> SEQ ID NO 2
<211> LENGTH: 201
<212> TYPE: PRT
<213> ORGANISM: Homo sapiens

<400> SEQUENCE: 2

His Val Thr Leu Lys Ile Glu Met Lys Met Asn Lys Leu Gln Asn
            1               5              10              15

Ile Ser Glu Glu Leu Gln Arg Asn Ile Ser Leu Gln Leu Met Ser Asn
                            20              25              30

Met Asn Ile Ser Asn Lys Ile Arg Asn Leu Ser Thr Thr Leu Gln Thr
                        35              40              45

Ile Ala Thr Lys Leu Cys Arg Glu Leu Tyr Ser Lys Glu Gln Glu His
                    50              55              60

Lys Cys Lys Pro Cys Pro Arg Arg Trp Ile Trp His Lys Asp Ser Cys
            65              70              75              80

Tyr Phe Leu Ser Asp Asp Val Gln Thr Trp Gln Glu Ser Lys Met Ala
                            85              90              95

Cys Ala Ala Gln Asn Ala Ser Leu Leu Lys Ile Asn Asn Lys Asn Ala
                        100             105             110
```

Leu Glu Phe Ile Lys Ser Gln Ser Arg Ser Tyr Asp Tyr Trp Leu Gly
            115                 120                 125

Leu Ser Pro Glu Glu Asp Ser Thr Arg Gly Met Arg Val Asp Asn Ile
        130                 135                 140

Ile Asn Ser Ser Ala Trp Val Ile Arg Asn Ala Pro Asp Leu Asn Asn
145                 150                 155                 160

Met Tyr Cys Gly Tyr Ile Asn Arg Leu Tyr Val Gln Tyr Tyr His Cys
                165                 170                 175

Thr Tyr Lys Lys Arg Met Ile Cys Glu Lys Met Ala Asn Pro Val Gln
            180                 185                 190

Leu Gly Ser Thr Tyr Phe Arg Glu Ala
            195                 200

<210> SEQ ID NO 3
<211> LENGTH: 118
<212> TYPE: PRT
<213> ORGANISM: Homo sapiens

<400> SEQUENCE: 3

Cys Pro Arg Arg Trp Ile Trp His Lys Asp Ser Cys Tyr Phe Leu Ser
1               5                   10                  15

Asp Asp Val Gln Thr Trp Gln Glu Ser Lys Met Ala Cys Ala Ala Gln
            20                  25                  30

Asn Ala Ser Leu Leu Lys Ile Asn Asn Lys Asn Ala Leu Glu Phe Ile
        35                  40                  45

Lys Ser Gln Ser Arg Ser Tyr Asp Tyr Trp Leu Gly Leu Ser Pro Glu
    50                  55                  60

Glu Asp Ser Thr Arg Gly Met Arg Val Asp Asn Ile Ile Asn Ser Ser
65                  70                  75                  80

Ala Trp Val Ile Arg Asn Ala Pro Asp Leu Asn Asn Met Tyr Cys Gly
                85                  90                  95

Tyr Ile Asn Arg Leu Tyr Val Gln Tyr Tyr His Cys Thr Tyr Lys Lys
            100                 105                 110

Arg Met Ile Cys Glu Lys
        115

<210> SEQ ID NO 4
<211> LENGTH: 265
<212> TYPE: PRT
<213> ORGANISM: Macaca fascicularis

<400> SEQUENCE: 4

Met Ser Glu Glu Val Thr Tyr Ala Asp Leu Lys Phe Gln Asn Ser Ser
1               5                   10                  15

Glu Thr Glu Lys Ile Gln Glu Ile Ala Lys Phe Gly Gly Lys Ala Pro
            20                  25                  30

Pro Ala Pro Ser Cys Val Trp Arg Pro Ala Ala Leu Phe Leu Thr Val
        35                  40                  45

Leu Cys Leu Leu Met Leu Ile Gly Leu Gly Val Leu Gly Ser Met Phe
    50                  55                  60

His Ile Thr Leu Lys Thr Ala Met Lys Lys Met Asn Lys Leu Gln Asn
65                  70                  75                  80

Ile Asn Glu Glu Leu Gln Arg Asn Val Ser Leu Gln Leu Met Ser Asn
                85                  90                  95

Met Asn Ser Ser Asn Lys Ile Arg Asn Leu Ser Thr Thr Leu Gln Thr
            100                 105                 110

```
Ile Ala Thr Arg Leu Cys Arg Glu Leu Tyr Ser Lys Glu Gln Glu His
            115                 120                 125

Lys Cys Lys Pro Cys Pro Arg Arg Trp Ile Trp His Lys Asp Ser Cys
130                 135                 140

Tyr Phe Leu Ser Asp Asp Val Arg Thr Trp Gln Glu Ser Arg Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Thr Ser Tyr Pro Tyr Trp Leu Gly
            180                 185                 190

Leu Ser Pro Glu Lys Asp Tyr Ser Tyr Gly Thr Ser Val Asp Asp Ile
            195                 200                 205

Ile Asn Ser Ser Ala Trp Val Thr Arg Asn Ala Ser Asp Leu Asn Asn
            210                 215                 220

Met Phe Cys Gly Tyr Ile Asn Arg Ile Tyr Val His Tyr Asp Tyr Cys
225                 230                 235                 240

Ile Tyr Arg Lys Lys Met Ile Cys Glu Lys Met Ala Asn Pro Val Gln
                245                 250                 255

Leu Gly Phe Ile His Phe Arg Glu Ala
            260                 265

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ser Val Ser Thr Ser Ser Tyr Asn Tyr Met His
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ala Ser Asn Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln His Ser Trp Glu Ile Pro Leu Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 8

Asp Tyr Tyr Met His
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ile Asn Pro Tyr Asn Gly Ala Ala Phe Tyr Ser Gln Asn Phe Lys
1               5                   10                  15

Asp

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Arg Gly Ala Asp Leu Glu Gly Tyr Ala Met Asp Tyr
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ile Asn Pro Tyr Ala Gly Ala Ala Phe Tyr Ser Gln Asn Phe Lys
1               5                   10                  15

Asp

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ala Ser Ser Ser Ile Ser Tyr Met Tyr
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Thr Ser Lys Leu Ala Ser
```

```
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Gln Arg Ser Ser Trp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Asp Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Tyr Pro Gly Asp Gly Thr Thr Glu Tyr Asn Glu Arg Phe Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Tyr Asp Tyr Asp Tyr Ala Met Asp Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ala Ser Gln Asp Val Ser Thr Ala Val Ala
1               5                   10

<210> SEQ ID NO 19
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Ser Pro Ser Tyr Arg Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Leu Tyr Ser Thr Pro Tyr Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Tyr Leu Asp
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Val Asn Pro Tyr Asn Gly Gly Thr Ile Tyr Asn Gln Lys Phe Lys
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp His Tyr Arg Tyr Asp Pro Leu Leu Asp Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Ser Val Ser Ser Ser Ser Tyr Ser Tyr Met His
```

```
                1               5                  10                 15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln His Ser Trp Glu Ile Pro Tyr Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Thr Tyr Met His
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ile Asp Pro Ala Asn Gly Asp Thr Asp Tyr Asp Pro Lys Phe Gln
1               5                  10                 15

Gly

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Pro Pro Tyr Tyr Val Met Asp Tyr
1               5                  10

<210> SEQ ID NO 30
<211> LENGTH: 111
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 30

Asp Ile Val Leu Thr Gln Ser Pro Ser Ser Leu Ile Val Ser Leu Gly
1               5                   10                  15

Gln Arg Ala Thr Ile Ser Cys Arg Ala Ser Gln Ser Val Ser Thr Ser
            20                  25                  30

Ser Tyr Asn Tyr Met His Trp Tyr Gln Gln Lys Pro Gly Gln Pro Pro
        35                  40                  45

Lys Leu Leu Leu Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Ile Lys
            100                 105                 110

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met His Trp Val Lys Gln Ser His Ile Lys Ser Leu Glu Trp Ile
        35                  40                  45

Gly Arg Ile Asn Pro Tyr Asn Gly Ala Ala Phe Tyr Ser Gln Asn Phe
    50                  55                  60

Lys Asp Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Ser Val Thr Val Ser Ser
        115                 120

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30
```

Ser Tyr Asn Tyr Met His Trp Tyr Gln Gln Lys Pro Gly Lys Pro Pro
            35                  40                  45

Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
            85                  90                  95

Glu Ile Pro Leu Thr Phe Gly Gln Gly Thr Lys Val Glu Ile Lys
            100                 105                 110

<210> SEQ ID NO 33
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Ala Phe Tyr Ser Gln Asn Phe
    50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Ala Gly Ala Ala Phe Tyr Ser Gln Asn Phe
    50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 35
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Trp Thr Phe Gly
                85                  90                  95

Gly Gly Thr Lys Leu Glu Ile Lys
            100

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Leu Lys Gln Arg Pro Gly Gln Gly Leu Glu Trp Ile
        35                  40                  45

Gly Trp Ile Tyr Pro Gly Asp Gly Thr Thr Glu Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Ser Ser Leu Thr Ser Glu Asn Ser Ala Val Tyr Phe Cys
                85                  90                  95

Ala Arg Ser Tyr Asp Tyr Asp Tyr Ala Met Asp Tyr Trp Gly Gln Gly
            100                 105                 110

Thr Ser Val Thr Val Ser Ser
        115

<210> SEQ ID NO 37
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 37

Asp Ile Gln Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Phe Gln Gln Lys Pro Gly Gln Ser Pro Lys Leu Leu Ile
        35                  40                  45

Tyr Ser Pro Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Leu Tyr Ser Thr Pro Tyr
                85                  90                  95

Thr Phe Gly Gly Gly Thr Lys Leu Glu Ile Lys
            100                 105

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Leu Asp Trp Val Lys Gln Ser His Gly Glu Ser Phe Glu Trp Ile
        35                  40                  45

Gly Arg Val Asn Pro Tyr Asn Gly Gly Thr Ile Tyr Asn Gln Lys Phe
50                  55                  60

Lys Gly Lys Ala Thr Leu Thr Val Asp Lys Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Asp His Tyr Arg Tyr Asp Pro Leu Leu Asp Tyr Trp Gly Gln
            100                 105                 110

Gly Thr Thr Leu Thr Val Ser Ser
        115                 120

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Phe Gln Gln Lys Pro Gly Lys Ala Pro Lys Leu Leu Ile

```
                35                  40                  45
Tyr Ser Pro Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Leu Asp Trp Val Arg Gln Ala Pro Gly Gln Gly Leu Glu Trp Ile
            35                  40                  45

Gly Arg Val Asn Pro Tyr Asn Gly Gly Thr Ile Tyr Asn Gln Lys Phe
        50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp His Tyr Arg Tyr Asp Pro Leu Leu Asp Tyr Trp Gly Gln
            100                 105                 110

Gly Thr Leu Val Thr Val Ser Ser
        115                 120

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Ser Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Arg Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Arg Leu Glu Ile Lys
```

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Asp Tyr Asp Pro Lys Phe
    50                  55                  60

Gln Gly Lys Ala Thr Val Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ile Ser Gly Pro Pro Tyr Tyr Val Met Asp Tyr Trp Gly Gln Gly
            100                 105                 110

Thr Ser Val Thr Val Ser Ser
        115

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 43

Arg Ile Asn Pro Tyr Glu Gly Ala Ala Phe Tyr Ser Gln Asn Phe Lys
1               5                   10                  15

Asp

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 44

Arg Ile Asn Pro Tyr Ser Gly Ala Ala Phe Tyr Ser Gln Asn Phe Lys
1               5                   10                  15

Asp

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES

```
<222> LOCATION: (6)..(6)
<223> OTHER INFORMATION: Ala, Glu, Ser or Asn

<400> SEQUENCE: 45

Arg Ile Asn Pro Tyr Xaa Gly Ala Ala Phe Tyr Ser Gln Asn Phe Lys
1               5                   10                  15

Asp

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Ala, Glu, Ser or Asn

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Xaa Gly Ala Ala Phe Tyr Ser Gln Asn Phe
    50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Gly Gly Tyr Ala Met Asp Tyr Trp
            100                 105                 110

Gly Gln Gly Thr Leu Val Thr Val Ser Ser
        115                 120

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala, Glu or Ser

<400> SEQUENCE: 47

Arg Ile Asn Pro Tyr Xaa Gly Ala Ala Phe Tyr Ser Gln Asn Phe Lys
1               5                   10                  15

Asp

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (55)..(55)
<223> OTHER INFORMATION: Ala, Glu or Ser

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Xaa Gly Ala Ala Phe Tyr Ser Gln Asn Phe
    50                  55                  60

Lys Asp Arg Val Thr Leu Thr Val Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ser Cys Tyr Phe Leu Ser Asp Asp Val Gln Thr Trp Gln Glu Ser
1               5                   10                  15

Lys

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Arg Asn Leu Ser Thr Thr Leu Gln Thr Ile Ala Thr Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Leu Ser Thr Thr Leu Gln Thr Ile Ala Thr Lys
1               5                   10

<210> SEQ ID NO 52
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 52

Asp Tyr Lys Asp Asp Asp Lys Leu Glu His Val Thr Leu Lys
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Asp Asp Asp Lys Leu Glu His Val Thr Leu Lys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Asn Lys Leu Gln Asn Ile Ser Glu Glu Leu Gln Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Gln Asn Ile Ser Glu Glu Leu Gln Arg
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ile Ser Leu Gln Leu Met Ser Asn Met Asn Ile Ser Asn Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Leu Ser Thr Thr Leu Gln Thr Ile Ala Thr Lys Leu Cys Arg
1               5                   10                  15

```
<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Leu Tyr Ser Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Trp His Lys
1               5

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Ala Cys Ala Ala Gln Asn Ala Ser Leu Leu Lys
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Asn Asn Lys Asn Ala Leu Glu Phe Ile Lys
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Ala Leu Glu Phe Ile Lys
1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

Asn Ala Leu Glu Phe Ile Lys Ser Gln Ser Arg
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Tyr Asp Tyr Trp Leu Gly Leu Ser Pro Glu Glu Asp Ser Thr Arg
1               5                   10                  15

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Tyr Asp Tyr Trp Leu Gly Leu Ser Pro Glu Glu Asp Ser Thr Arg
1               5                   10                  15

Gly Met Arg

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Asp Asn Ile Ile Asn Ser Ser Ala Trp Val Ile Arg
1               5                   10

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Ala Pro Asp Leu Asn Asn Met Tyr Cys Gly Tyr Ile Asn Arg
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Tyr Val Gln Tyr Tyr His Cys Thr Tyr Lys
1               5                   10

<210> SEQ ID NO 69
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Ile Cys Glu Lys
1               5

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Ala Asn Pro Val Gln Leu Gly Ser Thr Tyr Phe Arg
1               5                   10

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asn Tyr Tyr Ile His
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Ile Tyr Pro Gly Asp Gly Asn Thr Lys Tyr Asn Glu Lys Phe Lys
1               5                   10                  15

Gly

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ser Tyr Ser Asn Tyr Tyr Phe Asp Tyr
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Lys Ser Ser Gln Ser Leu Leu Asn Ser Arg Thr Arg Lys Asn Tyr Leu
1               5                   10                  15

Ala

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Ala Ser Thr Arg Glu Ser
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Gln Ser Phe Ile Leu Arg Thr
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Tyr Tyr Ile His
1               5

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Ile Tyr Pro Glu Asn Asp Asn Thr Lys Tyr Asn Glu Lys Phe Lys
1               5                   10                  15

Asp

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Gly Tyr Ser Arg Tyr Tyr Phe Asp Tyr
1               5                   10

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Trp Thr Ser Thr Arg Lys Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Gln Ser Phe Ile Leu Arg Thr
1               5

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

```
Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Phe Ile Leu Arg Thr Phe Gly Gln Gly Thr Lys Val Glu Ile Lys
                100                 105                 110
```

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                 20                  25                  30

Tyr Ile His Trp Val Arg Gln Ala Pro Gly Gln Gly Leu Glu Trp Ile
             35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
        115
```

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95
```

```
Ser Phe Ile Leu Arg Thr Phe Gly Gln Gly Thr Lys Val Glu Ile Lys
                100                 105                 110
```

<210> SEQ ID NO 86
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25
```

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys
            20                  25
```

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn or Ser

<400> SEQUENCE: 88

```
Xaa Tyr Tyr Ile His
1               5
```

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Glu
<220> FEATURE:
<221> NAME/KEY: MOD_RES
<222> LOCATION: (6)..(6)
<223> OTHER INFORMATION: Asp or Asn
<220> FEATURE:
<221> NAME/KEY: MOD_RES
<222> LOCATION: (7)..(7)
<223> OTHER INFORMATION: Asp or Gly
<220> FEATURE:
<221> NAME/KEY: MOD_RES
<222> LOCATION: (17)..(17)
<223> OTHER INFORMATION: Asp or Gly

```
<400> SEQUENCE: 89

Trp Ile Tyr Pro Xaa Xaa Xaa Asn Thr Lys Tyr Asn Glu Lys Phe Lys
1               5                   10                  15

Xaa

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Gly
<220> FEATURE:
<221> NAME/KEY: MOD_RES
<222> LOCATION: (5)..(5)
<223> OTHER INFORMATION: Asn or Arg

<400> SEQUENCE: 90

Asp Xaa Tyr Ser Xaa Tyr Tyr Phe Asp Tyr
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (6)..(6)
<223> OTHER INFORMATION: Glu or Lys

<400> SEQUENCE: 91

Trp Xaa Ser Thr Arg Xaa Ser
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Thr

<400> SEQUENCE: 92

Xaa Gln Ser Phe Ile Leu Arg Thr
1               5

<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 93

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 94
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 95
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
            100                 105

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp or Gly

<400> SEQUENCE: 96

Gly Phe Thr Phe Ser Xaa Ser Trp Ile His
 1               5                  10

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Leu
<220> FEATURE:
<221> NAME/KEY: MOD_RES
<222> LOCATION: (10)..(10)
<223> OTHER INFORMATION: Thr or Ser

<400> SEQUENCE: 97

Ala Trp Ile Xaa Pro Tyr Gly Gly Ser Xaa Tyr Tyr Ala Asp Ser Val
 1               5                  10                  15

Lys Gly

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg His Trp Pro Gly Gly Phe Asp Tyr
 1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Thr Phe Ser Asp Ser Trp Ile His
```

```
1               5                   10
```

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Ala Trp Ile Ser Pro Tyr Gly Gly Ser Thr Tyr Tyr Ala Asp Ser Val
1               5                   10                  15

Lys Gly
```

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (9)..(9)
<223> OTHER INFORMATION: Ala or Phe
<220> FEATURE:
<221> NAME/KEY: MOD_RES
<222> LOCATION: (10)..(10)
<223> OTHER INFORMATION: Val or Leu

<400> SEQUENCE: 101

```
Arg Ala Ser Gln Xaa Xaa Xaa Thr Xaa Xaa Ala
1               5                   10
```

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Thr
<220> FEATURE:
<221> NAME/KEY: MOD_RES
<222> LOCATION: (6)..(6)
<223> OTHER INFORMATION: Tyr or Ala

<400> SEQUENCE: 102

```
Ser Ala Ser Xaa Leu Xaa Ser
1               5
```

<210> SEQ ID NO 103
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Gly, Phe or Ser
<220> FEATURE:
<221> NAME/KEY: MOD_RES
<222> LOCATION: (4)..(4)
<223> OTHER INFORMATION: Leu, Tyr, Phe or Trp
<220> FEATURE:
<221> NAME/KEY: MOD_RES
<222> LOCATION: (5)..(5)
<223> OTHER INFORMATION: Tyr, Asn, Ala, Thr, Gly, Phe or Ile
<220> FEATURE:
<221> NAME/KEY: MOD_RES
<222> LOCATION: (6)..(6)
<223> OTHER INFORMATION: His, Val, Pro, Thr or Ile
<220> FEATURE:
<221> NAME/KEY: MOD_RES
<222> LOCATION: (8)..(8)
<223> OTHER INFORMATION: Ala, Trp, Arg, Pro or Thr

<400> SEQUENCE: 103

Gln Gln Xaa Xaa Xaa Xaa Pro Xaa Thr
1               5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ala Ser Gln Asp Val Ser Thr Ala Val Ala
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ala Ser Phe Leu Tyr Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Tyr Leu Tyr His Pro Ala Thr
1               5

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 107

Gln Asp Gly Asn Glu Glu Met Gly Gly Ile Thr Gln Thr Pro Tyr Lys
1               5                   10                  15

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Tyr Lys Asp Asp Asp Asp Lys
1               5

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
            100                 105

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60
```

```
Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110
```

ANTI-CLL-1 ANTIBODIES AND METHODS OF USE

CROSS REFERENCE TO RELATED APPLICATIONS

This application is a division of U.S. application Ser. No. 15/182,327, filed 14 Jun. 2016, which claims the benefit of priority of provisional U.S. Application Nos. 62/180,376 filed 16 Jun. 2015, and 62/307,003 filed 11 Mar. 2016, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 26, 2019, is named P32920-WO_SL.txt and is 56 KB in size.

FIELD OF THE INVENTION

The present invention relates to anti-CLL-1 antibodies including anti-CLL-1 antibodies comprising a CLL-1 binding domain and a CD3 binding domain (e.g., anti-CLL-1/CD3 T cell dependent bispecific (TDB) antibody) and methods of using the same.

BACKGROUND

Cell proliferative disorders, such as cancer, are characterized by the uncontrolled growth of cell subpopulations. They are the leading cause of death in the developed world and the second leading cause of death in developing countries, with over 12 million new cancer cases diagnosed and 7 million cancer deaths occurring each year. The National Cancer Institute estimates that greater than half a million Americans will die of cancer in 2013, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

CLL-1 (also referred to as CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. CLL-1 has been shown to type II transmembrane receptor comprising a single C-type lectin-like domain (which is not predicted to bind either calcium or sugar), a stalk region, a transmembrane domain and a short cytoplasmic tail containing an ITIM motif. Further, CLL-1 is present on monocytes and granulocytes in normal peripheral blood and bone marrow (BM), while absent in nonhematological tissues. CLL-1 is also expressed on acute myeloid leukemia (AML), myelodisplastic syndrome (MDS), and chronic myelogenous leukemia (CML) cells. In particular, CLL-1 is a leukemia stem cell (LSC)-associated surface antigen expressed on a fraction of CD34+CD38+ AML cells in CD34 positive (CD34+) AML.

Monoclonal antibody (mAb)-based therapy has become an important treatment modality for cancer. Leukemia is well suited to this approach because of the accessibility of malignant cells in the blood, bone marrow, spleen, and lymph nodes and the well-defined immunophenotypes of the various lineages and stages of hematopoietic differentiation that permit identification of antigenic targets. Most studies for acute myeloid leukemia (AML) have focused on CD33. However, responses with the unconjugated anti-CD33 mAb lintuzumab have had modest single agent and activity against AML and failed to improve patient outcomes in two randomized trials when combined with conventional chemotherapy.

There is a need in the art for safe and effective agents that target AML including CLL-1 for the diagnosis and treatment of CLL-1-associated conditions, such as cancer. The invention fulfills that need and provides other benefits.

SUMMARY

The invention provides anti-CLL-1 antibodies comprising a CLL-1 binding domain and a CD3 binding domain and methods of using the same. In some embodiments, provided herein are isolated anti-CLL-1 antibodies, wherein the antibody comprises (i) a CLL-1 binding domain, wherein the CLL-1 binding domain binds a CLL-1 epitope and/or binds an overlapping CLL-1 epitope comprising amino acids of SEQ ID NO:49 and does not bind an epitope comprising SEQ ID NO:50 and/or SEQ ID NO:51; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain.

In some embodiments, the CLL-1 binding domain of the anti-CLL-1 antibody binds a CLL-1 epitope and/or binds an overlapping CLL-1 epitope comprising amino acids of SEQ ID NO:49 and does not bind a CLL-1 epitope comprising SEQ ID NO:50 and/or SEQ ID NO:51. In some embodiments, the CLL-1 binding domain of the anti-CLL-1 antibody binds a CLL-1 epitope comprising amino acids of SEQ ID NO:49. In some embodiments, the CLL-1 binding domain of the anti-CLL-1 antibody binds a CLL-1 epitope consisting or consisting essentially of the amino acids of SEQ ID NO:49. In some embodiments, the CLL-1 epitope is determined by hydroxyl radical footprinting.

For example, provided herein are anti-CLL1 antibodies comprising (i) a CLL-1 binding domain comprises the following six hypervariable regions (HVRs): (a) an HVR-H1 comprising the amino acid sequence of SEQ ID NO:8; (b) an HVR-H2 comprising the amino acid sequence of SEQ ID NO:45; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7 and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain. In some embodiments, the anti-CLL-1 antibody comprises a CLL-1 binding domain comprising a heavy chain variable region comprising the sequence of SEQ ID NO:46 and a light chain variable region comprising the sequence of SEQ ID NO:32

Further, for example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:9; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain. In some embodiments, the anti-CLL-1 antibody comprises a CLL-1 binding domain comprising a heavy chain variable region comprising the sequence of SEQ ID NO:33 and a light chain variable region comprising the sequence of SEQ ID NO:32.

In addition, for example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:47; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain. In some embodiments, the anti-CLL-1 antibody comprises a CLL-1 binding domain comprising a heavy chain variable region comprising the sequence of SEQ ID NO:48 and a light chain variable region comprising the sequence of SEQ ID NO:32.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain. In some embodiments, the anti-CLL-1 antibody comprises a CLL-1 binding domain comprising a heavy chain variable region comprising the sequence of SEQ ID NO:34 and a light chain variable region comprising the sequence of SEQ ID NO:32.

Further, for example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:43; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:44; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain.

For example, provided herein are anti-CLL1 antibodies comprising (i) a CLL-1 binding domain comprises the following six HVRs: (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain. In some embodiments, the anti-CLL-1 antibody comprises a CLL-1 binding domain comprising (a) a heavy chain variable region comprising the sequence of SEQ ID NO:40 and (b) a light chain variable region comprising the sequence of SEQ ID NO:39.

In some embodiments of any of the anti-CLL1 antibodies, the antibody comprises a CLL-1 binding domain has one or more of the following characteristics: a) binds to recombinant human CLL-1; b) binds to recombinant cynomolgus monkey CLL-1; c) binds to endogenous CLL-1 on the surface of human peripheral blood mononucleocytes (PBMCs); d) binds to endogenous CLL-1 on the surface of cynomolgus monkey PBMCs; e) binds to endogenous CLL-1 on the surface of a cancer cell; f) binds to endogenous CLL-1 on the surface of an AML cancer cell; g) binds to endogenous CLL-1 on the surface of HL-60 cells; h) binds to endogenous CLL-1 on the surface of EOL-1 cells; i) binds to CLL-1 comprising a K244Q mutation; j) competes for human CLL-1 binding with R&D clone 687317 antibody; k) binds to endogenous human CLL-1 with a Kd of less than 15 nM, less than 10 nM, less than 7 nM, less than 5 nM, or less than 3 nM; l) binds to recombinant human CLL-1 with a Kd of less than 10 nM, less than 7 nM, less than 5 nM, or less than 3 nM; and/or m) binds to recombinant cynomolgus monkey CLL-1 with a Kd of less than 10 nM, less than 7 nM, less than 5 nM, or less than 3 nM, less than 2 nM, or less than 1 nM.

In some embodiments of any of the anti-CLL1 antibodies, the antibody comprises a CD3 binding domain which binds a CD3 epitope comprising and/or consisting of Glu6 of human CD3ε polypeptide. In certain aspects, the CD3 epitope further comprises one or more additional amino acid residues selected from the group consisting of Gln1, Asp2, and Met7 of CD3. In some embodiments of any of the anti-CLL1 antibodies, the antibody comprises a CD3 binding domain which binds a CD3 epitope comprising and/or consisting of Gln1, Asp2, and Glu6 of human CD3ε polypeptide. In some embodiments of any of the anti-CLL1 antibodies, the antibody comprises a CD3 binding domain which binds a CD3 epitope comprising and/or consisting of Gln1, Asp2, Glu6, and Met7 of human CD3ε polypeptide. In another aspect, the CD3 epitope does not comprise amino acid residue Glu5 of human CD3ε polypeptide. In a further aspect, the CD3 epitope does not comprise amino acid residues Gly3 and Glu5 of human CD3ε polypeptide. In certain aspects, the CD3 epitope consists of amino acid residues Gln1, Asp2, Glu6, and Met7 of human CD3ε polypeptide.

In some embodiments, the CD3 binding arm of the anti-CLL1 antibody binds human CD3 with an affinity less than 50 nM and greater than 1 nM. In some embodiments, the CD3 binding arm of the anti-CLL1 antibody binds human CD3 with an affinity less than 1 nM and greater than 0.1 nM. In some embodiments, the CD3 binding arm of the anti-CLL1 antibody binds human CD3 with an affinity less than 0.1 nM and greater than 0.01 nM. In some embodiments, the affinity of the CD3 binding arm is determined by Biacore. In some embodiments, the human CD3 is hCD3εγ. In some embodiments, the human CD3 is hCD3ε 1-27 Fc.

In some embodiments of any of the anti-CLL1 antibodies, the antibody comprises a CD3 binding domain comprises the following six HVRs: (a) HVR-H1 comprising the amino acid sequence of SEQ ID NO:88; (b) HVR-H2 comprising the amino acid sequence of SEQ ID NO:89; (c) HVR-H3 comprising the amino acid sequence of SEQ ID NO:90; (d) HVR-L1 comprising the amino acid sequence of SEQ ID NO:74; (e) HVR-L2 comprising the amino acid sequence of SEQ ID NO:91; and (f) HVR-L3 comprising the amino acid sequence of SEQ ID NO:92. For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain comprises the following six HVRs: (a) HVR-H1 comprising the amino acid sequence of SEQ ID NO:88; (b) HVR-H2 comprising the amino acid sequence of SEQ ID NO:89; (c) HVR-H3 comprising the amino acid sequence of SEQ ID NO:90; (d) HVR-L1 comprising the amino acid sequence of SEQ ID NO:74; (e) HVR-L2 comprising the amino acid sequence of SEQ ID NO:91; and (f) HVR-L3 comprising the amino acid sequence of SEQ ID NO:92. In some embodiments, the anti-CLL-1 antibody comprises a CLL-1 binding domain comprising a heavy chain variable region comprising the sequence of SEQ ID NO:34 and a light chain variable region comprising the sequence of SEQ ID NO:32.

In some embodiments of any of the anti-CLL1 antibodies, the CD3 binding domain comprises (a) HVR-H1 comprising the amino acid sequence of SEQ ID NO:71; (b) HVR-H2 comprising the amino acid sequence of SEQ ID NO:72; (c) HVR-H3 comprising the amino acid sequence of SEQ ID NO:73; (d) HVR-L1 comprising the amino acid sequence of SEQ ID NO:74; (e) HVR-L2 comprising the amino acid sequence of SEQ ID NO:75; and (f) HVR-L3 comprising the amino acid sequence of SEQ ID NO:76. In some embodiments, the anti-CLL-1 antibody comprises a CD3 binding domain comprising a heavy chain variable region comprising the sequence of SEQ ID NO:82 and a light chain variable region comprising the sequence of SEQ ID NO:83. For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:71; (b) HVR-H2 comprising the amino acid sequence of SEQ ID NO:72; (c) HVR-H3 comprising the amino acid sequence of SEQ ID NO:73; (d) HVR-L1 comprising the amino acid sequence of SEQ ID NO:74; (e) HVR-L2 comprising the amino acid sequence of SEQ ID NO:75; and (f) HVR-L3 comprising the amino acid sequence of SEQ ID NO:76. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:82 and a light chain variable region comprising the sequence of SEQ ID NO:83.

In some embodiments of any of the anti-CLL1 antibodies, the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80 and (f) HVR-L3 comprising the amino acid sequence of SEQ ID NO:92. For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80 and (f) HVR-L3 comprising the amino acid sequence of SEQ ID NO:92. In some embodiments, the anti-CLL-1 antibody comprises a CLL-1 binding domain comprising a heavy chain variable region comprising the sequence of SEQ ID NO:34 and a light chain variable region comprising the sequence of SEQ ID NO:32.

In some embodiments of any of the anti-CLL1 antibodies, the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:81. In some embodiments, the anti-CLL-1 antibody comprises a CD3 binding domain comprising a heavy chain variable region comprising the sequence of SEQ ID NO:84 and a light chain variable region comprising the sequence of SEQ ID NO:85. For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:81. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:84 and a light chain variable region comprising the sequence of SEQ ID NO:85.

In some embodiments of any of the anti-CLL1 antibodies, the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:76. In some embodiments, the anti-CLL-1 antibody comprises a CD3 binding domain comprising a heavy chain variable region comprising the sequence of SEQ ID NO:84 and a light chain variable region comprising the sequence of SEQ ID NO:93. For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:76. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:84 and a light chain variable region comprising the sequence of SEQ ID NO:93.

In some embodiments of any of the anti-CLL-1 antibodies, the anti-CLL-1 antibody is a monoclonal, human, humanized, or chimeric antibody. In some embodiments of any of the anti-CLL-1 antibodies, the anti-CLL-1 antibody is an IgG antibody. In some embodiments of any of the anti-CLL-1 antibodies, the antibody is a bispecific antibody. In some embodiments of any of the anti-CLL-1 antibodies, the anti-CLL-1 antibody is an antibody fragment that binds CLL-1 and CD3. In some embodiments, the anti-CLL-1 antibody fragment is a Fab, Fab'-SH, Fv, scFv, and/or (Fab')$_2$ fragment. In some embodiments of any of the anti-CLL-1 antibodies, the anti-CLL-1 antibody is a full-length antibody.

In some embodiments of any of the anti-CLL-1 antibodies, the anti-CLL-1 antibody comprises an aglycosylation site mutation. In some embodiments, the aglycosylation site mutation is a substitution mutation.

In some embodiments of any of the anti-CLL-1 antibodies, the anti-CLL-1 antibody comprises reduced effector function. In some embodiments of any of the anti-CLL-1 antibodies, the anti-CLL-1 antibody comprises a substitution mutation is at amino acid residue N297, L234, L235, D265, and/or P329G according to EU numbering. In some embodiments, the substitution mutation is selected from the group consisting of N297G, N297A, L234A, L235A, D265A, and P329G according to EU numbering. In some embodiments, the anti-CLL-1 antibody comprises an N297G substitution mutation at amino acid residue 297 according to EU numbering. In some embodiments, the anti-CLL-1 antibody comprises an L234A, L235A, and P329G mutation at amino acid residues 234, 235, and 329 according to EU numbering.

In some embodiments of any of the multispecific anti-CLL-1 antibodies, the anti-CLL-1 antibody comprises one or more heavy chain constant domains, wherein the one or more heavy chain constant domains are selected from a first CH1 (CH1$_1$) domain, a first CH2 (CH2$_1$) domain, a first CH3 (CH3$_1$) domain, a second CH1 (CH1$_2$) domain, second CH2 (CH2$_2$) domain, and a second CH3 (CH3$_2$) domain. In some embodiments, at least one of the one or more heavy chain constant domains is paired with another heavy chain constant domain. In some embodiments, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some embodiments, the CH3$_1$ and CH3$_2$ domains meet at an interface between said protuberance and cavity. In some embodiments, the CH2$_1$ and CH2$_2$ domains each comprise a protuberance or cavity, and wherein the protuberance or cavity in the CH2$_1$ domain is positionable in the cavity or protuberance, respectively, in the CH2$_2$ domain. In some embodiments, the CH2$_1$ and CH2$_2$ domains meet at an interface between said protuberance and cavity.

In some embodiments of any of the anti-CLL-1 antibodies, (a) the CD3 binding domain comprises a Fc domain, wherein the Fc domain comprises T366S, L368A, Y407V, and N297G substitution mutations according EU numbering and (b) the CLL-1 binding domain comprises a Fc domain, wherein the Fc domain comprises T366W and N297G substitution mutations according EU numbering. In some embodiments of any of the anti-CLL-1 antibodies, (a) the CD3 binding domain comprises a Fc domain, wherein the Fc domain comprises L234A, L235A, P329G, T366S, L368A, and Y407V, substitution mutations according EU numbering and (b) the CLL-1 binding domain comprises a Fc domain, wherein the Fc domain comprises L234A, L235A, P329G, and T366W substitution mutations according EU numbering.

Further provided herein are isolated nucleic acids encoding an anti-CLL-1 antibody described herein. Also provided herein are vectors comprising an isolated nucleic acid encoding an anti-CLL-1 antibody described herein. Provided herein are also host cells comprising a vector comprising an isolated nucleic acid encoding an anti-CLL-1 antibody described herein. Also provided are methods of producing an anti-CLL-1 antibody described herein, the method comprising culturing a host cell comprising a vector comprising an isolated nucleic acid encoding an anti-CLL-1 antibody described herein in a culture medium.

In addition, provided herein are pharmaceutical compositions comprising an anti-CLL-1 antibody described herein.

In some embodiments of any of the anti-CLL-1 antibodies, the anti-CLL-1 antibody has a cell killing EC$_{50}$ of less than about 200 ng/mL, e.g., less than about any of 150, 100, 50, 25, 20, or 15 ng/mL. In some embodiments, the cell killing is human autologous CD14+. In some embodiments, the cell killing is cell line cell killing, e.g., U937 cell line, HL-60 cell line, PL-21 cell line, NOMO-1 cell line, EOL-1 cell line, THP-1 cell line, ML-2 cell line, Molm-13 cell line. In some embodiments of any of the multispecific anti-CLL-1 antibodies, the anti-CLL-1 antibody has a cytotoxic T cell activation EC$_{50}$ is less than about any of 50 ng/mL, e.g., less than about any of 25 ng/mL or 20 ng/mL. In some embodiments, cytotoxic T cell activation is measured by % of CD69+CD25+ T cells in CD8+ T cells.

Provided herein are anti-CLL-1 antibodies as described herein for use as a medicament. Provided herein are anti-CLL-1 antibody described herein for use in treating or delaying progression of a cell proliferative disorder or an autoimmune disorder in a subject in need thereof. Provided herein are anti-CLL-1 antibodies as described herein for use in enhancing immune function in a subject having a cell proliferative disorder or an autoimmune disorder. In some embodiments, the cell proliferative disorder is a cancer. In some embodiments, the cell proliferative disorder is acute myeloid leukemia (AML), chronic myeloid leukemia (CML), and/or myelodysplastic syndrome (MDS). In some embodiments, the cell proliferative disorder is CLL-1 positive. In some embodiments of any of the cell proliferative disorders, the cell proliferative disorder is resistant to treatment with an anti-AML antibody drug conjugate (e.g., anti-CLL1, anti-CD123, and/or anti-CD33 antibody drug conjugate). In some embodiments, the drug of the antibody drug conjugate is a DNA damaging agent (e.g., PBD).

Provided herein are uses of any of the anti-CLL-1 antibody described herein in the manufacture of a medicament for treating or delaying progression of a cell proliferative disorder or an autoimmune disorder. Provided herein are uses of any of the anti-CLL-1 antibody described herein in the manufacture of a medicament for enhancing immune function in a subject having a cell proliferative disorder or an autoimmune disorder. In some embodiments, the cell proliferative disorder is a cancer. In some embodiments, the cell proliferative disorder is AML, CML, and/or MDS. In some embodiments, the cell proliferative disorder is CLL-1 positive. In some embodiments of any of the cell proliferative disorders, the cell proliferative disorder is resistant to treatment with an anti-AML antibody drug conjugate (e.g., anti-CLL1, anti-CD123, and/or anti-CD33 antibody drug conjugate). In some embodiments, the drug of the antibody drug conjugate is a DNA damaging agent (e.g., PBD).

Provided herein are methods of treating or delaying the progression of a cell proliferative disorder or an autoimmune disorder in a subject in need thereof, the method comprising administering to the subject an anti-CLL-1 antibody described herein. Provided herein are methods of enhancing immune function in a subject having a cell proliferative disorder or an autoimmune disorder, the method comprising administering to the subject an effective amount of an anti-CLL-1 antibody described herein. In some embodiments, the cell proliferative disorder is a cancer. In some embodiments, the cell proliferative disorder is AML, CML, and/or MDS. In some embodiments, the cell proliferative disorder is CLL-1 positive. In some embodiments of any of the cell proliferative disorders, the cell proliferative disorder is resistant to treatment with an anti-AML antibody drug conjugate (e.g., anti-CLL1, anti-CD123, and/or anti-CD33 antibody drug conjugate). In some embodiments, the drug of the antibody drug conjugate is a DNA damaging agent (e.g., PBD).

In some embodiments of any of the methods, the anti-CLL-1 antibody binds to (a) a CD3 molecule located on an immune effector cell and (b) a CLL-1 molecule located on a cell. In some embodiments, the anti-CLL-1 antibody activates the immune effector cell following binding to (a) and (b). In some embodiments of any of the methods, the activated immune effector cell is capable of exerting a cytotoxic effect and/or an apoptotic effect on the target cell.

In some embodiments of any of the methods, the method further comprises administering to the subject a PD-1 axis binding antagonist or an additional therapeutic agent. In some embodiments, the PD-1 axis binding antagonist is a PD-1 binding antagonist. In some embodiments, the PD-1 axis binding antagonist is a PD-L1 binding antagonist. In some embodiments, the PD-1 axis binding antagonist is a PD-L2 binding antagonist.

In some embodiments of any of the methods, the method further comprises administering to the subject a glucocorticoid. In some embodiments, the glucocorticoid is dexamethasone.

In some embodiments of any of the methods, the method is used in combination with stem cell transplant.

In some embodiments of any of the methods, the method further comprises administering to the subject a second therapeutic agent. In some embodiments, the second therapeutic agent comprises cytarabine and/or daunorubicin. In some embodiments, the second therapeutic agent comprises cytarabine. In some embodiments, the second therapeutic agent comprises an anti-AML antibody drug conjugate (e.g., anti-CLL1, anti-CD123, and/or anti-CD33 antibody drug conjugate).

BRIEF DESCRIPTION OF THE FIGURES

FIG. 1A-B shows alignment of the light chain variable region sequences (SEQ ID NOS 30, 37, 35 and 41, respectively, in order of appearance) (A) and heavy chain variable region sequences (SEQ ID NOS 31, 38, 36 and 42, respectively, in order of appearance) (B) of murine (m) 6E7, m21C9, m20B1, and m28H12.

FIG. 2A-B shows alignment of the light chain variable region sequences (SEQ ID NOS 109, 30, 32 and 32, respectively, in order of appearance) (A) and heavy chain variable region sequences (SEQ ID NOS 110, 31, 33 and 34, respectively, in order of appearance) (B) of K1H1, m6E7, humanized (h) 6E7.L4H1e, and h6E7.L4H1e.A54.

FIG. 3A-B shows alignment of the light chain variable region sequences (SEQ ID NOS 109, 37 and 39, respectively, in order of appearance) (A) and heavy chain variable region sequences (SEQ ID NOS 110, 38 and 40, respectively, in order of appearance) (B) of K1H1, m21C9, and h21C9.L2H3.

FIG. 8A-D shows in vitro characterization of anti-gDx38E4v1 control, anti-CLL-1 TDBs with low affinity CD3 arm (h6E7 (6E7.L4H1e)x40G5c), high affinity anti-CD3 arm (h6E7 (6E7.L4H1e)x38E4v1), and very high affinity anti-CD3 arm (h6E7 (6E7.L4H1e)x38E4v11) using HL60, THP-1, and EOL-1 cell lines).

FIG. 8E-G shows in vitro characterization of variants of h6E7.L4H1e N54-A or -S or -E or -Q or -D humanized Fab paired with low affinity anti-CD3 Fab (h40G5c) or high affinity anti-CD3 Fab (38E4v1).

Figure 16B:
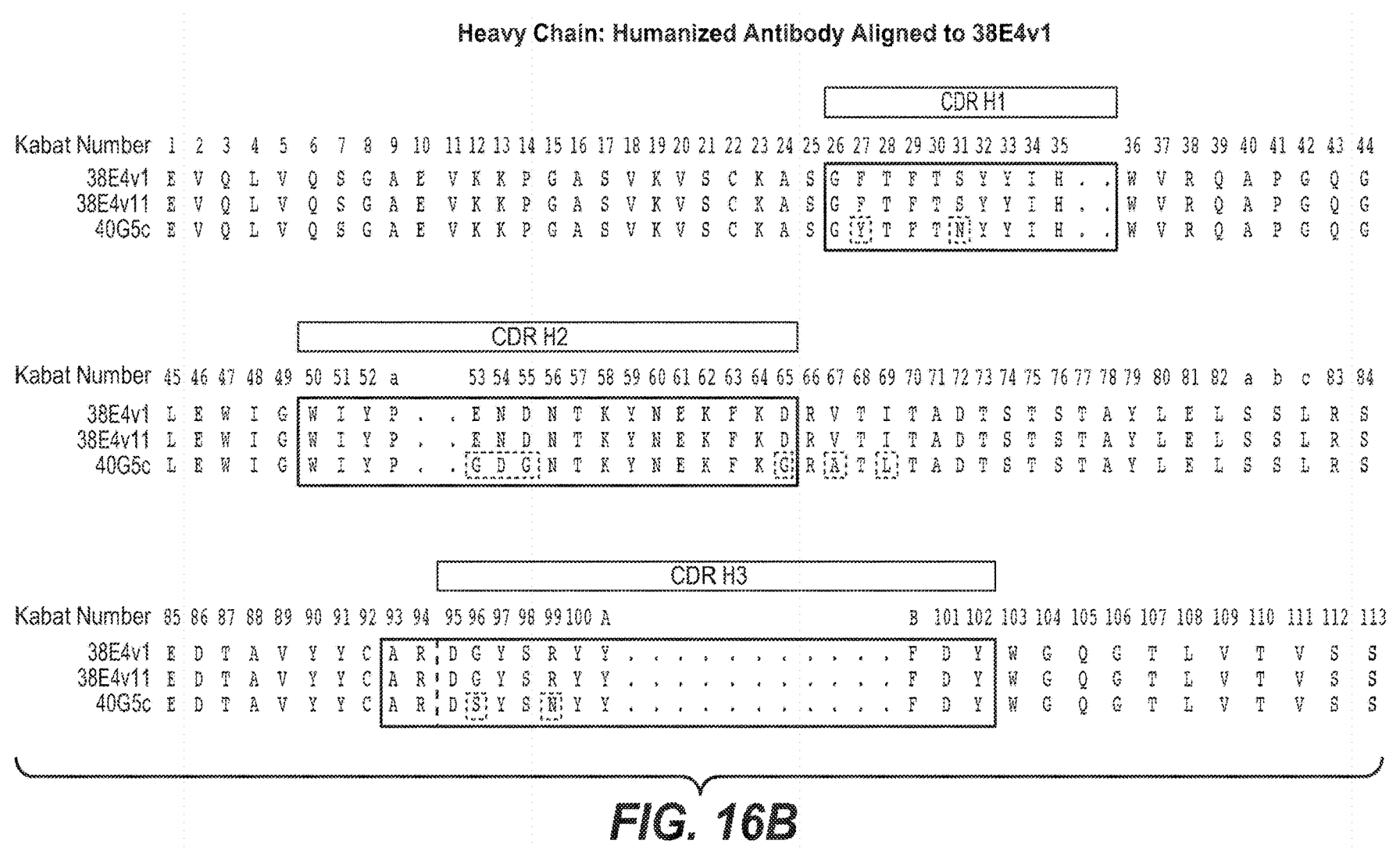

FIG. 16A-B shows alignment of the light chain variable region sequences (SEQ ID NOS 85, 93 and 83, respectively, in order of appearance) (A) and heavy chain variable region sequences (SEQ ID NOS 84, 84 and 82, respectively, in order of appearance) (B) of 38E4v1, 38E4v11, and 40G5C.

FIG. 22A-B shows myeloid cell reduction in hCLL-1/hCD3e BAC-Tg mice treated with h6E7N54A (6E7.L4H1eA54)xh40G5c and anti-PD-L1.

DETAILED DESCRIPTION OF EMBODIMENTS OF THE INVENTION

I. Definitions

Figure 4A:
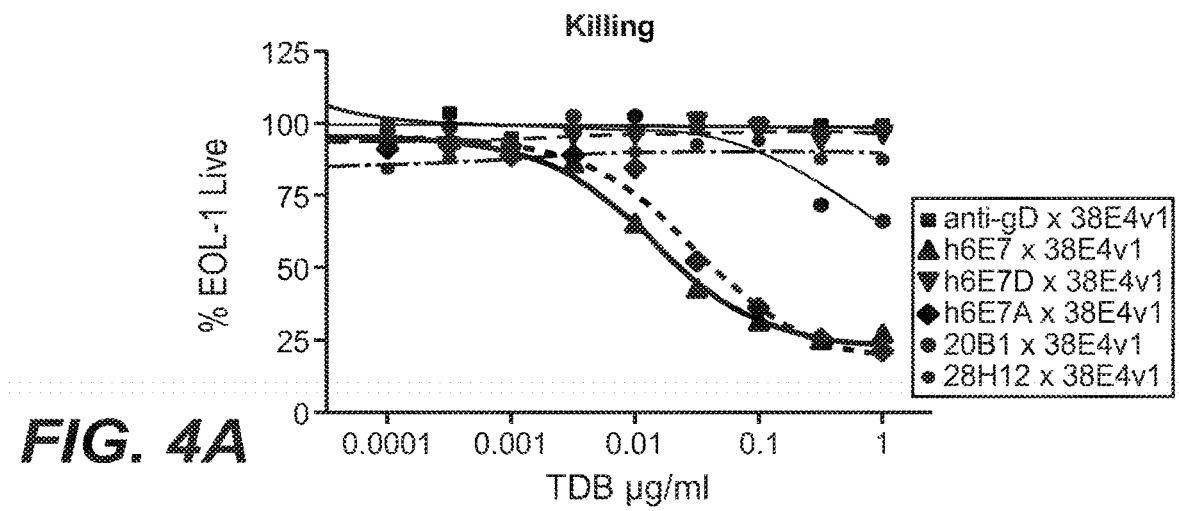
FIG. 4A-C shows in vitro killing characterization of anti-CLL-1/CD3 TDBs. (A) shows percent killing of EOL-1 at various concentrations of TDB, μg/mL, (gD, h6E7 (6E7.L4H1e), h6E7D (6E7.L4H1eD54), h6E7A (6E7.L4H1eA54), m20B1, and m28H12 in combination with 38E4v1). (B) and (C) show percent cell killing (PBMC, EOL-1, and THP-1) and CD8 (CD8+, CD69+, CD25+) T cell activation, respectively, using gD, 6E7 (6E7.L4H1e), and h21C9 (h21C9.L2H3) in combination with 38E4v1 at various concentrations of TDBs (μg/mL).

The term "CLL-1," as used herein, refers to any native, mature CLL-1 which results from processing of a CLL-1 precursor protein in a cell. The term includes CLL-1 from any vertebrate source, including mammals such as primates (e.g. humans and cynomolgus monkeys) and rodents (e.g., mice and rats), unless otherwise indicated. The term also includes naturally occurring variants of CLL-1, e.g., splice variants or allelic variants. The amino acid sequence of an exemplary human CLL-1 protein sequence is shown in SEQ ID NO:1. In some embodiments, the human CLL-1 protein sequence comprises the K244Q SNP (SEQ ID NO:1, wherein K244 is Q). The amino acid sequence of an exemplary extracellular domain is the amino acids of SEQ ID NO:2. The amino acid sequence of an exemplary C-type lectin like domain (CTLD) is the amino acids of SEQ ID NO:3. The amino acid sequence of an exemplary cynomolgus monkey CLL-1 protein is shown in SEQ ID NO:4.

The term "glycosylated forms of CLL-1" refers to naturally occurring forms of CLL-1 that are post-translationally modified by the addition of carbohydrate residues.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The terms "anti-CLL-1 antibody" and "an antibody that binds to CLL-1" refer to an antibody that is capable of binding CLL-1 with sufficient affinity such that the antibody is useful as a diagnostic and/or therapeutic agent in targeting CLL-1. In one embodiment, the extent of binding of an anti-CLL-1 antibody to an unrelated, non-CLL-1 protein is less than about 10% of the binding of the antibody to CLL-1 as measured, e.g., by a radioimmunoassay (RIA). In certain embodiments, an antibody that binds to CLL-1 has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g. from $10^{-8}$M to $10^{-13}$ M, e.g., from $10^{-9}$M to $10^{-13}$ M). In certain embodiments, an anti-CLL-1 antibody binds to an epitope of CLL-1 that is conserved among CLL-1 from different species.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of ≤1 µM, ≤100 nM, ≤10 nM, ≤1 nM, ≤0.1 nM, ≤0.01 nM, or ≤0.001 nM (e.g., 10 M or less, e.g., from $10^{-8}$M to $10^{-13}$M, e.g., from $10^{-9}$M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

The term "epitope" refers to the particular site on an antigen molecule to which an antibody binds. In some embodiments, the particular site on an antigen molecule to which an antibody binds is determined by hydroxyl radical footprinting (e.g., CLL-1 binding domain). In some embodiments, the particular site on an antigen molecule to which an antibody binds is determined by crystallography (e.g., CD3 binding domain).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors; and B cell activation.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ u and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CLL-1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D.

All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "effective amount" of an agent, e.g., a pharmaceutical formulation, refers to an amount effective, at dosages and for periods of time necessary, to achieve the desired therapeutic or prophylactic result. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serinethreonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor downregulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; laneway, Nature, 341: 482 (1989); and WO 91/01133); BAFF antagonists such as BAFF antibodies and BR3 antibodies and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10139. Some preferred immunosuppressive agents herein include cyclophosphamide, chlorambucil, azathioprine, leflunomide, MMF, or methotrexate.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A (CAS Registry Number 1380723-44-3) described herein. In still another specific aspect, an anti-PD-L1 antibody is MED14736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

The terms "cell proliferative disorder" and "proliferative disorder" refer to disorders that are associated with some degree of abnormal cell proliferation. In one embodiment, the cell proliferative disorder is cancer.

The terms "cancer" and "cancerous" refer to or describe the physiological condition in mammals that is typically characterized by unregulated cell growth/proliferation. In some embodiments, the cancer is a CLL-1 positive cancer. Examples of cancer including CLL-1 positive cancers include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "CLL-1-positive cell" refers to a cell that expresses CLL-1 on its surface.

The term "CLL-1-positive cancer" refers to a cancer comprising cells that express CLL-1 on their surface. In some embodiments, expression of CLL-1 on the cell surface is determined, for example, using antibodies to CLL-1 in a method such as immunohistochemistry, FACS, etc. Alternatively, CLL-1 mRNA expression is considered to correlate to CLL-1 expression on the cell surface and can be determined by a method selected from in situ hybridization and RT-PCR (including quantitative RT-PCR).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting of" and/or "consisting essentially of" aspects and variations.

II. Compositions and Methods

In one aspect, the invention is based, in part, on anti-CLL-1 antibodies. In certain embodiments, the anti-CLL-1 antibodies comprising a CLL-1 binding domain and a CD3 binding domain are provided. In certain embodiments, the anti-CLL-1 antibodies are anti-CLL-1 T cell dependent bispecific (TDB) antibodies. Antibodies of the invention are useful, e.g., for the diagnosis or treatment of cancer such as acute myeloid leukemia (AML).

A. Exemplary Anti-CLL-1 Antibodies

The invention provides anti-CLL-1 antibodies comprising a CLL-1 binding domain and a CD3 binding domain and methods of using the same. In some embodiments, provided herein are isolated anti-CLL-1 antibodies, wherein the antibody comprises (i) a CLL-1 binding domain, wherein the CLL-1 binding domain binds a CLL-1 epitope and/or binds an overlapping CLL-1 epitope comprising amino acids of SEQ ID NO:49 and does not bind an epitope comprising SEQ ID NO:50 and/or SEQ ID NO:51; and (ii) a CD3 binding domain, wherein the CD3 binding domain binds a human CD3ε polypeptide and a cyno CD3ε polypeptide, the CD3 binding domain binds to a CD3 epitope within a fragment of the human CD3ε polypeptide consisting of amino acids 1-26 (SEQ ID NO:86) or 1-27 (SEQ ID NO:87) of human CD3ε, and amino acid residue Glu5 of the human CD3ε polypeptide is not required for binding of the CD3 binding domain.

a) CLL-1 Binding Domains of Anti-CLL1 Antibodies

In some embodiments, the CLL-1 binding domain of the anti-CLL-1 antibody binds a CLL-1 epitope and/or binds a CLL-1 overlapping epitope comprising amino acids of SEQ ID NO:49 and does not bind a CLL-1 epitope comprising SEQ ID NO:50 and/or SEQ ID NO:51. In some embodiments, the CLL-1 binding domain of the anti-CLL-1 antibody binds a CLL-1 epitope comprising amino acids of SEQ ID NO:49. In some embodiments, the CLL-1 binding domain of the anti-CLL-1 antibody binds a CLL-1 epitope consisting or consisting essentially of the amino acids of SEQ ID NO:49. In some embodiments, the CLL-1 epitope is determined by hydroxyl radical footprinting. In some embodiments, the CLL-1 epitope as determined by hydroxyl radical footprinting has a ratio of [rate constant of the antigen]/[rate constant of the antigen and antibody complex] greater than about any of 1.8, 1.9, 2.0, 2.1, 2.2, 2.3, 2.4, 2.5, 2.6, 2.7, 2.8, 2.9, or 3.0. In some embodiments, the a CLL-1 epitope as determined by hydroxyl radical footprinting has a ratio of [rate constant of the antigen]/[rate constant of the antigen and antibody complex] greater than about 2.0.

Hydroxyl radical footprinting may be performed as described in the Examples. For example, samples are exposed to hydroxyl radicals for intervals of 0, 10, 15, and 20 milliseconds (ms) using the X28c Beam line at the Brookhaven National Laboratory. The labeled samples may be subjected to deglycosylation using PNGase F. The samples may be precipitated using Trichloroacetic acid in acetone, and subjected to LC-MS analysis. The samples may be then subjected to reduction and alkylation, digestion using Trypsin, followed by liquid chromatography coupled with high-resolution mass spectrometry (LC-MS). The MS data may be analyzed using ProtMapMS, resulting in dose response plots for each peptide. Results from the free antigen may be compared against each of the complex forms. A homology-based model of the antigen may be generated using Swiss-Model software, and the solvent protected regions may be mapped for each of the three complexes. The selected ion chromatograms (SIC) may be extracted and integrated for the unoxidized and all oxidized forms of peptide ion (with particular m/z). These peak area values may be used to characterize reaction kinetics in the form of dose response (DR) plots, which measure the loss of intact peptide as a function of the hydroxyl radical exposure. The solvent protected regions in the complex experience gradual oxidation reaction as opposed to the free antigen, and the differences in the rate of oxidation (called rate constant, RC) may serve to highlight the location of the epitope (e.g., CLL-1 epitope).

In some embodiments of any of the anti-CLL1 antibodies, the CLL-1 binding domain binds to recombinant human CLL-1. In some embodiments of any of the anti-CLL1 antibodies, the CLL-1 binding domain binds to recombinant cynomolgus monkey CLL-1. In some embodiments of any of the anti-CLL1 antibodies, the CLL-1 binding domain binds to endogenous CLL-1 on the surface of human peripheral blood mononucleocytes (PBMCs). In some embodiments of any of the anti-CLL1 antibodies, the CLL-1 binding domain binds to endogenous CLL-1 on the surface of cynomolgus monkey PBMCs. In some embodiments of any of the anti-CLL1 antibodies, the CLL-1 binding domain binds to endogenous CLL-1 on the surface of a cancer cell. In some embodiments of any of the anti-CLL1 antibodies, the CLL-1 binding domain binds to endogenous CLL-1 on the surface of an AML cancer cell. In some embodiments of any of the anti-CLL1 antibodies, the CLL-1 binding domain binds to endogenous CLL-1 on the surface of HL-60 cells. In some embodiments of any of the anti-CLL1 antibodies, the CLL-1 binding domain binds to endogenous CLL-1 on the surface of EOL-1 cells. In some embodiments of any of the anti-CLL1 antibodies, the CLL-1 binding domain binds to CLL-1 comprising a K244Q mutation (SEQ ID NO:1 with K244Q). In some embodiments of any of the anti-CLL1 antibodies, the CLL-1 binding domain binds a CLL-1 epitope and/or binds an overlapping CLL-1 epitope comprising amino acids of SEQ ID NO:49. In some embodiments of any of the anti-CLL1 antibodies, the CLL-1 binding domain does not bind a CLL-1 epitope comprising SEQ ID NO:50 and/or SEQ ID NO:51. In some embodiments of any of the anti-CLL1 antibodies, the CLL-1 binding domain competes for human CLL-1 binding with R&D System Clone 687317 antibody. In some embodiments of any of the anti-CLL1 antibodies, the CLL-1 binding domain binds to endogenous human CLL-1 with a Kd of less than 15 nM, less than 10 nM, less than 7 nM, less than 5 nM, or less than 3 nM. In some embodiments of any of the anti-CLL1 antibodies, the CLL-1 binding domain binds to recombinant human CLL-1 with a Kd of less than 10 nM, less than 7 nM, less than 5 nM, or less than 3 nM. In some embodiments of any of the anti-CLL1 antibodies, the CLL-1 binding domain binds to recombinant cynomolgus monkey CLL-1 with a Kd of less than 10 nM, less than 7 nM, less than 5 nM, or less than 3 nM, less than 2 nM, or less than 1 nM. In some embodiments, the Kd is determined by any method described herein, in particular the examples. In some embodiments, Kd is determined by BIACORE. In some embodiments, Kd is determined by CLL-1 immobilized at a low density.

In some embodiments of any of the anti-CLL-1 antibodies, the anti-CLL-1 antibody has a cell killing $EC_{50}$ of less than about 200 ng/mL, e.g., less than about any of 150, 100, 50, 25, 20, or 15 ng/mL. In some embodiments, the cell killing is human autologous CD14+. In some embodiments, the cell killing is cell line cell killing, e.g., U937 cell line, HL-60 cell line, PL-21 cell line, NOMO-1 cell line, EOL-1 cell line, THP-1 cell line, ML-2 cell line, Molm-13 cell line. In some embodiments of any of the multispecific anti-CLL-1 antibodies, the anti-CLL-1 antibody has a cytotoxic T cell activation $EC_{50}$ is less than about any of 50 ng/mL, e.g., less than about any of 25 ng/mL or 20 ng/mL. In some embodiments, cytotoxic T cell activation is measured by % of CD69+CD25+ T cells in CD8+ T cells.

In some embodiments, the characteristics of the CLL-1 binding domain and/or CLL-1 antibody are determined as described herein in the Examples below.

CLL-1 Binding Domain 6E7 and Other Embodiments

In some embodiments of any of the CLL-1 antibodies, the invention provides an anti-CLL-1 antibody comprising a CLL-1 binding domain comprising at least one, two, three, four, five, or six HVRs selected from (a) HVR-H1 comprising the amino acid sequence of SEQ ID NO:8; (b) HVR-H2 comprising the amino acid sequence of SEQ ID NO:45; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In one aspect, the invention provides an anti-CLL-1 antibody comprising a CLL-1 binding domain comprising at least one, at least two, or all three VH HVR sequences selected from (a) HVR-H1 comprising the amino acid sequence of SEQ ID NO:8; (b) HVR-H2 comprising the amino acid sequence of SEQ ID NO:45; and (c) HVR-H3 comprising the amino acid sequence of SEQ ID NO:10. In one embodiment, the CLL-1 binding domain comprises HVR-H3 comprising the amino acid sequence of SEQ ID NO:10. In another embodiment, the CLL-1 binding domain comprises HVR-H3 comprising the amino acid sequence of SEQ ID NO:10 and HVR-L3 comprising the amino acid sequence of SEQ ID NO:7. In a further embodiment, the CLL-1 binding domain comprises HVR-H3 comprising the amino acid sequence of SEQ ID NO:10, HVR-L3 comprising the amino acid sequence of SEQ ID NO:7, and HVR-H2 comprising the amino acid sequence of SEQ ID NO:45. In a further embodiment, the CLL-1 binding domain comprises (a) HVR-H1 comprising the amino acid sequence of SEQ ID NO:8; (b) HVR-H2 comprising the amino acid sequence of SEQ ID NO:45; and (c) HVR-H3 comprising the amino acid sequence of SEQ ID NO:10. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In another aspect, the invention provides an anti-CLL-1 antibody comprising a CLL-1 binding domain comprising at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the CLL-1 binding domain comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-CLL-1 antibody comprising a CLL-1 binding domain comprising (a) a VH domain comprising at least one, at least two, or all three VH HVR sequences selected from (i) HVR-H1 comprising the amino acid sequence of SEQ ID NO:8, (ii) HVR-H2 comprising the amino acid sequence of SEQ ID NO:45, and (iii) HVR-H3 comprising an amino acid sequence selected from SEQ ID NO:10; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In another aspect, the invention provides an anti-CLL-1 antibody comprising a CLL-1 binding domain comprising (a) HVR-H1 comprising the amino acid sequence of SEQ ID NO:8; (b) HVR-H2 comprising the amino acid sequence of SEQ ID NO:45; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:9; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the CLL-1 binding domain comprises (a) HVR-H1 comprising the amino acid sequence of SEQ ID NO:8; (b) HVR-H2 comprising the amino acid sequence of SEQ ID NO:47; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the CLL-1 binding domain comprises (a) HVR-H1 comprising the amino acid sequence of SEQ ID NO:8; (b) HVR-H2 comprising the amino acid sequence of SEQ ID NO:11; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the CLL-1 binding domain comprises (a) HVR-H1 comprising the amino acid sequence of SEQ ID NO:8; (b) HVR-H2 comprising the amino acid sequence of SEQ ID NO:43; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the CLL-1 binding domain comprises (a) HVR-H1 comprising the amino acid sequence of SEQ ID NO:8; (b) HVR-H2 comprising the amino acid sequence of SEQ ID NO:44; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In any of the above embodiments, an anti-CLL-1 antibody comprising a CLL-1 binding domain is humanized. In one embodiment, an anti-CLL-1 antibody comprising a CLL-1 binding domain comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CLL-1 antibody comprising a CLL-1 binding domain comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:31, SEQ ID NO:33, SEQ ID NO:34, SEQ ID NO:46 and/or SEQ ID NO:48. In certain embodiments, a VH sequence having at least 90%, 91%, 92%, 93%, 94%, 95%, 96%, 97%, 98%, or 99% identity to the amino acid sequence of SEQ ID NO:31, SEQ ID NO:33, SEQ ID NO:34, SEQ ID NO:46 and/or SEQ ID NO:48 contains substitutions (e.g., conservative substitutions), insertions, or deletions relative to the reference sequence, but a CLL-1 binding domain comprising that sequence retains the ability to bind to CLL-1. In certain embodiments, a total of 1 to 10 amino acids have been substituted, inserted and/or deleted in SEQ ID NO:31, SEQ ID NO:33, SEQ ID NO:34, SEQ ID NO:46 and/or SEQ ID NO:48. In certain embodiments, a total of 1 to 5 amino acids have been substituted, inserted and/or deleted in SEQ ID NO:31, SEQ ID NO:33, SEQ ID NO:34, SEQ ID NO:46 and/or SEQ ID NO:48. In certain embodiments, substitutions, insertions, or deletions occur in regions outside the HVRs (i.e., in the FRs). Optionally, the anti-CLL-1 antibody comprising the CLL-1 binding domain comprises the VH sequence of SEQ ID NO:31, SEQ ID NO:33, and/or SEQ ID NO:34, including post-translational modifications of that sequence. In a particular embodiment, the VH comprises one, two or three HVRs selected from: (a) HVR-H1 comprising the amino acid sequence of SEQ ID NO:8, (b) HVR-H2 comprising the amino acid sequence of SEQ ID NO:45, and (c) HVR-H3 comprising the amino acid sequence of SEQ ID NO:10. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In another aspect, an anti-CLL-1 antibody comprising a CLL-1 binding domain is provided, wherein the CLL-1 binding domain comprises a light chain variable domain (VL) having at least 90%, 91%, 92%, 93%, 94%, 95%, 96%, 97%, 98%, 99%, or 100% sequence identity to the amino acid sequence of SEQ ID NO:30 and/or SEQ ID NO:32. In certain embodiments, a VL sequence having at least 90%, 91%, 92%, 93%, 94%, 95%, 96%, 97%, 98%, or 99% identity to the amino acid sequence of SEQ ID NO:30 and/or SEQ ID NO:32 contains substitutions (e.g., conservative substitutions), insertions, or deletions relative to the reference sequence, but a CLL-1 binding domain comprising that sequence retains the ability to bind to CLL-1. In certain embodiments, a total of 1 to 10 amino acids have been substituted, inserted and/or deleted in SEQ ID NO:30 and/or SEQ ID NO:32. In certain embodiments, a total of 1 to 5 amino acids have been substituted, inserted and/or deleted in SEQ ID NO:30 and/or SEQ ID NO:32. In certain embodiments, the substitutions, insertions, or deletions occur in regions outside the HVRs (i.e., in the FRs). Optionally, the anti-CLL-1 antibody comprising the CLL-1 binding domain comprises the VL sequence of SEQ ID NO:30 and/or SEQ ID NO:32, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-CLL-1 antibody comprising a CLL-1 binding domain is provided, wherein the CLL-1 binding domain comprises a VH as in any of the embodiments provided above, and a VL as in any of the embodiments provided above.

In one embodiment, the CLL-1 binding domain comprises the VH and VL sequences in SEQ ID NO:31 and SEQ ID NO:30, respectively, including post-translational modifications of those sequences. In one embodiment, the CLL-1 binding domain comprises the VH and VL sequences in SEQ ID NO:33 and SEQ ID NO:32, respectively, including post-translational modifications of those sequences. In one embodiment, the CLL-1 binding domain comprises the VH and VL sequences in SEQ ID NO:34 and SEQ ID NO:32, respectively, including post-translational modifications of those sequences. In one embodiment, the CLL-1 binding domain comprises the VH and VL sequences in SEQ ID NO:46 and SEQ ID NO:32, respectively, including post-translational modifications of those sequences. In one embodiment, the CLL-1 binding domain comprises the VH and VL sequences in SEQ ID NO:48 and SEQ ID NO:32, respectively, including post-translational modifications of those sequences.

In a further aspect, provided are herein are antibodies that bind to the same epitope as CLL-1 binding domain provided herein. For example, in certain embodiments, an antibody is provided that binds to the same epitope as a CLL-1 binding domain comprising a VH sequence of SEQ ID NO:31, SEQ ID NO:33, SEQ ID NO:34, SEQ ID NO:46 and/or SEQ ID NO:48 and a VL sequence of SEQ ID NO:30 and/or SEQ ID NO:32, respectively.

Figure 2A:
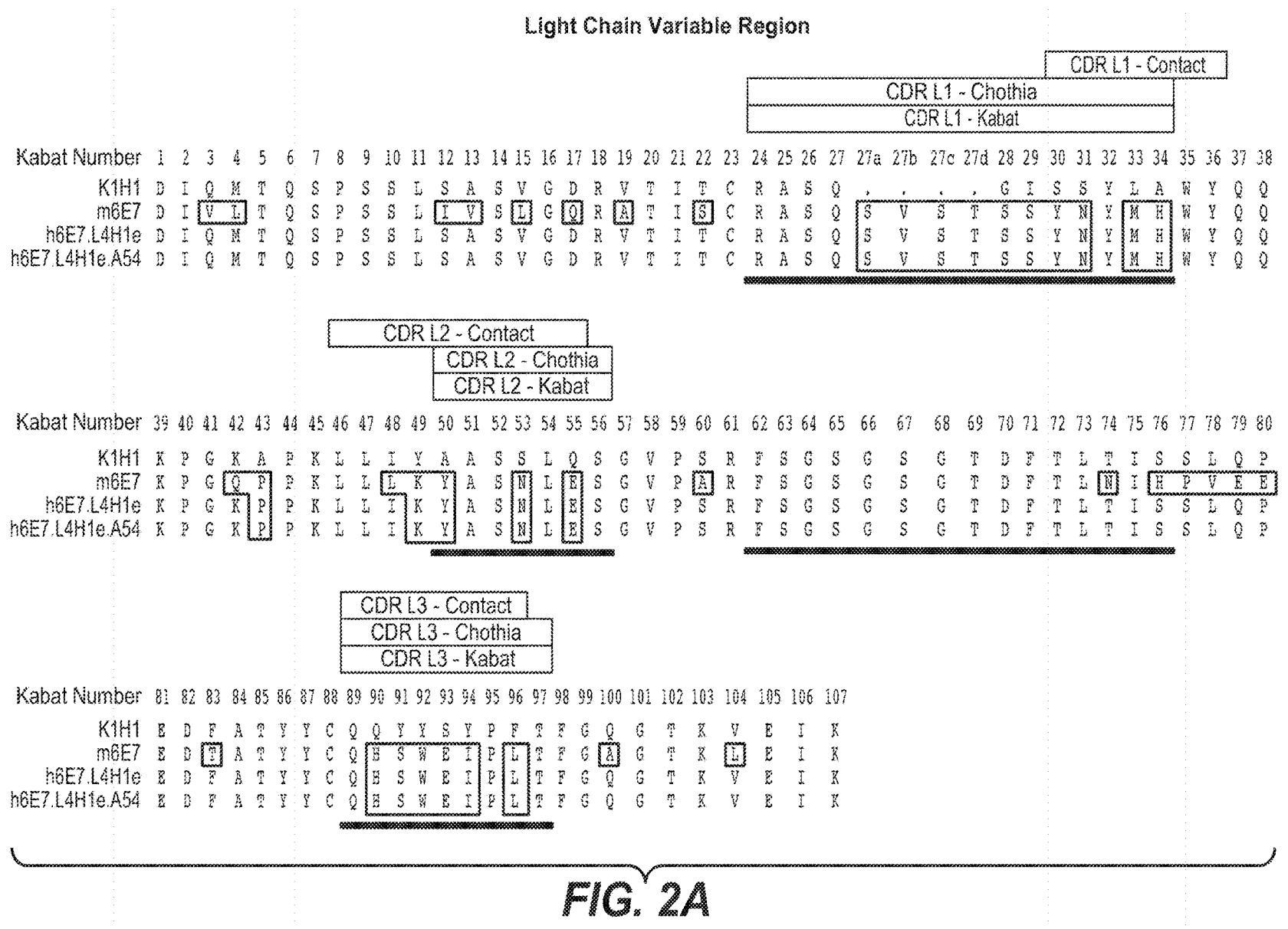
Figure 2B:
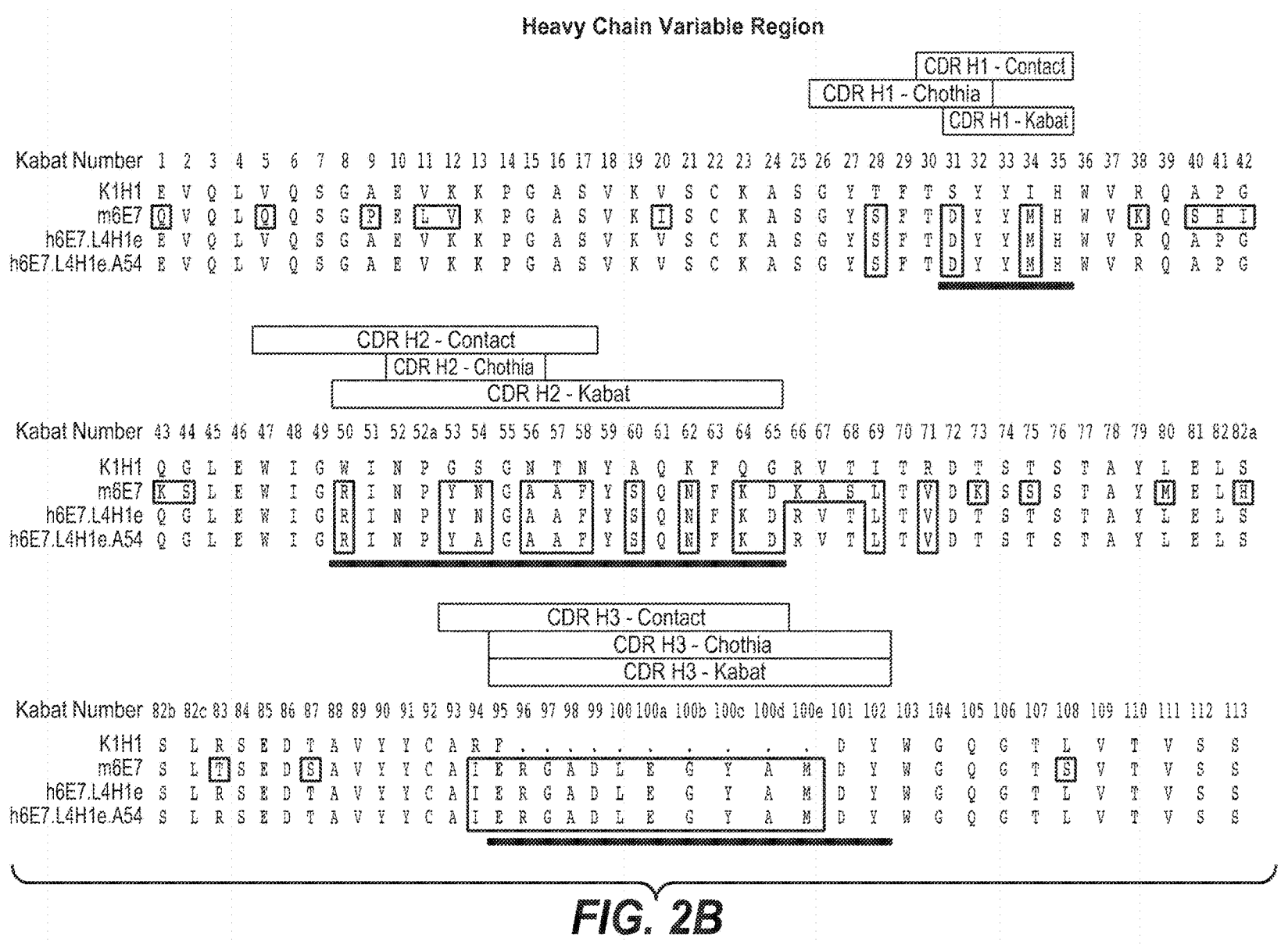

Provided herein are an anti-CLL-1 antibodies comprising a CLL-1 binding domain comprising a light chain variable domain comprising the HVR1-LC, HVR2-LC and HVR3-LC sequence according to Kabat numbering as depicted in FIG. 2A and a heavy chain variable domain comprising the HVR1-HC, HVR2-HC and HVR3-HC sequence according to Kabat numbering as depicted in FIG. 2B. In some embodiments, the anti-CLL-1 antibody comprising the CLL-1 binding domain comprises a light chain variable domain comprising the HVR1-LC, HVR2-LC and/or HVR3-LC sequence, and the FR1-LC, FR2-LC, FR3-LC and/or FR4-LC sequence as depicted in FIG. 2A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 2B.

In a further aspect of the invention, an anti-CLL-1 antibody comprising a CLL-1 binding domain according to any of the above embodiments is a monoclonal antibody, including a human antibody. In one embodiment, an anti-CLL-1 antibody comprising a CLL-1 binding domain is an antibody fragment, e.g., a Fv, Fab, Fab', scFv, diabody, or F(ab')$_2$ fragment. In another embodiment, the anti-CLL-1 antibody comprising a CLL-1 binding domain is a substantially full length antibody, e.g., an IgG1 antibody, IgG2a antibody or other antibody class or isotype as defined herein.

CLL-1 Binding Domain 21C9 and Other Embodiments

In some embodiments, the invention provides an anti-CLL-1 antibody comprising a CLL-1 binding domain comprising at least one, two, three, four, five, or six HVRs selected from (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20.

In one aspect, the invention provides an anti-CLL-1 antibody comprising a CLL-1 binding domain comprising at least one, at least two, or all three VH HVR sequences selected from (a) HVR-H1 comprising the amino acid sequence of SEQ ID NO:21; (b) HVR-H2 comprising the amino acid sequence of SEQ ID NO:22; and (c) HVR-H3 comprising the amino acid sequence of SEQ ID NO:23. In one embodiment, the CLL-1 binding domain comprises HVR-H3 comprising the amino acid sequence of SEQ ID NO:23. In another embodiment, the CLL-1 binding domain comprises HVR-H3 comprising the amino acid sequence of SEQ ID NO:23 and HVR-L3 comprising the amino acid sequence of SEQ ID NO:20. In a further embodiment, the CLL-1 binding domain comprises HVR-H3 comprising the amino acid sequence of SEQ ID NO:23, HVR-L3 comprising the amino acid sequence of SEQ ID NO:20, and HVR-H2 comprising the amino acid sequence of SEQ ID NO:22. In a further embodiment, the CLL-1 binding domain comprises (a) HVR-H1 comprising the amino acid sequence of SEQ ID NO:21; (b) HVR-H2 comprising the amino acid sequence of SEQ ID NO:22; and (c) HVR-H3 comprising the amino acid sequence of SEQ ID NO:23.

In another aspect, the invention provides an anti-CLL-1 antibody comprising a CLL-1 binding domain comprising at least one, at least two, or all three VL HVR sequences selected from (a) HVR-L1 comprising the amino acid sequence of SEQ ID NO:18; (b) HVR-L2 comprising the amino acid sequence of SEQ ID NO:19; and (c) HVR-L3 comprising the amino acid sequence of SEQ ID NO:20. In one embodiment, the CLL-1 binding domain comprises (a) HVR-L1 comprising the amino acid sequence of SEQ ID NO:18; (b) HVR-L2 comprising the amino acid sequence of SEQ ID NO:19; and (c) HVR-L3 comprising the amino acid sequence of SEQ ID NO:20.

In another aspect, an anti-CLL-1 antibody comprising a CLL-1 binding domain of the invention comprises (a) a VH domain comprising at least one, at least two, or all three VH HVR sequences selected from (i) HVR-H1 comprising the amino acid sequence of SEQ ID NO:21, (ii) HVR-H2 comprising the amino acid sequence of SEQ ID NO:22, and (iii) HVR-H3 comprising an amino acid sequence selected from SEQ ID NO:23; and (b) a VL domain comprising at least one, at least two, or all three VL HVR sequences selected from (i) HVR-L1 comprising the amino acid sequence of SEQ ID NO:18, (ii) HVR-L2 comprising the amino acid sequence of SEQ ID NO:19, and (c) HVR-L3 comprising the amino acid sequence of SEQ ID NO:20.

In another aspect, the invention provides an anti-CLL-1 antibody comprising a CLL-1 binding domain comprising (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20. In some embodiments, the antibody comprises (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20.

In any of the above embodiments, an anti-CLL-1 antibody comprising a CLL-1 binding domain is humanized. In one embodiment, an anti-CLL-1 antibody comprising a CLL-1 binding domain comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CLL-1 antibody comprising a CLL-1 binding domain comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:38 and/or SEQ ID NO:40. In certain embodiments, a VH sequence having at least 90%, 91%, 92%, 93%, 94%, 95%, 96%, 97%, 98%, or 99% identity to the amino acid sequence of SEQ ID NO:38 and/or SEQ ID NO:40 contains substitutions (e.g., conservative substitutions), insertions, or deletions relative to the reference sequence, but a CLL-1 binding domain comprising that sequence retains the ability to bind to CLL-1. In certain embodiments, a total of 1 to 10 amino acids have been substituted, inserted and/or deleted in SEQ ID NO:38 and/or SEQ ID NO:40. In certain embodiments, a total of 1 to 5 amino acids have been substituted, inserted and/or deleted in SEQ ID NO:38 and/or SEQ ID NO:40. In certain embodiments, substitutions, insertions, or deletions occur in regions outside the HVRs (i.e., in the FRs). Optionally, the anti-CLL-1 antibody comprising a CLL-1 binding domain comprises the VH sequence of SEQ ID NO:38 and/or SEQ ID NO:40, including post-translational modifications of that sequence. In a particular embodiment, the VH comprises one, two or three HVRs selected from: (a) HVR-H1 comprising the amino acid sequence of SEQ ID NO:21, (b) HVR-H2 comprising the amino acid sequence of SEQ ID NO:22, and (c) HVR-H3 comprising the amino acid sequence of SEQ ID NO:23.

In another aspect, an anti-CLL-1 antibody comprising a CLL-1 binding domain is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:37 and/or SEQ ID NO:39. In certain embodiments, a VL sequence having at least 90%, 91%, 92%, 93%, 94%, 95%, 96%, 97%, 98%, or 99% identity to the amino acid sequence of SEQ ID NO:37 and/or SEQ ID NO:39 contains substitutions (e.g., conservative substitutions), insertions, or deletions relative to the reference sequence, but a CLL-1 binding domain comprising that sequence retains the ability to bind to CLL-1. In certain embodiments, a total of 1 to 10 amino acids have been substituted, inserted and/or deleted in SEQ ID NO:37 and/or SEQ ID NO:39. In certain embodiments, a total of 1 to 5 amino acids have been substituted, inserted and/or deleted in SEQ ID NO:37 and/or SEQ ID NO:39. In certain embodiments, the substitutions, insertions, or deletions occur in regions outside the HVRs (i.e., in the FRs). Optionally, the anti-CLL-1 antibody comprising a CLL-1 binding domain comprises the VL sequence of SEQ ID NO:37 and/or SEQ ID NO:39, including post-translational modifications of that sequence. In a particular embodiment, the VL comprises one, two or three HVRs selected from (a) HVR-L1 comprising the amino acid sequence of SEQ ID NO:18; (b) HVR-L2 comprising the amino acid sequence of SEQ ID NO:19; and (c) HVR-L3 comprising the amino acid sequence of SEQ ID NO:20.

In another aspect, an anti-CLL-1 antibody comprising a CLL-1 binding domain is provided, wherein the antibody comprises a VH as in any of the embodiments provided above, and a VL as in any of the embodiments provided above.

In one embodiment, the anti-CLL-1 antibody comprising a CLL-1 binding domain comprises the VH and VL sequences in SEQ ID NO:38 and SEQ ID NO:37, respectively, including post-translational modifications of those sequences. In one embodiment, the antibody comprises the VH and VL sequences in SEQ ID NO:40 and SEQ ID NO:39, respectively, including post-translational modifications of those sequences.

In a further aspect, provided are herein are anti-CLL-1 antibody comprising a CLL-1 binding domain that bind to the same epitope as an anti-CLL-1 antibody provided herein. For example, in certain embodiments, an antibody is provided that binds to the same epitope as an anti-CLL-1 antibody comprising a CLL-1 binding domain comprising a VH sequence of SEQ ID NO:38 and/or SEQ ID NO:40 and a VL sequence of SEQ ID NO:37 and/or SEQ ID NO:39, respectively.

Figure 3A:
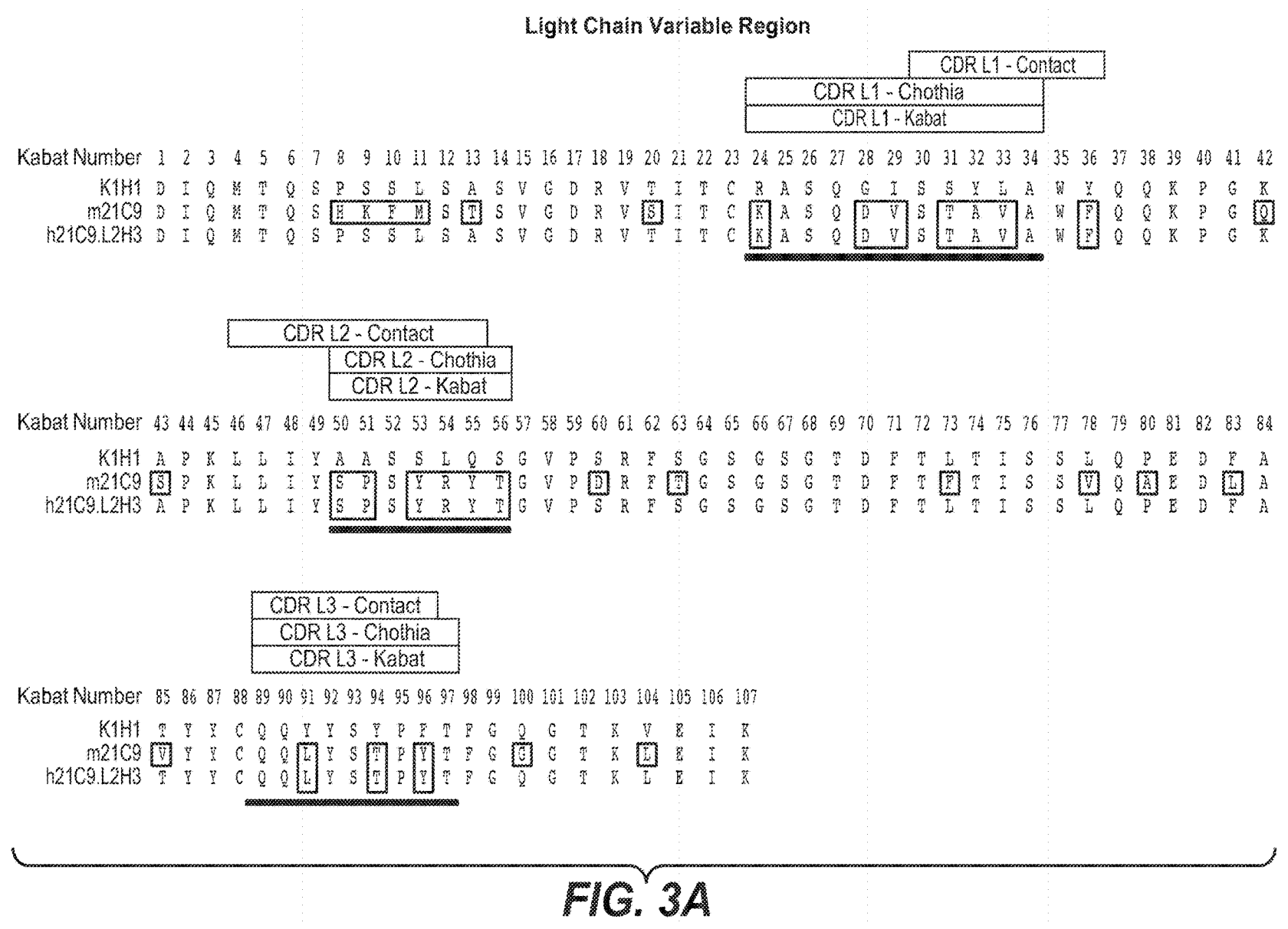
Figure 3B:
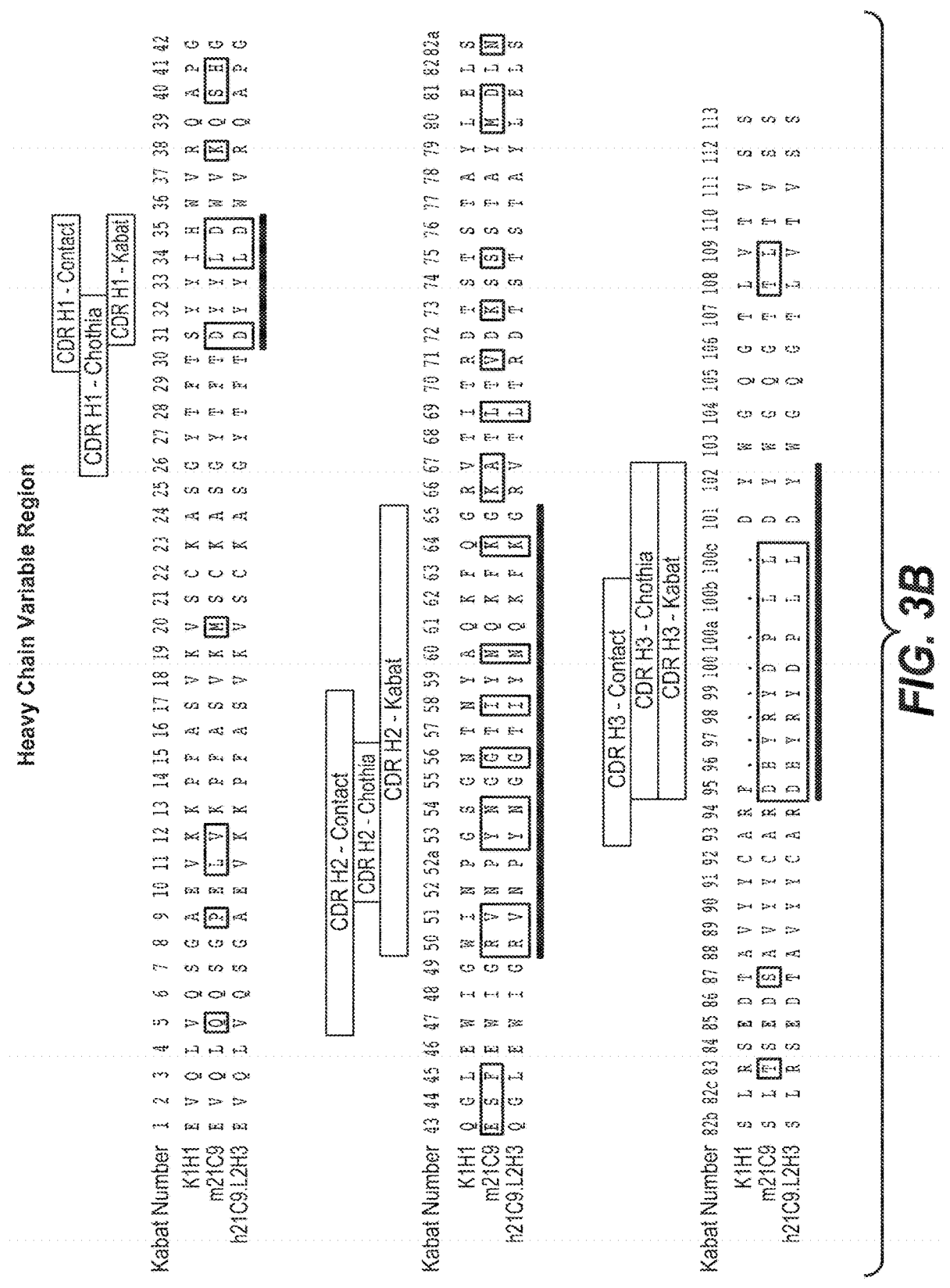

Provided herein are an anti-CLL-1 antibody comprising a CLL-1 binding domain comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the anti-CLL-1 antibody comprising the CLL-1 binding domain comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the anti-CLL-1 antibody comprising the CLL-1 binding domain comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CLL-1 antibody comprising a CLL-1 binding domain according to any of the above embodiments is a monoclonal antibody, including a human antibody. In one embodiment, an anti-CLL-1 antibody comprising a CLL-1 binding domain is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

b) CD3 Binding Domains of Anti-CLL1 Antibodies

In some embodiments, the CD3 binding domain of the anti-CLL-1 antibody binds to a human CD3 polypeptide or a cynomolgus monkey (cyno) CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively. In certain embodiments, an anti-CLL-1 antibody is provided comprising a CD3 binding domain which binds to an epitope within a fragment of CD3 (e.g., human CD3ε) consisting of amino acids 1-26 or 1-27 of human CD3ε. In some embodiments, the anti-CLL-1 antibody is a bispecific antibody. In some embodiments, the anti-CLL-1 antibody is a bispecific IgG antibody.

In some embodiments, CD3 binding domain binds the human CD3ε polypeptide with a Kd of 250 nM or lower. In some embodiments, the CD3 binding domain binds the human CD3ε polypeptide with a Kd of 100 nM or lower. In some embodiments, the CD3 binding domain binds the human CD3ε polypeptide with a Kd of 15 nM or lower. In some embodiments, CD3 binding domain binds the human CD3ε polypeptide with a Kd of 10 nM or lower. In some embodiments, CD3 binding domain binds the human CD3ε polypeptide with a Kd of 5 nM or lower. In some embodiments, the CD3 binding arm of the anti-CLL1 antibody binds human CD3 with an affinity less than 50 nM and greater than 1 nM. In some embodiments, the CD3 binding arm of the anti-CLL1 antibody binds human CD3 with an affinity less than 1 nM and greater than 0.1 nM. In some embodiments, the CD3 binding arm of the anti-CLL1 antibody binds human CD3 with an affinity less than 0.1 nM and greater than 0.01 nM. In some embodiments, the affinity of the CD3 binding arm is determined by Biacore. In some embodiments, the human CD3 is hCD3εγ. In some embodiments, the human CD3 is hCD3ε 1-27 Fc.

In some embodiments, the CD3 binding domain of the anti-CLL-1 antibody binds contacts with amino acids of human CD3ε at a distance of 3.5 Angstroms, 3.25 Angstroms, 3.00 Angstroms, 2.75 Angstroms, or less. In certain embodiments, the CD3 binding domain is provided that binds to an epitope consisting of one, two, three, four, or five amino acids of human CD3ε at a distance of 3.5 Angstroms, 3.25 Angstroms, 3.00 Angstroms, 2.75 Angstroms or less. In one embodiment, the CD3 binding domain of the anti-CLL-1 antibody makes unique contacts with amino acids of human CD3ε at a distance of 3.5 Angstroms or less. In certain embodiments, the CD3 binding domain is provided that binds to an epitope consisting of one, two, three, four, or five amino acids of human CD3ε at a distance of 3.5 Angstroms or less. For example, in certain embodiments, the CD3 binding domain is provided that binds to an epitope consisting of amino acids of human CD3ε selected from Gln1, Asp2, Asn4, Glu6, and Met7. In one particular embodiment, the CD3 binding domain binds to an epitope that specifically includes Glu6. In certain other embodiments, the CD3 binding domain is provided that does not bind to an epitope that includes human CD3ε amino acid Glu5. In certain other embodiments, the CD3 binding domain is provided that does not bind to an epitope that includes human CD3ε amino acids Gly3 and Glu5.

A CD3 epitope may be determined by the CD3 binding domain binding to peptide fragments of the epitope. Alternatively, a CD3 epitope may be determined by alanine scanning mutagenesis. In one embodiment, a reduction in binding of a CD3 binding domain to mutated CD3 by 20%, 30%, 50%, 80% or more indicates the amino acid residue of CD3 mutated in an alanine scanning mutagenesis assay is an epitope residue for that CD3 binding domain. Alternatively, a CD3 epitope may be determined by mass spectrometry. In some embodiments, the epitope is determined by crystallography (e.g., crystallography methods).

In some embodiments, the CD3 epitope as determined by crystallography is determined using amino acids Q1-M7 of CD3. In some embodiments, the CD3 epitope as determined by crystallography is determined using amino acids QDGNEEMGGITQTPYK (SEQ ID NO: 107) of CD3.

In some embodiments, the CD3 epitope as determined by crystallography may be performed by combining the anti-CD3 antibody Fab, dissolved in 0.15 M NaCl, 25 mM tris, pH 7.5 at 10 mg/ml, with a 2-fold molar excess (1 mg) of CD3ε peptide and initially screening a sparse matrix of precipitants in a sitting drop vapor diffusion format. Optimized crystals may be grown from a 1:1 mixture with reservoir solution containing 70% v/v methyl-pentanediol, and 0.1 M HEPES buffer at pH 7.5. The reservoir may be be used as a cryoprotectant. The crystals may be transferred to cryogenic temperature by sudden immersion into liquid nitrogen.

The diffraction data for crystals may be collected at Advanced Photon Source beam line 221D, using a MAR300 CCD detector. The recorded diffractions may be integrated and scaled using the program HKL2000.

The structure may be phased by molecular replacement (MR) method using program Phaser. For example, the MR search model is a Fab subunit derived from a crystal structure of HGFA/Fab complex (PDB code: 2R0L). The CD3ε peptide is built into the structure based on a Fo-Fc map. The structure may be subsequently refined with programs REFMACS and PHENIX using the maximum likelihood target functions, anisotropic individual B-factor refinement method, and TLS refinement method, to achieve convergence.

In some embodiments of any of the anti-CLL-1 antibodies, the CD3 binding domain comprises the hypervariable regions (HVRs) (a) HVR-H1 comprising the amino acid sequence of SEQ ID NO:88; (b) HVR-H2 comprising the amino acid sequence of SEQ ID NO:89; (c) HVR-H3 comprising the amino acid sequence of SEQ ID NO:90; (d) HVR-L1 comprising the amino acid sequence of SEQ ID NO:74; (e) HVR-L2 comprising the amino acid sequence of SEQ ID NO:91; and (f) HVR-L3 comprising the amino acid sequence of SEQ ID NO:92. In some embodiments, the CD3 binding domain comprises (a) a VH domain comprising (i) HVR-H1 comprising the amino acid sequence of SEQ ID NO:88, (ii) HVR-H2 comprising the amino acid sequence of SEQ ID NO:89, and (iii) HVR-H3 comprising an amino acid sequence selected from SEQ ID NO:90; and (b) a VL domain comprising (i) HVR-L1 comprising the amino acid sequence of SEQ ID NO:74, (ii) HVR-L2 comprising the amino acid sequence of SEQ ID NO:91, and (iii) HVR-L3 comprising the amino acid sequence of SEQ ID NO:92.

For example, in some embodiments of any of the anti-CLL1 antibodies, the anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) a CD3 binding domain comprises the following six HVRs: (a) HVR-H1 comprising the amino acid sequence of SEQ ID NO:88; (b) HVR-H2 comprising the amino acid sequence of SEQ ID NO:89; (c) HVR-H3 comprising the amino acid sequence of SEQ ID NO:90; (d) HVR-L1 comprising the amino acid sequence of SEQ ID NO:74; (e) HVR-L2 comprising the amino acid sequence of SEQ ID NO:91; and (f) HVR-L3 comprising the amino acid sequence of SEQ ID NO:92. In some embodiments, the anti-CLL-1 antibody comprises a CLL-1 binding domain comprising a heavy chain variable region comprising the sequence of SEQ ID NO:34 and a light chain variable region comprising the sequence of SEQ ID NO:32.

In some embodiments of any of the anti-CLL-1 antibodies, the CD3 binding domain comprises the hypervariable regions (HVRs) (a) HVR-H1 comprising the amino acid sequence of SEQ ID NO:71; (b) HVR-H2 comprising the amino acid sequence of SEQ ID NO:72; (c) HVR-H3 comprising the amino acid sequence of SEQ ID NO:73; (d) HVR-L1 comprising the amino acid sequence of SEQ ID NO:74; (e) HVR-L2 comprising the amino acid sequence of SEQ ID NO:75; and (f) HVR-L3 comprising the amino acid sequence of SEQ ID NO:76. In some embodiments, the CD3 binding domain comprises (a) a VH domain comprising (i) HVR-H1 comprising the amino acid sequence of SEQ ID NO:71, (ii) HVR-H2 comprising the amino acid sequence of SEQ ID NO:72, and (iii) HVR-H3 comprising an amino acid sequence selected from SEQ ID NO:73; and (b) a VL domain comprising (i) HVR-L1 comprising the amino acid sequence of SEQ ID NO:74, (ii) HVR-L2 comprising the amino acid sequence of SEQ ID NO:75, and (iii) HVR-L3 comprising the amino acid sequence of SEQ ID NO:76. In some instances, the CD3 binding domain may have a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO:82 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:83. In some instances, the CD3 binding domain may have a VH domain comprising the amino acid sequence of SEQ ID NO:82 and a VL domain comprising the amino acid sequence of SEQ ID NO:83. In a particular instance, the CD3 binding domain can be 40G5c, or a derivative or clonal relative thereof.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:71; (b) HVR-H2 comprising the amino acid sequence of SEQ ID NO:72; (c) HVR-H3 comprising the amino acid sequence of SEQ ID NO:73; (d) HVR-L1 comprising the amino acid sequence of SEQ ID NO:74; (e) HVR-L2 comprising the amino acid sequence of SEQ ID NO:75; and (f) HVR-L3 comprising the amino acid sequence of SEQ ID NO:76. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:82 and a light chain variable region comprising the sequence of SEQ ID NO:83.

In some embodiments of any of the anti-CLL-1 antibodies, the CD3 binding domain (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:92. In some embodiments, the CD3 binding domain comprises (a) a VH domain comprising (i) HVR-H1 comprising the amino acid sequence of SEQ ID NO:77, (ii) HVR-H2 comprising the amino acid sequence of SEQ ID NO:78, and (iii) HVR-H3 comprising an amino acid sequence selected from SEQ ID NO:79; and (b) a VL domain comprising (i) HVR-L1 comprising the amino acid sequence of SEQ ID NO:74, (ii) HVR-L2 comprising the amino acid sequence of SEQ ID NO:80, and (iii) HVR-L3 comprising the amino acid sequence of SEQ ID NO:92.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80 and (f) HVR-L3 comprising the amino acid sequence of SEQ ID NO:92. In some embodiments, the anti-CLL-1 antibody comprises a CLL-1 binding domain comprising a heavy chain variable region comprising the sequence of SEQ ID NO:34 and a light chain variable region comprising the sequence of SEQ ID NO:32.

In some embodiments of any of the anti-CLL-1 antibodies, the CD3 binding domain (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:81. In some embodiments, the CD3 binding domain comprises (a) a VH domain comprising (i) HVR-H1 comprising the amino acid sequence of SEQ ID NO:77, (ii) HVR-H2 comprising the amino acid sequence of SEQ ID NO:78, and (iii) HVR-H3 comprising an amino acid sequence selected from SEQ ID NO:79; and (b) a VL domain comprising (i) HVR-L1 comprising the amino acid sequence of SEQ ID NO:74, (ii) HVR-L2 comprising the amino acid sequence of SEQ ID NO:80, and (iii) HVR-L3 comprising the amino acid sequence of SEQ ID NO:81. In some instances, the CD3 binding domain may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:84 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:85. In some instances, the CD3 binding domain may have a VH domain comprising the amino acid sequence of SEQ ID NO:84 and a VL domain comprising the amino acid sequence of SEQ ID NO:85. In a particular instance, the CD3 binding domain can be 38E4v1, or a derivative or clonal relative thereof.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:81. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:84 and a light chain variable region comprising the sequence of SEQ ID NO:85.

In some embodiments of any of the anti-CLL-1 antibodies, the CD3 binding domain (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:76. In some embodiments, the CD3 binding domain comprises (a) a VH domain comprising (i) HVR-H1 comprising the amino acid sequence of SEQ ID NO:77, (ii) HVR-H2 comprising the amino acid sequence of SEQ ID NO:78, and (iii) HVR-H3 comprising an amino acid sequence selected from SEQ ID NO:79; and (b) a VL domain comprising (i) HVR-L1 comprising the amino acid sequence of SEQ ID NO:74, (ii) HVR-L2 comprising the amino acid sequence of SEQ ID NO:80, and (iii) HVR-L3 comprising the amino acid sequence of SEQ ID NO:76. In some instances, the CD3 binding domain may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:84 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:93. In some instances, the CD3 binding domain may have a VH domain comprising the amino acid sequence of SEQ ID NO:84 and a VL domain comprising the amino acid sequence of SEQ ID NO:93. In a particular instance, the CD3 binding domain can be 38E4v11, or a derivative or clonal relative thereof.

For example, provided herein are anti-CLL1 antibodies comprising (i) a CLL-1 binding domain comprises the following six HVRs: (a) an HVR-H1 comprising the amino acid sequence of SEQ ID NO:8; (b) an HVR-H2 comprising the amino acid sequence of SEQ ID NO:11; (c) an HVR-H3 comprising the amino acid sequence of SEQ ID NO:10; (d) an HVR-L1 comprising the amino acid sequence of SEQ ID NO:5; (e) an HVR-L2 comprising the amino acid sequence of SEQ ID NO:6; and (f) an HVR-L3 comprising the amino acid sequence of SEQ ID NO:7; and (ii) the CD3 binding domain comprises (a) HVR-H1 comprising the amino acid sequence of SEQ ID NO:77; (b) HVR-H2 comprising the amino acid sequence of SEQ ID NO:78; (c) HVR-H3 comprising the amino acid sequence of SEQ ID NO:79; (d) an HVR-L1 comprising the amino acid sequence of SEQ ID NO:74; (e) HVR-L2 comprising the amino acid sequence of SEQ ID NO:80; and (f) HVR-L3 comprising the amino acid sequence of SEQ ID NO:76. In some embodiments, the anti-CLL-1 antibody comprises (i) a CLL-1 binding domain comprising a heavy chain variable region comprising the sequence of SEQ ID NO:34 and a light chain variable region comprising the sequence of SEQ ID NO:32 and (ii) a CD3 binding domain comprising a heavy chain variable region comprising the sequence of SEQ ID NO:84 and a light chain variable region comprising the sequence of SEQ ID NO:93.

In some embodiments, the CD3 binding arm of the anti-CLL1 antibody is a chimeric anti-murine CD3 binding arm. In some embodiments, the chimeric anti-murine CD3 bind arm is 2C11 (Leo et al. *Proc Natl Acad Sci USA*. 84: 1374-1378, 1987). In some embodiments, the CD3 binding arm of the anti-CLL1 antibody is a mouse anti-human CD3 binding arm. In some embodiments, the mouse anti-human CD3 binding arm is SP34 (Pessano et al. *The EMBO Journal.* 4: 337-344, 1985). In some embodiments, the CD3 binding arm of the anti-CLL1 antibody is OKT3. (Fernandes, R. A. et al. 2012. J. Biol. Chem. 287: 13324-13335). In some embodiments, the CD3 binding arm of the anti-CLL1 antibody is UCHT1 (Id.). In some embodiments, the CD3 binding arm of the anti-CLL1 antibody is Muromonab-CD3 (CAS Registry Number: 140608-64-6). In some embodiments, the CD3 binding arm of the anti-CLL1 antibody is described in US Patent Application Publication 2010/0150918.

c) Multispecific Anti-CLL1 Antibodies

In certain embodiments, an anti-CLL-1 antibody provided herein is a multispecific antibody, e.g. a bispecific antibody. Multispecific antibodies are monoclonal antibodies that have binding specificities for at least two different sites. In certain embodiments, one of the binding specificities is for CLL-1 and the other is for any other antigen. In certain embodiments, bispecific antibodies may bind to two different epitopes of CLL-1. Bispecific antibodies may also be used to localize cytotoxic agents to cells which express CLL-1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991). Multispecific antibodies may also be engineered using immunoglobulin crossover (also known as Fab domain exchange or CrossMab format) technology (see eg., WO2013026833, WO2009/080253; Schaefer et al., *Proc. Natl. Acad. Sci. USA*, 108:111B7-11192 (2011)).

Engineered antibodies with three or more functional antigen binding sites, including "Octopus antibodies," are also included herein (see, e.g. US 2006/0025576A1, WO2013026833, and WO2012073985).

The anti-CLL-1 antibody or fragment herein also includes a "Dual Acting FAb" or "DAF" comprising an antigen binding site that binds to CLL-1 as well as another, different antigen (see, US 2008/0069820, for example).

In a further aspect, the CLL-1 binding domain, CD3 binding domain and/or CLL-1 antibody according to any of the above embodiments may incorporate any of the features, singly or in combination, as described in Sections 1-6 below:

1. Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. 10 M or less, e.g. from 10 M to $10^{-13}$M, e.g., from 10 M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000, BAICOR®-T200 or a BIACORE®-3000 (BIAcore, Inc., Piscataway, N.J.) at 25° C. with immobilized antigen CM5 chips at ~10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) and/or HBS-P (0.01 M Hepes pH7.4, 0.15M NaCl, 0.005% Surfactant P20) before injection at a flow rate of 5 µl/minute and/or 30 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self antigens without any immunization as described by Griffiths et al., *EMBO J,* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In some aspects the anti-CLL-1 antibody (e.g., anti-CLL-1 TDB antibody) comprises an Fc region comprising an N297G mutation. In some embodiments, the anti-CLL-1 antibody comprises an L234A, L235A, and P329G mutation at amino acid residues 234, 235, and 329 according to EU numbering.

In some embodiments, the anti-CLL-1 antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-CD3 antibody is an IgG1 antibody.

In some embodiments of any of the anti-CLL-1 antibodies, (a) the CD3 binding domain comprises a Fc domain, wherein the Fc domain comprises T366S, L368A, Y407V, and N297G substitution mutations according EU numbering and (b) the CLL-1 binding domain comprises a Fc domain, wherein the Fc domain comprises T366W and N297G substitution mutations according EU numbering. In some embodiments of any of the anti-CLL-1 antibodies, (a) the CD3 binding domain comprises a Fc domain, wherein the Fc domain comprises L234A, L235A, P329G, T366S, L368A, and Y407V, substitution mutations according EU numbering and (b) the CLL-1 binding domain comprises a Fc domain, wherein the Fc domain comprises L234A, L235A, P329G, and T366W substitution mutations according EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al.,

*Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-CLL-1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CLL-1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol*. 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-CLL-1 antibodies provided herein may be identified, screened for, or characterized for their physical/chemical properties and/or biological activities by various assays known in the art.

1. Binding Assays and Other Assays

Anti-CLL-1 antibodies provided herein may be identified, screened for, or characterized for their physical/chemical properties and/or biological activities by various assays known in the art.

In one aspect, an antibody and/or binding domain of the invention is tested for its antigen binding activity, e.g., by known methods such as ELISA, BIACore®, FACS, or Western blot.

In another aspect, competition assays may be used to identify an antibody and/or binding domain that competes with any of the antibodies described herein for binding to CLL-1 or CD3. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CLL-1 or CD3 is incubated in a solution comprising a first labeled antibody that binds to CLL-1 or CD3 (e.g., any of the antibodies described herein) and a second unlabeled antibody that is being tested for its ability to compete with the first antibody for binding to CLL-1 or CD3. The second antibody may be present in a hybridoma supernatant. As a control, immobilized CLL-1 or CD3 is incubated in a solution comprising the first labeled antibody but not the second unlabeled antibody. After incubation under conditions permissive for binding of the first antibody to CLL-1 or CD3, excess unbound antibody is removed, and the amount of label associated with immobilized CLL-1 or CD3 is measured. If the amount of label associated with immobilized CLL-1 or CD3 is substantially reduced in the test sample relative to the control sample, then that indicates that the second antibody is competing with the first antibody for binding to CLL-1 or CD3. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-CLL-1 antibodies (e.g., anti-CLL-1/CD3 TDB antibody) thereof having biological activity. Biological activity may include, e.g., the ability to inhibit cell growth or proliferation (e.g., "cell killing" activity), the ability to induce cell death, including programmed cell death (apoptosis), or antigen binding activity. Antibodies having such biological activity in vivo and/or in vitro are also provided.

In some embodiments, the activity comprises ability to support target cell (e.g., CLL-1 positive cells) killing and/or the activation of the cytotoxic T cells. In certain embodiments, an anti-CLL-1 antibody (e.g., anti-CLL-1/CD3 TDB antibody) of the invention is tested for such target cell (e.g., CLL-1 positive cells) killing and/or the activation of the cytotoxic effect of T cells biological activity by any of the methods described herein, in particular the Examples. In some embodiments, the target cells such as AML tumor cell lines, PBMC, or AML patient bone marrow cells, may be pre-incubated for 1-2 hours at 37° C. in RPMI medium containing 10% FCS, 2 mM Glutamine and 0.3 mg/ml purified low endotoxin human IgG (Molecular Innovations, HU-GF-ED) to prevent non-specific binding of the TDB to cells with surface expression of FcγRs. In some embodiments, PBMCs may be isolated from normal human donors, and untouched CD8+ T cells in the PBMCs were enriched using the kit from Miltenyi Biotec GmbH (Miltenyi; 130-096-495). The assay may be performed in a 96-well round bottom plate (Costar 3799) containing 60,000 cells/well of human CD8+ T cells and 20,000 cells/well of hIgG-blocked target cells; the effector to target ratio (E:T) was 3:1. The anti-CLL-1 antibody (e.g., anti-CLL-1/CD3 TDB antibody) may be added as a 10× working solution serially diluted 3-fold to a final assay concentration spanning 0-10 ug/ml or 0-1 ug/ml. The order of addition may be as follows, 50 ul of 2× target cells, 11 ul of 10×3-fold serially diluted TDB, and 50 ul of 2×CD8+ T cells. The contents may be mixed on a Titer Plate Shaker (Thermo) at setting 6 for 15 sec and incubated for at 37° C. for about 40 hrs. The plate may be mixed once each day. In some embodiments, depletion of hCLL-1 expressing EOL-1, THP-1, HL-60, Nomo-1, ML-2, PL-21, U937 and Molm-13 cells may be monitored using either an anti-CD123-APC (BD Pharmingen; 560087) or anti-CD33-APC reagent (BD Pharmingen; 551378) and propidium iodide by FACS. Activation of CD8+ T cells may be monitored using a combination of anti-CD8-FITC (BD Pharmingen; 555634), anti-CD69-PE (BD Pharmingen; 555531) and anti-CD25 (BD Pharmingen; 555434).

In some embodiments, human or cynomolgus PBMCs may be isolated by Hypaque-Ficoll gradient centrifugation (Ficoll-Paque Plus, GE Healthcare), washed at low speed to remove platelets and resuspended in RPMI containing hIgG to block non-specific binding by TDBs to FcγRs. The assay may be performed as described above, except that PBMCs at a concentration of 200,000/well were incubated with 11 ul of 10×3-fold serially diluted anti-CLL-1 antibody (e.g., anti-CLL-1/CD3 TDB antibody). Target cell killing (CD14+ monocytes) and activation of effector T cells (CD8+) may be evaluated at ~40 hours by FACS. Depletion of hCLL-1 expressing CD14+ monocytes may be monitored using an anti-CD14-APC reagent (Human BD Pharmingen; 555399, Cyno Miltenyi: 130-091-243) and propidium iodide.

D. Immunoconjugates

The invention also provides immunoconjugates comprising an anti-CLL-1 antibody (e.g., anti-CLL-1/CD3 TDB antibody) herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In one aspect, anti-CLL-1 antibody (e.g., anti-CLL-1/CD3 TDB antibody) provided herein are useful for detecting the presence of CLL-1 in a biological sample. The term "detecting" as used herein encompasses quantitative or qualitative detection. In certain embodiments, a biological sample comprises a cell or tissue. In certain embodiments, such tissues include normal and/or cancerous tissues that express CLL-1 at higher levels relative to other tissues In one embodiment, an anti-CLL-1 antibody for use in a method of diagnosis or detection is provided. In a further aspect, a method of detecting the presence of CLL-1 in a biological sample is provided. In certain embodiments, the method comprises contacting the biological sample with an anti-CLL-1 antibody as described herein under conditions permissive for binding of the anti-CLL-1 antibody to CLL-1, and detecting whether a complex is formed between the anti-CLL-1 antibody and CLL-1. Such method may be an in vitro or in vivo method. In one embodiment, an anti-CLL-1 antibody is used to select subjects eligible for therapy with an anti-CLL-1 antibody, e.g. where CLL-1 is a biomarker for selection of patients.

Exemplary disorders that may be diagnosed or detected according to any of the above embodiments include CLL-1-positive cancers, such as CLL-1-positive AML, CLL-1-positive CML, CLL-1-positive MDS, CLL-1-positive chronic myelomonocytic leukemia, CLL-1-positive APL, CLL-1-positive chronic myeloproliferative disorder, CLL-1-positive thrombocytic leukemia, CLL-1-positive pre-B-ALL, CLL-1-positive preT-ALL, CLL-1-positive multiple myeloma, CLL-1-positive mast cell disease, CLL-1-positive mast cell leukemia, CLL-1-positive mast cell sarcoma, CLL-1-positive myeloid sarcomas, CLL-1-positive lymphoid leukemia, and CLL-1-positive undifferentiated leukemia. In some embodiments, a CLL-1-positive cancer is a cancer that receives an anti-CLL-1 immunohistochemistry (IHC) or in situ hybridization (ISH) score greater than "0," which corresponds to very weak or no staining in >90% of tumor cells, under the conditions described herein in Example B. In another embodiment, a CLL-1-positive cancer expresses CLL-1 at a 1+, 2+ or 3+ level, as defined under the conditions described herein in Example B. In some embodiments, a CLL-1-positive cancer is a cancer that expresses CLL-1 according to a reverse-transcriptase PCR (RT-PCR) assay that detects CLL-1 mRNA. In some embodiments, the RT-PCR is quantitative RT-PCR.

Certain other methods can be used to detect binding of anti-CLL-1 antibodies to CLL-1. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, labeled anti-CLL-1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-CLL-1 antibody (e.g., anti-CLL-1/CD3 TDB antibody) as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulations herein may also contain more than one active compound as necessary for the particular indication being treated, preferably those with complementary activities that do not adversely affect each other. For example, in addition to an anti-CLL-1 antibody, it may be desirable to include in the one formulation, an additional antibody, e.g., a second anti-CLL-1 antibody which binds a different epitope on the CLL-1 polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-CLL-1 antibodies (e.g., anti-CLL-1/CD3 TDB antibody) provided herein may be used in therapeutic methods.

In one aspect, an anti-CLL-1 antibody (e.g., anti-CLL-1/CD3 TDB antibody) for use as a medicament is provided. In further aspects, an anti-CLL-1 antibody (e.g., anti-CLL-1/CD3 TDB antibody) for use in treating or delaying progression of a cell proliferative disorder (e.g., cancer and/or AML) is provided. In certain embodiments, an anti-CLL-1 antibody (e.g., anti-CLL-1/anti-CD3 bispecific antibody) for use in a method of treatment is provided. In certain embodiments, the invention provides an anti-CLL-1 antibody (e.g., anti-CLL-1/CD3 TDB antibody) for use in a method of treating an individual having a cell proliferative disorder comprising administering to the individual an effective amount of the anti-CLL-1 antibody (e.g., anti-CLL-1/CD3 TDB antibody). In one such embodiment, the method further comprises administering to the individual an effective amount of at least one additional therapeutic agent, for example, as described below. In further embodiments, the invention provides an anti-CLL-1 antibody (e.g., anti-CLL-1/CD3 TDB antibody) for use in enhancing immune function in an individual having a cell proliferative disorder (e.g., AML). In certain embodiments, the invention provides an anti-CLL-1 antibody (e.g., anti-CLL-1/CD3 TDB antibody) for use in a method of enhancing immune function in an individual having a cell proliferative disorder (e.g., AML) comprising administering to the individual an effective amount of the anti-CLL-1 antibody (e.g., anti-CLL-1/CD3 TDB antibody) to activate effector cells (e.g., T cells, e.g., CD8+ and/or CD4+ T cells), expand (increase) an effector cell population, and/or kill a target cell (e.g., target cell). An "individual" according to any of the above embodiments may be a human.

In a further aspect, the invention provides for the use of an anti-CLL-1 antibody (e.g., anti-CLL-1/CD3 TDB antibody)) in the manufacture or preparation of a medicament. In one embodiment, the medicament is for treatment of a cell proliferative disorder (e.g., cancer and/or AML). In a further embodiment, the medicament is for use in a method of treating a cell proliferative disorder (e.g., AML) comprising administering to an individual having a cell proliferative disorder (e.g., AML) an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, and/or killing target cells (e.g., target cells) in the individual. In a further embodiment, the medicament is for use in a method of enhancing immune function in an individual having a cell proliferative disorder (e.g., AML) or an autoimmune disorder comprising administering to the individual an amount effective of the medicament to activate effector cells (e.g., T cells, e.g., CD8+ and/or CD4+ T cells), expand (increase) an effector cell population, and/or kill a target cell (e.g., target cell). An "individual" according to any of the above embodiments may be a human.

In a further aspect, the invention provides a method for treating a cell proliferative disorder (e.g., cancer and/or AML). In one embodiment, the method comprises administering to an individual having such a cell proliferative disorder (e.g., AML) an effective amount of an anti-CLL-1 antibody (e.g., anti-CLL-1/CD3 TDB antibody). In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder (e.g., AML) in an individual having a cell proliferative disorder (e.g., AML). In one embodiment, the method comprises administering to the individual an effective amount of an anti-CLL-1 antibody (e.g., anti-CLL-1/CD3 TDB antibody) to activate effector cells (e.g., T cells, e.g., CD8+ and/or CD4+ T cells), expand (increase) an effector cell population, and/or kill a target cell (e.g., target cell). In one embodiment, an "individual" is a human.

An anti-CLL-1 antibody (e.g., anti-CLL-1/CD3 TDB antibody) of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-CLL-1 antibody thereof under conditions permissive for binding to CLL-1. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In further embodiments, the cell is a monocyte, granulocyte, and/or progenitors of the monocyte/granulocyte lineage. In some embodiments, the cell is positive for the presence of FLT3 internal tandem repeats. In some embodiments, cell is positive for the presence of a MLL-AF9 fusion gene (e.g., MLL-AF9 translocation). In some embodiments, the cell is positive for the presence of a chromosome 11q23 translocation. In some embodiments, the cell is positive for positive for the presence of a translocation t(9;11)(p22;q23).

Any of the anti-CLL-1 antibody (e.g., anti-CLL-1/CD3 TDB antibody) provided herein may be used in methods, e.g., therapeutic methods.

In one aspect, an anti-CLL-1 antibody (e.g., anti-CLL-1/CD3 TDB antibody) provided herein is used in a method of inhibiting proliferation of a CLL-1-positive cell (CLL-1-positive cell proliferative disorder, the method comprising exposing the cell to the anti-CLL-1 antibody (e.g., anti-CLL-1/CD3 TDB antibody) under conditions permissive for binding of the anti-CLL-1 antibody (e.g., anti-CLL-1/CD3 TDB antibody) to CLL-1 on the surface of the cell, thereby inhibiting the proliferation of the cell. In certain embodiments, the method is an in vitro or an in vivo method. In further embodiments, the cell is a monocyte, granulocyte, and/or progenitors of the monocyte/granulocyte lineage. In some embodiments, the cell is positive for the presence of FLT3 internal tandem repeats. In some embodiments, cell is positive for the presence of a MLL-AF9 fusion gene (e.g., MLL-AF9 translocation). In some embodiments, the cell is positive for the presence of a chromosome 11q23 translocation. In some embodiments, the cell is positive for positive for the presence of a translocation t(9;11)(p22;q23).

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-CLL-1 antibody (e.g., anti-CLL-1/CD3 TDB antibody) for use as a medicament is provided. In further aspects, an anti-CLL-1 antibody (e.g., anti-CLL-1/CD3 TDB antibody) for use in a method of treatment is provided. In certain embodiments, an anti-CLL-1 antibody (e.g., anti-CLL-1/CD3 TDB antibody) for use in treating cell proliferative disorder (e.g., CLL-1-positive cancer) is provided. In certain embodiments, the invention provides an anti-CLL-1 antibody (e.g., anti-CLL-1/CD3 TDB antibody) for use in a method of treating an individual having a cell proliferative disorder (e.g., CLL-1-positive cancer), the method comprising administering to the individual an effective amount of the anti-CLL-1 antibody (e.g., anti-CLL-1/CD3 TDB antibody). In one such embodiment, the method further comprises administering to the individual an effective amount of at least one additional therapeutic agent, e.g., as described below.

In a further aspect, the invention provides for the use of an anti-CLL-1 antibody (e.g., anti-CLL-1/CD3 TDB antibody) in the manufacture or preparation of a medicament. In one embodiment, the medicament is for treatment of cell proliferative disorder (e.g., CLL-1-positive cancer). In some embodiments, the cancer is AML. In a further embodiment, the medicament is for use in a method of treating cell proliferative disorder (e.g., CLL-1-positive cancer), the method comprising administering to an individual having CLL-1-positive cancer an effective amount of the medicament. In one such embodiment, the method further comprises administering to the individual an effective amount of at least one additional therapeutic agent, e.g., as described below.

In a further aspect, the invention provides a method for treating CLL-1-positive cancer. In one embodiment, the method comprises administering to an individual having such CLL-1-positive cancer an effective amount of an anti-CLL-1 antibody (e.g., anti-CLL-1/CD3 TDB antibody). In one such embodiment, the method further comprises administering to the individual an effective amount of at least one additional therapeutic agent, as described below.

A cell proliferative disorder (e.g., CLL-1-positive cancer) according to any of the above embodiments may be, e.g., CLL-1-positive AML, CLL-1-positive chronic myeloid leukemia (CML), CLL-1-positive myelodysplastic syndrome (MDS), CLL-1-positive chronic myelomonocytic leukemia, CLL-1-positive APL, CLL-1-positive chronic myeloproliferative disorder, CLL-1-positive thrombocytic leukemia, CLL-1-positive pre-B-ALL, CLL-1-positive preT-ALL, CLL-1-positive multiple myeloma, CLL-1-positive mast cell disease, CLL-1-positive mast cell leukemia, CLL-1-positive mast cell sarcoma, CLL-1-positive myeloid sarcomas, CLL-1-positive lymphoid leukemia, and CLL-1-positive undifferentiated leukemia. In some embodiments, a CLL-1-positive cancer is a cancer that receives an anti-CLL-1 immunohistochemistry (IHC) or in situ hybridization (ISH) score greater than "0," which corresponds to very weak or no staining in >90% of tumor cells, under the conditions described herein in Example B. In another embodiment, a CLL-1-positive cancer expresses CLL-1 at a 1+, 2+ or 3+ level, as defined under the conditions described herein in Example B. In some embodiments, a CLL-1-positive cancer is a cancer that expresses CLL-1 according to a reverse-transcriptase PCR (RT-PCR) assay that detects CLL-1 mRNA. In some embodiments, the RT-PCR is quantitative RT-PCR.

In some embodiments, cell proliferative disorder according to any of the above embodiments may be, e.g., AML, CML, and/or MDS. In some embodiments, CLL-1-positive cell proliferative disorder is a CLL-1-positive AML, CLL-1-positive CML, CLL-1-positive MDS. In some embodiments, the AML is one or more of AML subtype 1, AML subtype 2, AML subtype 3, AML subtype 4, AML subtype 5, AML subtype 6, and AML subtype 7. In some embodiments, the AML is AML subtype 3 (acute promyelocytic leukemia, APML). In some embodiments, the AML is one or more of AML subtype 1, AML subtype 2, AML subtype 4, AML subtype 5, AML subtype 6, and AML subtype 7, and not AML subtype 3.

In some embodiments, the cell proliferative disorder (e.g., CLL-1-positive cancer and/or AML) is positive for the presence of a mutation in FLT3, nucleophosmin (NPM1), CCAAT/enhancer binding protein alpha (C/EBPα) (CEBPA), and/or c-KIT. In some embodiments, the cell proliferative disorder (e.g., CLL-1-positive cancer and/or AML) is positive for the presence of FLT3 internal tandem repeats. In some embodiments, the cell proliferative disorder (e.g., CLL-1-positive cancer and/or AML) is positive for the presence of FLT3 tyrosine kinase domain point mutations. In some embodiments, the cell proliferative disorder (e.g., CLL-1-positive cancer and/or AML) is positive for the presence of a mutation in isocitrate dehydrogenase 1 and/or 2 (IDH1 and/or IDH2). In some embodiments, the cell proliferative disorder (e.g., CLL-1-positive cancer and/or AML) is positive for the presence of a mutation in DNA methyltransferase 3A (DNMT3A). In some embodiments, the cell proliferative disorder (e.g., CLL-1-positive cancer and/or AML) is NK-AML positive for the presence of (a) a mutation in NPM1 and FLT3, (b) wild-type NPM1 and mutated FLT3, and/or (c) wild-type NPM1 and FLT3.

In some embodiments, the cell proliferative disorder (e.g., CLL-1-positive cancer and/or AML) is positive cytogenetic abnormality such as one or more of t(15;17), t(8;21), inv (16), t(16;16), t(9;11)(p22;q23), t(6;9)(p23;q34), inv(3)(q21 q26.2), inv(3;3)(q21;q26.2), t(1;22)(p13;q13), t(8;21)(q22; q22), inv(16)(p13;1q22), t(16;16)(p13.1;q22), and/or t(15; 17)(q22;q12). In some embodiments, the cell proliferative disorder (e.g., CLL-1-positive cancer and/or AML) is positive for the presence of a MLL-AF9 fusion gene (e.g., MLL-AF9 translocation). In some embodiments, the cell proliferative disorder (e.g., CLL-1-positive cancer and/or AML) is positive for the presence of a chromosome 11q23 translocation. In some embodiments, the cell proliferative disorder (e.g., CLL-1-positive cancer) is a cell proliferative disorder (e.g., CLL-1-positive cancer and/or AML) positive for the presence of a translocation t(9;11)(p22;q23).

In some embodiments, the cell proliferative disorder ((e.g., CLL-1-positive cancer and/or AML) refractory and/or resistant to an anti-AML antibody drug conjugate. In some embodiments, the anti-AML antibody drug conjugate is an anti-CD33 antibody drug conjugate, an anti-CLL1 antibody drug conjugate, and/or an anti-CD123 antibody drug conjugate. In some embodiments, the anti-CLL-1 antibody drug conjugate is anti-CLL-1 antibody drug conjugate (e.g., anti-CLL-1 pyrrolobenzodiazepine (PBD) antibody drug conjugate). In some embodiments, the anti-CLL-1 antibody drug conjugate is anti-CD33 antibody drug conjugate (e.g., anti-CD33 pyrrolobenzodiazepine (PBD) antibody drug conjugate). In some embodiments, the anti-CD123 antibody drug conjugate is anti-CD123 antibody drug conjugate (e.g., anti-CD123 pyrrolobenzodiazepine (PBD) antibody drug conjugate). In some embodiments, the anti-CLL-1 antibody drug conjugate is described in any one of U.S. Pat. No. 8,088,378 and/or US 2014/0030280, which are hereby incorporated by reference in their entirety.

An "individual" according to any of the above embodiments may be a human.

In a further aspect, the invention provides pharmaceutical formulations comprising any of the anti-CLL-1 antibodies (e.g., anti-CLL-1/CD3 TDB antibody) provided herein, e.g., for use in any of the above therapeutic methods. In one embodiment, a pharmaceutical formulation comprises any of the anti-CLL-1 antibodies provided herein and a pharmaceutically acceptable carrier. In another embodiment, a pharmaceutical formulation comprises any of the anti-CLL-1 antibodies (e.g., anti-CLL-1/CD3 TDB antibody) provided herein and at least one additional therapeutic agent, e.g., as described below.

In some embodiments of any of the methods, used, and/or pharmaceutical formulations described herein, the anti-CLL-1/CD3 TDB antibody may be used as a treatment induction therapy. In some embodiments of any of the methods, used, and/or pharmaceutical formulations described herein, the anti-CLL-1/CD3 TDB antibody may be used as a consolidation therapy. In some embodiments of any of the methods, used, and/or pharmaceutical formulations described herein, the anti-CLL-1/CD3 TDB antibody may be used as a salvage therapy.

Antibodies (e.g., anti-CLL-1/CD3 TDB antibody) described herein can be used either alone or in combination with other agents in a therapy. For instance, an antibody (e.g., anti-CLL-1/CD3 TDB antibody) described herein may be co-administered with at least one additional therapeutic agent. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is a hypomethylating agent such as 5-azacytidine or decitabine or guadecitabine. In some embodiments, the additional therapeutic agent is ATRA (all-trans retinoic acid). In some embodiments, the additional therapeutic agent is arsenic trioxide (also known as trisenox). In some embodiments, the additional therapeutic agent is daunorubicin hydrochloride (also known as cerubidine or rubidomycin). In some embodiments, the additional therapeutic agent is cyclophosphamide (also known as clafen, cytoxan, or neosar). In some embodiments, the additional therapeutic agent is cytarabine (also known as cytosar-u, tarabine pfs, or Ara-C). In some embodiments, the additional therapeutic agent is doxorubicin hydrochloride. In some embodiments, the additional therapeutic agent is idarubicin hydrochloride (also known as idamycin). In some embodiments, the additional therapeutic agent is thioguanine (also known as tabloid). In some embodiments, the additional therapeutic agent is vincristine sulfate (also known as vincasar pfs). In some embodiments, the additional therapeutic agent is sapacitabine. In some embodiments, the additional therapeutic agent is laromustine. In some embodiments, the additional therapeutic agent is tipifarnib. In some embodiments, the additional therapeutic agent is bortezomib (also known as VELCADE). In some embodiments, the additional therapeutic agent is hydroxyurea. In some embodiments, the additional therapeutic agent is etoposide. In some embodiments, the additional therapeutic agent is mitoxantrone. In some embodiments, the additional therapeutic agent is clofarabine. In some embodiments, the additional therapeutic agent is hydroxyurea. In some embodiments, the additional therapeutic agent is FLT3 inhibitor such as quizartinib or midostaurin. In some embodiments, the additional therapeutic agent is an anti-cancer quinolone derivative. In some embodiments, the additional therapeutic agent is vosaroxin. In some embodiments, the additional therapeutic agent is an IDH1 inhibitor or an IDH2 inhibitor. In some embodiments, the additional therapeutic agent is CHK1 inhibitor. In some embodiments, the CHK1 inhibitor is GDC-0575. In some embodiments, the additional therapeutic agent is a Plk inhibitor such as volasertib.

In some embodiments of any of the methods, the additional therapeutic agent is a BCL2 inhibitor. In some embodiments, the BCL2 inhibitor is venetoclax.

In some embodiments of any of the methods, the additional therapeutic agent is an epigenetic modifier. In some embodiments, the epigenetic modifier is a histone deacetylase inhibitor. In some embodiments, the epigenetic modifier is DNA methyltransferases I inhibitor. In some embodiments, the epigenetic modifier is a histone methyltransferases inhibitor. In some embodiments, the epigenetic modifier is a BET inhibitor. In some embodiments, the BET inhibitor selectively targets the first bromodomain (BD1). In some embodiments, the BET inhibitor selectively targets the second bromodomain (BD2). In some embodiments, the BET inhibitor is one or more of GSK1210151A, GSK525762, OTX-01, TEN-010, CPI-203, and CPI-0610.

In some embodiments, an antibody (e.g., anti-CLL-1/CD3 TDB antibody) described herein may be co-administered with chemotherapeutic agents. In some embodiments, the chemotherapeutic agents are cytarabine, daunorubicin hydrochloride, and etoposide. In some embodiments, the chemotherapeutic agents are daunorubicin hydrochloride and cytarabine. In some embodiments, the chemotherapeutic agents are fludara and oforta. In some embodiments, the chemotherapeutic agents are cytarabine and an anthracycline. In some embodiments, the anthracycline is daunorubicin, idarubicin, doxorubicin, or epirubicin. In some embodiments, the chemotherapeutic agents are mitoxantrone, etoposide, and cytarabine. In some embodiments, the chemotherapeutic agents are cytarabine, an anthracycline, and clofarabine.

In some embodiments, an antibody (e.g., anti-CLL-1/CD3 TDB antibody) described herein may be co-administered with chemotherapeutic agents and granulocyte colony stimulating factor. In some embodiments, the chemotherapeutic agents are fludarabine and cytarabine. In some embodiments, the chemotherapeutic agents are fludarabine, cytarabine, and idarubicin.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is stem cell transplant. In some embodiments, the additional therapy may be a separate administration of one or more of the therapeutic agents described above.

In some embodiments of any of the methods, the additional therapeutic agent is a glucocorticoid. In some embodiments, the glucocorticoid is selected from the group consisting of dexamethasone, hydrocortisone, cortisone, prednisolone, prednisone, methylprednisone, triamcinolone, paramethasone, betamethasone, fludrocortisone, and pharmaceutically acceptable esters, salts, and complexes thereof. In some embodiments, the glucocorticoid is dexamethasone. In some embodiments, the glucocorticoid is a pharmaceutically acceptable ester, salt, or complex of dexamethasone. In some embodiments, the glucocorticoid is prednisone.

In some embodiments, the additional therapy further comprises an anti-AML antibody drug conjugate. In some embodiments, the anti-AML antibody drug conjugate is an anti-CD33 antibody drug conjugate, an anti-CLL1 antibody drug conjugate, and/or an anti-CD123 antibody drug conjugate. In some embodiments, the anti-CD33 antibody drug conjugate is gemtuzumab ozogamicin (also known as MYLOTARG). In some embodiments, the anti-CLL-1 antibody drug conjugate is anti-CLL-1 antibody drug conjugate (e.g., anti-CLL-1 pyrrolobenzodiazepine (PBD) antibody drug conjugate). In some embodiments, the anti-CLL-1 antibody drug conjugate is anti-CD33 antibody drug conjugate (e.g., anti-CD33 pyrrolobenzodiazepine (PBD) antibody drug conjugate). In some embodiments, the anti-CD33 antibody drug conjugate is vadastuximab talirine (also known as SGN-CD33A). In some embodiments, the anti-CD123 antibody drug conjugate is anti-CD123 antibody drug conjugate (e.g., anti-CD123 pyrrolobenzodiazepine (PBD) antibody drug conjugate). In some embodiments, the anti-CLL-1 antibody drug conjugate is described in any one of U.S. Pat. No. 8,088,378 and/or US 2014/0030280, which are hereby incorporated by reference in their entirety.

In some embodiments of any of the methods, the additional therapy comprises cancer immunotherapies. In some embodiments of any of the methods, the cancer immunotherapy comprises a PD-1 axis binding antagonist. In some embodiments of any of the methods, the cancer immunotherapy comprises a PD-1 binding antagonist. In some embodiments, the PD-1 binding antagonist is an anti-PD-1 antibody. In some embodiments, the anti-PD-1 antibody binds to human PD-1. In some embodiments, the anti-PD-1 antibody is a monoclonal antibody. In some embodiments, the anti-PD-1 antibody is MDX-1106 (also known as (BMS-936558/ONO-4538, nivolumab or OPDIVO). In some embodiments, the anti-PD-1 antibody is MK-3475 (also known as SCH 900475, pembrolizumab, lambrolizumab, or KEYTRUDA). In some embodiments, the anti-PD-1 antibody is pidilizumab (also known as CT-011).

In some embodiments of any of the methods, the cancer immunotherapy comprises a PD-L1 binding antagonist. In some embodiments, the PD-L1 binding antagonist is an anti-PD-L1 antibody. In some embodiments, the anti-PD-L1 antibody binds to human PD-L1. In some embodiments, the anti-PD-L1 antibody is a monoclonal antibody. Examples of anti-PD-L1 antibodies that can be used in the methods described herein are described in PCT patent application WO 2010/077634 A1 and U.S. Pat. No. 8,217,149, which are incorporated herein by reference in their entirety. Further examples of anti-PD-L1 antibodies that can be used in the methods described herein are described in PCT patent application WO 2007/005874, WO 2011/066389, and US 2013/034559, which are incorporated herein by reference in their entirety.

In some embodiments, an anti-PD-L1 antibody is capable of inhibiting binding between PD-L1 and PD-1 and/or between PD-L1 and B7-1. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

Anti-PD-L1 antibodies described in WO 2010/077634 A1 and U.S. Pat. No. 8,217,149 may be used in the methods described herein. In some embodiments, the anti-PD-L1 antibody is BMS-936559. In some embodiments, the anti-PD-L1 antibody is MED14736. In some embodiments, the anti-PD-L1 antibody is MPDL3280A (CAS Registry Number 1380723-44-3). In certain embodiments, the anti-PD-L1 antibody comprises a heavy chain variable region sequence of SEQ ID NO:94 and a light chain variable region sequence of SEQ ID NO:95. In a still further embodiment, provided is an isolated anti-PD-L1 antibody comprising a heavy chain variable region and/or a light chain variable region sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 94)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS, and
(b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 95)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In one embodiment, the anti-PD-L1 antibody comprises a heavy chain variable region comprising an HVR-H1, HVR-H2 and HVR-H3 sequence, wherein:
(a) the HVR-H1 sequence is GFTFSX$_1$SWIH (SEQ ID NO:96);
(b) the HVR-H2 sequence is AWIX$_2$PYGGSX$_3$YYADSVKG (SEQ ID NO:97); and
(c) the HVR-H3 sequence is RHWPGGFDY (SEQ ID NO:98);
further wherein: X$_1$ is D or G; X$_2$ is S or L; X$_3$ is T or S.
In one specific aspect, X$_1$ is D; X$_2$ is S and X$_3$ is T, such that
(a) the HVR-H1 sequence is GFTFSDSWIH (SEQ ID NO:99);
(b) the HVR-H2 sequence is AWISPYGGSTYY-ADSVKG (SEQ ID NO:100); and
(c) the HVR-H3 sequence is RHWPGGFDY (SEQ ID NO:98);
In another aspect, the heavy chain polypeptide is further combined with a variable region light chain comprising an HVR-L1, HVR-L2 and HVR-L3, wherein:
(a) the HVR-L1 sequence is RASQX$_4$X$_5$X$_6$TX$_7$X$_8$A (SEQ ID NO:101);
(b) the HVR-L2 sequence is SASX$_9$LX$_{10}$S, (SEQ ID NO:102); and
(c) the HVR-L3 sequence is QQX$_{11}$X$_{12}$X$_{13}$X$_{14}$PX$_{15}$T (SEQ ID NO:103);
wherein: X$_4$ is D or V; X$_5$ is V or I; X$_6$ is S or N; X$_7$ is A or F; X$_8$ is V or L; X$_9$ is F or T; X$_{10}$ is Y or A; X$_{11}$ is Y, G, F, or S; X$_{12}$ is L, Y, F or W; X$_{13}$ is Y, N, A, T, G, F or I; X$_{14}$ is H, V, P, T or I; X$_{15}$ is A, W, R, P or T. In a still further aspect, X$_4$ is D; X$_5$ is V; X$_6$ is S; X$_7$ is A; X$_8$ is V; X$_9$ is F; X$_{10}$ is Y; X$_{11}$ is Y; X$_{12}$ is L; X$_{13}$ is Y; X$_{14}$ is H; X$_{15}$ is A, such that
(a) the HVR-L1 sequence is RASQDVSTAVA (SEQ ID NO:104);
(b) the HVR-L2 sequence is SASFLYS, (SEQ ID NO:105); and
(c) the HVR-L3 sequence is QQYLYHPAT (SEQ ID NO:106).

Thus, in certain embodiments, an anti-PD-L1 antibody comprises a heavy chain variable region comprising the following HVR-H1, HVR-H2 and HVR-H3 sequences, and comprises a light chain variable region comprising the following HVR-L1, HVR-L2 and HVR-L3 sequences:
(a) the HVR-H1 sequence is GFTFSDSWIH (SEQ ID NO:99);
(b) the HVR-H2 sequence is AWISPYGGSTYY-ADSVKG (SEQ ID NO:100);
(c) the HVR-H3 sequence is RHWPGGFDY (SEQ ID NO:98);
(d) the HVR-L1 sequence is RASQDVSTAVA (SEQ ID NO:104);
(e) the HVR-L2 sequence is SASFLYS, (SEQ ID NO:105); and
(f) the HVR-L3 sequence is QQYLYHPAT (SEQ ID NO:106).

In some embodiments of any of the methods, the cancer immunotherapy therapy comprises a PD-L2 binding antagonist. In some embodiments, the cancer immunotherapy comprises a PD-L2/IgG1 fusion protein (AMP-224).

In some embodiments, the cancer immunotherapy comprises an agonist directed against an activating co-stimulatory molecule. In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, the cancer immunotherapy comprises an antagonist directed against an inhibitory co-stimulatory molecule. In some embodiments, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, TIM-3, BTLA, VISTA, LAG-3 (e.g., LAG-3-IgG fusion protein (IMP321)), B7-H3, B7-H4, IDO, TIGIT, MICA/B, or arginase.

In some embodiments of any of the methods, the cancer immunotherapy comprises CTLA-4 (also known as CD152) inhibition. In some embodiments, the cancer immunotherapy comprises a CTLA-4 antagonist. In some embodiments, the CTLA-4 antagonist is an anti-CTLA-4 antibody. In some embodiments, the anti-CTLA-4 antibody is ipilimumab (also known as MDX-010, MDX-101, or Yervoy®). In some embodiments, the anti-CTLA-4 antibody is tremelimumab (also known as ticilimumab or CP-675,206).

In some embodiments, the cancer immunotherapy comprises an antagonist directed against B7-H3 (also known as CD276), e.g., a blocking antibody. In some embodiments, the cancer immunotherapy comprises MGA271 (also known as enoblituzumab).

In some embodiments, the cancer immunotherapy comprises an antagonist directed against a TGF beta, e.g., metelimumab (also known as CAT-192), fresolimumab (also known as GC1008), or LY2157299. In some embodiments of any of the methods, the cancer immunotherapy comprises immune agonists.

In some embodiments, the additional therapy comprises adoptive transfer of a T cell (e.g., a cytotoxic T cell or CTL) expressing a chimeric antigen receptor (CAR) (e.g, CAR T cell). In some embodiments, the additional therapy comprises a CAR T cell directed against WT1. In some embodiments, the CAR T cell directed against WT1 is WT128z. In some embodiments, the additional therapy comprises a CART cell directed against LeY. In some embodiments, the additional therapy comprises a CART cell directed against CD33. In some embodiments, the additional therapy comprises a CAR T cell directed against CD123. In some embodiments, the additional treatment comprises adoptive transfer of a T cell comprising a dominant-negative TGF beta receptor, e.g, a dominant-negative TGF beta type II receptor.

In some embodiments, the additional therapy comprises an antagonist directed against CD47. In some embodiments, the antagonist directed against CD47 is an anti-CD47 antibody. In some embodiments, the anti-CD47 antibody is Hu5F9-G4.

In some embodiments, the additional therapy comprises an agonist directed against CD137 (also known as TNFRSF9, 4-1BB, or ILA), e.g., an activating antibody. In some embodiments, the additional therapy comprises urelumab (also known as BMS-663513). In some embodiments, the additional therapy comprises an agonist directed against CD40, e.g., an activating antibody. In some embodiments, the additional therapy comprises CP-870893 or RO7009789. In some embodiments, the additional therapy comprises an agonist directed against OX40 (also known as CD134), e.g., an activating antibody. In some embodiments the additional therapy comprises an agonist directed against CD27, e.g., an activating antibody. In some embodiments, the additional therapy comprises CDX-1127 (also known as varlilumab). In some embodiments, the additional therapy comprises an antagonist directed against indoleamine-2,3-dioxygenase (IDO). In some embodiments, the IDO antagonist is GDC-0919 (also known as NLG919 and RG6078). In some embodiments, the IDO antagonist is 1-methyl-D-tryptophan (also known as 1-D-MT). In some embodiments, the IDO antagonist is an IDO antagonist shown in WO2010/005958 (the contents of which are expressly incorporated by record herein). In some embodiments the IDO antagonist is 4-({2-[(Aminosulfonyl)amino]ethyl}amino)-N-(3-bromo-4-fluorophenyl)-N'-hydroxy-1,2,5-oxadiazole-3-carboximidamide (e.g., as described in Example 23 of WO2010/005958). In some embodiments the IDO antagonist is

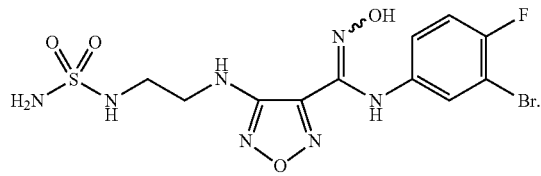 [SMILES: NS(=O)(=O)NCCNc1nonc1C(=NO)Nc1ccc(F)c(Br)c1]

In some embodiments, the IDO antagonist is INCB24360. In some embodiments, the IDO antagonist is Indoximod (the D isomer of 1-methyl-tryptophan).

In some embodiments, the additional therapy comprises an antineoplastic agent. In some embodiments, the additional therapy comprises an agent targeting CSF-1R (also known as M-CSFR or CD115). In some embodiments, the additional therapy comprises an anti-CSF-1R antibody (also known as IMC-CS4 or LY3022855) In some embodiments, the additional therapy comprises an anti-CSF-1R antibody, RG7155 (also known as RO5509554 or emactuzumab). In some embodiments the additional therapy comprises an interferon, for example interferon alpha or interferon gamma. In some embodiments, the additional therapy comprises Roferon-A (also known as recombinant Interferon alpha-2a). In some embodiments, the additional therapy comprises GM-CSF (also known as recombinant human granulocyte macrophage colony stimulating factor, rhu GM-CSF, sargramostim, or Leukine®). In some embodiments, the additional therapy comprises IL-2 (also known as aldesleukin or Proleukin®). In some embodiments, the additional therapy comprises IL-12. In some embodiments, the additional therapy comprises IL27. In some embodiments, the additional therapy comprises IL-15. In some embodiments, the additional therapy comprises ALT-803. In some embodiments the additional therapy comprises an antibody targeting GITR. In some embodiments, the antibody targeting GITR is TRX518. In some embodiments, the antibody targeting GITR is MK04166 (Merck).

In some embodiments, the additional therapy comprises an inhibitor of Bruton's tyrosine kinase (BTK). In some embodiments, the additional therapy comprises ibrutinib. In some embodiments, the additional therapy comprises an inhibitor of Isocitrate dehydrogenase 1 (IDH1) and/or Isocitrate dehydrogenase 2 (IDH2). In some embodiments, the additional therapy comprises AG-120 (Agios).

In some embodiments, the additional therapy comprises a cancer vaccine. In some embodiments, the cancer vaccine is a personalized cancer vaccine. In some embodiments, the cancer vaccine is a peptide cancer vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, the cancer vaccine is a DNA-based cancer vaccine. In some embodiments, the DNA-based cancer vaccine comprises naked DNA. In some embodiments, the DNA-based cancer vaccine comprises cells transfected with DNA. In some embodiments, the cells are dendritic cells. In some embodiments, the cancer vaccine is an RNA-based cancer vaccine. In some embodiments, the RNA-based cancer vaccine is an mRNA-based cancer vaccine. In some embodiments, the mRNA-based cancer vaccine comprises naked RNA. In some embodiments, the RNA-based cancer vaccine comprises cells transfected with RNA. In some embodiments, the RNA is coated on particles. In some embodiments, the RNA is transfected in dendritic cells in vitro. In some embodiments, the mRNA is tailored to act as an adjuvant to stimulate the innate immune system. In some embodiments, the cancer vaccine comprises an adjuvant. In some embodiments, the adjuvant comprises a TLR agonist, e.g., Poly-ICLC (also known as Hiltonol®), LPS, MPL, or CpG ODN. In some embodiments, the cancer vaccine comprises a liposome.

In some embodiments, the additional therapy comprises an IL-10 antagonist. In some embodiments, the additional therapy comprises an IL-4 antagonist. In some embodiments, the additional therapy comprises an IL-13 antagonist. In some embodiments, the additional therapy comprises an IL-17 antagonist. In some embodiments, the additional therapy comprises an HVEM antagonist. In some embodiments, the additional therapy comprises an ICOS agonist, e.g., by administration of ICOS-L, or an agonistic antibody directed against ICOS. In some embodiments, the additional therapy comprises a treatment targeting CX3CL1. In some embodiments, the additional therapy comprises a treatment targeting CXCL9. In some embodiments, the additional therapy comprises a treatment targeting CXCL10. In some embodiments, the additional therapy comprises a treatment targeting CCL5. In some embodiments, the additional therapy comprises an LFA-1 or ICAM1 agonist. In some embodiments, the additional therapy comprises a Selectin agonist.

In some embodiments, the additional therapy comprises an inhibitor of a MEK, such as MEK1 (also known as MAP2K1) and/or MEK2 (also known as MAP2K2). In some embodiments, the additional therapy comprises cobimetinib (also known as GDC-0973 or XL-518). In some embodiments, the additional therapy comprises trametinib (also known as Mekinist®). In some embodiments, the additional therapy comprises binimetinib.

In some embodiments, the additional therapy comprises a delta-selective inhibitor of a phosphatidylinositol 3-kinase (PI3K). In some embodiments, the additional therapy comprises idelalisib (also known as GS-1101 or CAL-101). In some embodiments, the additional therapy comprises taselisib (also known as GDC-0032). In some embodiments, the additional therapy comprises BYL-719.

In some embodiments, the additional therapy comprises an inhibitor of LSD1 (also known as KDM1A). In some embodiments, the additional therapy comprises ORY-1001. In some embodiments, the additional therapy comprises GSK2879552.

In some embodiments, the additional therapy comprises an inhibitor of MDM2. In some embodiments, the additional therapy comprises RG7112. In some embodiments, the additional therapy comprises idasanutlin (also known as RG7388 or RO5503781). In some embodiments, the additional therapy comprises DS-3032b. In some embodiments, the additional therapy comprises SAR405838. In some embodiments, the additional therapy comprises CGM-097. In some embodiments, the additional therapy comprises MK-8242. In some embodiments, the additional therapy comprises AMG-232.

In some embodiments, the additional therapy comprises an inhibitor of BCL2. In some embodiments, the additional therapy comprises venetoclax.

In some embodiments, the additional therapy comprises an inhibitor of CHK1. In some embodiments, the additional therapy comprises GDC-0575 (also known as ARRY-575). In some embodiments, the additional therapy comprises GDC-0425 (also known as RG7602). In some embodiments, the additional therapy comprises LY2606368.

In some embodiments, the additional therapy comprises an inhibitor of activated hedgehog signaling pathway. In some embodiments, the additional therapy comprises ERIVEDGE.

In some embodiments, the additional therapy comprises an agent that recruits T cells to the tumor. In some embodiments, the additional therapy comprises lirilumab (IPH2102/BMS-986015). In some embodiments, the additional therapy comprises Idelalisib.

Such combination therapies noted above encompass combined administration (where two or more therapeutic agents are included in the same or separate formulations), and separate administration, in which case, administration of a CLL-1/CD3 TDB antibody can occur prior to, simultaneously, and/or following, administration of the additional therapeutic agent and/or adjuvant.

In some embodiments of any of the methods, an antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In some embodiments, the administration is subcutaneous.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-CLL-1 antibody (e.g., anti-CLL-1/CD3 TDB antibody) administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-CLL-1 antibody (e.g., anti-CLL-1/CD3 TDB antibody) described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-CLL-1 antibody (e.g., anti-CLL-1/CD3 TDB antibody). An initial higher loading dose, followed by one or more lower doses may be administered. The progress of this therapy is easily monitored by conventional techniques and assays.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an anti-CLL-1 antibody wherein the antibody comprises a CLL-1 binding domain of the invention and a CD3 binding domain. In some embodiments, the anti-CLL-1 antibody is a bispecific antibody.

III. Examples

The following are examples of methods and compositions of the invention. It is understood that various other embodiments may be practiced, given the general description provided above.

Example 1—Anti-CLL-1 Antibody

A. Monoclonal Antibody Generation

Monoclonal antibodies against human (hu) and cynomolgus (cyno) CLL-1 were generated using the following procedures by immunizing animals with recombinant hu and cyno CLL-1 extracellular domain (ECD, amino acids of 65-265 huCLL-1 and 65-265 cynoCLL-1) fused to a N-terminal Flag (DYKDDDDK (SEQ ID NO: 108)) expressed in a mammalian expression system. The huCLL1 ECD protein (amino acids 65-265) comprised a SNP, AAA(Lys, K) 244→CAA (GLN, Q), which has a minor allele frequency (MAF) of 29%.

Figure 1A:
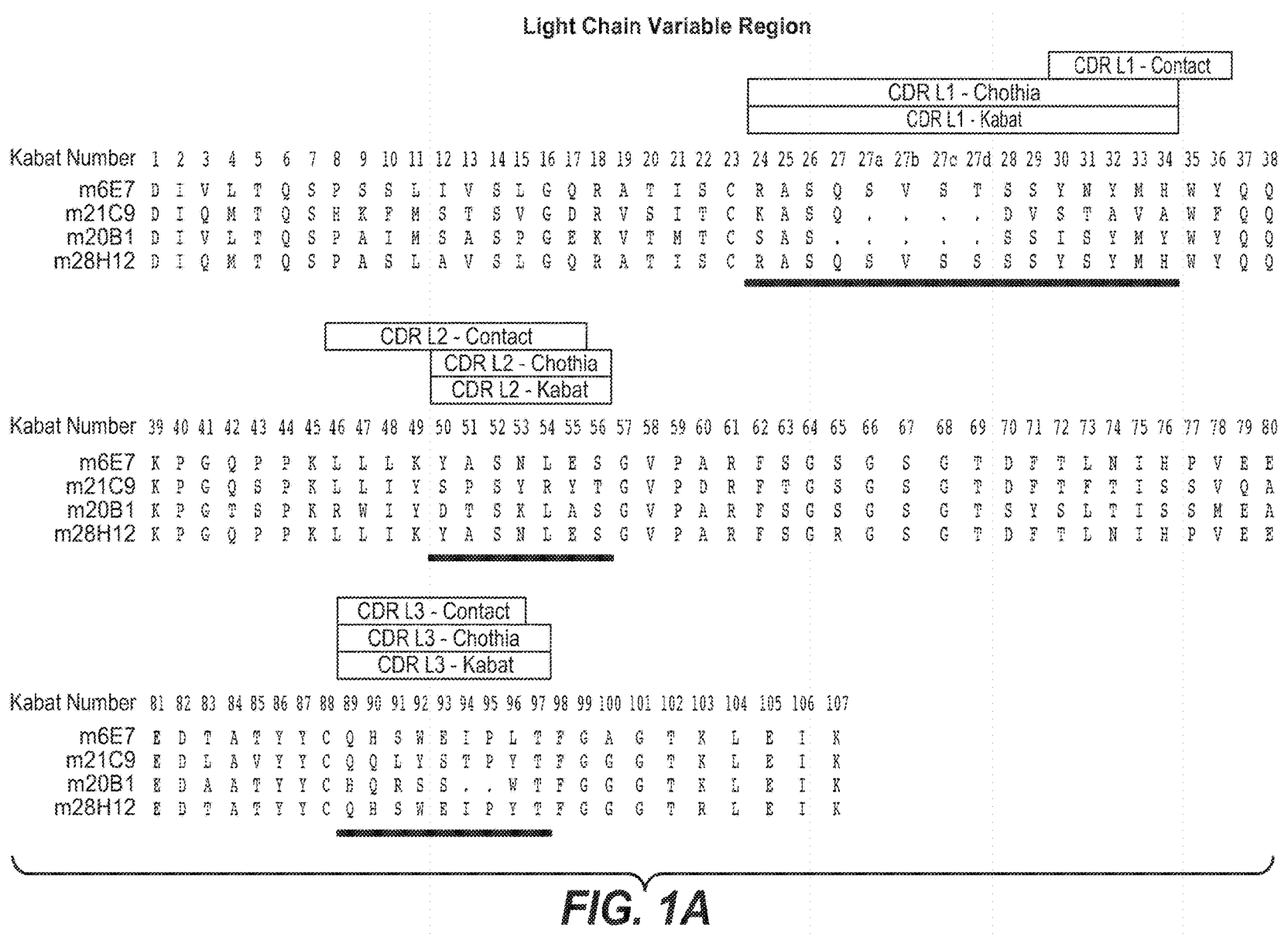
Figure 1B:
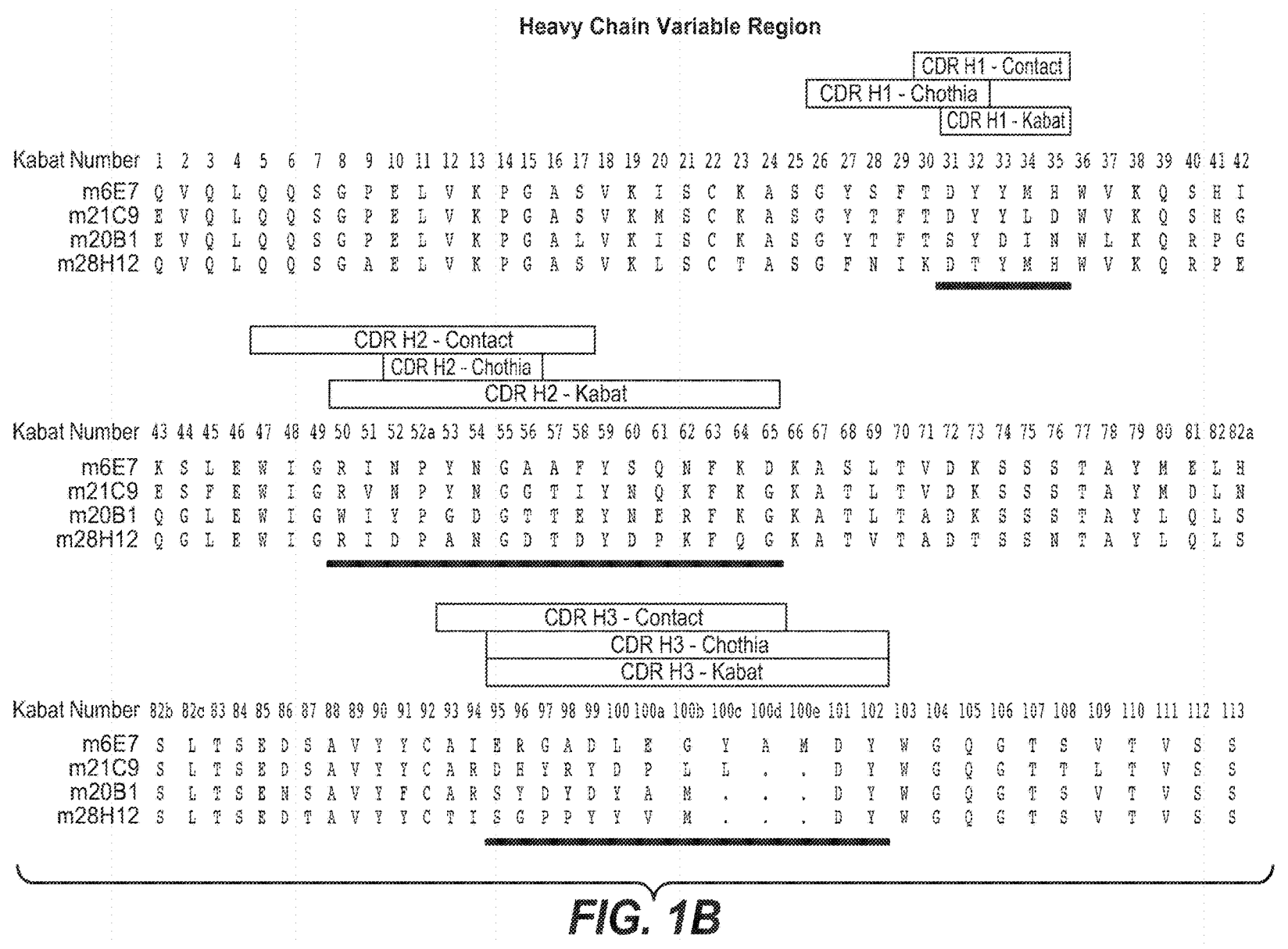

Positive clones were expanded and re-screened for binding to huCLL-1 and cynoCLL-1 by ELISA and FACS. Five clones were identified: m3H10, m6E7, m20B1, m21C9, and m28H12 that reacted strongly by fluorescent activated cell sorting (FACS) with stable cell lines expressing recombinant hu and cyno CLL-1, and with tumor-derived CLL-1 expressed on Acute Myeloid Leukemia tumor cell lines. Alignment of the amino acid sequences of the murine heavy and light variable domains are shown in FIGS. 1A and B. m3H10 and m21C9 share the same heavy and light chain CDRs, only the amino acid sequences of m21C9 heavy and light chain variable region is shown in FIG. 1.

B. Species Cross-Reactivity and Binding Affinity

Monoclonal antibodies were tested to determine if they cross-react with cynoCLL-1 extra-cellular domain (ECD) (which is 85.07% identical and 87.35% similar to the huCLL-1 protein ECD). The chimeric anti-CLL-1 human IgG were captured by mouse anti-human IgG coated on the CM5 sensor chip. For kinetics measurements, three-fold serial dilutions of human or cyno CLL-1 (4.1 nM to 1000 nM) were injected in HBS-EP buffer. Association rates (kon) and dissociation rates (koff) were calculated using a simple one-to-one Langmuir binding model. The equilibrium dissociation constant (KD) was calculated as the ratio koff/kon. Table 2 below shows that the chimeric version of the five antibodies (m3H10, m6E7, m20B1, m21C9, and m28H12) recognized both recombinant hu and cynoCLL-1 and provides details regarding the kinetics of the interaction with hu and cyno-CLL-1. Further confirmation of cross-reactivity to cyno CLL-1 was done by FACS analyses of blood from cynomolgus (Mauritian origin) (data not shown).

TABLE 2

Biacore of Anti-CLL-1 Antibodies

| Ligand | Analyte | Ka ($M^{-1}s^{-1}$) | Kd ($s^{-1}$) | KD (M) |
|---|---|---|---|---|
| ch3H10 | huCLL-1-Flag | $2.7 \times 10^5$ | $2.4 \times 10^{-3}$ | 8.7 nM |
|  | CynoCLL-1 Flag | $1.7 \times 10^5$ | $7.7 \times 10^{-4}$ | 4.3 nM |
| ch6E7 | huCLL-1-Flag | $4.6 \times 10^5$ | $4.4 \times 10^{-4}$ | 0.9 nM |
|  | CynoCLL-1 Flag | $4.0 \times 10^5$ | $4.6 \times 10^{-4}$ | 1.1 nM |
| ch20B1 | huCLL-1-Flag | $2.2 \times 10^5$ | $1.0 \times 10^{-3}$ | 4.5 nM |
|  | CynoCLL-1 Flag | $1.9 \times 10^5$ | $1.2 \times 10^{-3}$ | 6.1 nM |
| ch21C9 | huCLL-1-Flag | $2.5 \times 10^5$ | $2.4 \times 10^{-3}$ | 9.7 nM |
|  | CynoCLL-1 Flag | $1.6 \times 10^5$ | $1.2 \times 10^{-3}$ | 7.1 nM |
| ch28H12 | huCLL-1-Flag | $5.0 \times 10^5$ | $9.5 \times 10^{-3}$ | 18 nM |
|  | CynoCLL-1 Flag | $6.7 \times 10^5$ | $2.3 \times 10^{-4}$ | 0.3 nM |

Scatchard analysis was performed following standard procedures (Holmes et al., *Science* 256:1205-1210 (1992)) to determine the relative binding affinities of the antibodies including ch6E7 and ch21C9.

Anti-CLL-1 antibodies were [$I^{125}$] labeled using the indirect Iodogen method. The [$I^{125}$] labeled anti-CLL-1 antibodies were purified from free $^{125}$I-Na by gel filtration using a NAP-5 column (GE Healthcare); the purified iodinated anti-CLL-1 antibodies had a range of specific activities of 8-10 μCi/μg. Competition assay mixtures of 50 μL volume containing a fixed concentration of [$I^{125}$] labeled antibody and decreasing concentrations of serially diluted, unlabeled antibody were placed into 96-well plates. HEK293AD cells stably expressing recombinant hu or cynoCLL-1 or HL-60 tumor cells expressing endogenous CLL-1 were cultured in growth media at 37° C. in 5% $CO_2$. Cells were detached from the flask using Sigma Cell Dissociation Solution and were washed with binding buffer, which consisted of Dulbecco's Modified Eagle Medium (DMEM) with 1% bovine serum albumin (BSA), 300 mM human IgG and 0.1% sodium azide. The washed cells were added to the 96 well plates at a density of 100,000 cells in 0.2 mL of binding buffer. The final concentration of the [$I^{125}$] labeled antibody in each well was ~250 pM. The final concentration of the unlabeled antibody in the competition assay ranged from 1000 nM through ten 2-fold dilution steps to a 0 nM buffer-only assay. Competition assays were carried out in triplicate. Competition assays were incubated for 2 hours at room temperature. After the 2-hour incubation, the competition assays were transferred to a Millipore Multiscreen filter plate (Billerica, Mass.) and washed 4 times with binding buffer to separate the free from bound [$I^{125}$] labeled antibody. The filters were counted on a Wallac Wizard 1470 gamma counter (PerkinElmer Life and Analytical Sciences Inc.; Wellesley, Mass.). The binding data was evaluated using NewLigand software (Genentech), which uses the fitting algorithm of Munson and Robard to determine the binding affinity of the antibody (Munson and Robard 1980).

Table 3 shows the affinity (kD range of 0.45-1.2 nM) to recombinant hu and cynoCLL-1 expressed by HEK293AD CLL-1 stable cells and to HL-60 cells.

TABLE 3

Antibody Affinity [kD = nM] to CLL-1 (Scatchard Analysis).

| Cells | | ch6E7 | ch21C9 |
|---|---|---|---|
| HL-60 | $K_D$ (nM) | 0.65 | 0.45 |
| EOL-1 | $K_D$ (nM) | | |
| 293AD/huCLL-1 | $K_D$ (nM) | 0.80 | 0.59 |
| 293AD/cynoCLL-1 | $K_D$ (nM) | 1.0 | 1.2 |

C. Monoclonal Antibody Epitope Grouping

Epitope grouping was also determined using a cell-based competition binding FACS assay. HL-60 cells were pre-incubated with or without 50-100 fold excess of unlabeled competing antibodies, then stained with directly labeled detection antibodies, a reduction of the signal from detecting antibody indicating that the unlabeled competing antibody binds to the same or similar region on CLL-1 as the detecting antibody—this should occur when the same antibody is used as both detector and competitor. When there is no blocking of detector signal by a different unlabeled antibody, the unlabeled antibody is binding to a different region in CLL-1.

TABLE 4

Anti-CLL-1 Competition Experiments

| | Competing antibodies | | | | |
|---|---|---|---|---|---|
| Detecting antibodies | ch6E7 | ch20B1 | ch21C9 | ch28H12 | R&D |
| R&D Systems-PE (Clone 687317) | ✓ | X | ✓ | X | ✓ |
| ch6E7-DyLight650 | ✓ | X | n/a | X | n/a |
| ch28H12-DyLight650 | n/a | X | n/a | ✓ | n/a |
| ch21C9-DyLight650 | ✓ | X | ✓ | X | ✓ |
| eBioscience HB3-PE | X | X | X | X | ✓ |
| BD Biosciences 50C1-PE | X | X | X | X | X |

Table 4 shows epitope grouping of the antibodies to CLL-1. ch6E7 and ch21C9, but not ch20B1 and ch28H12, bin with R&D Systems-PE (Clone 687317). R&D Systems also blocked eBioscience clone HB3, but ch6E7 and ch21C9 were unable to block eBioscience clone HB3 binding. ch20B1 and ch28H12 failed to compete with any other antibody suggesting each antibody binds a distinct epitope. All antibodies failed to compete with BD Biosciences clone 50C1 also suggesting that it binds a distinct epitope.

D. Humanization of Anti-CLL-1 Antibodies

Monoclonal antibody 6E7 and 21C9 was humanized as described below. Residue numbers are according to Kabat et al., Sequences of proteins of immunological interest, 5th Ed., Public Health Service, National Institutes of Health, Bethesda, Md. (1991).

Variants constructed during the humanization of 6E7 and 21C9 were assessed in the form of an IgG. The VL and VH domains from murine 6E7 and 21C9 were aligned with the human VL kappa I (VLKI) and human VH subgroup I (VHI) consensus sequences. Hypervariable regions from the murine antibodies were engineered into VLKI and VHI acceptor frameworks. Specifically, from the mu6E7 and mu21C9 VL domain, positions 24-34 (L1), 50-56 (L2) and 89-97 (L3) were grafted into VLKI and from the mu6E7 and mu21C9 VH domain, positions 26-35 (H1), 50-65 (H2) and 93-102 (H3) were grafted into VHI.

The binding affinity of the antibodies in this section was determined by BIAcore™ T200 Format. Briefly, BIAcore™ research grade CM5 chips were activated with 1-ethyl-3-(3-dimethylaminopropyl) carbodiimide (EDC) and N-hydroxysuccinimide (NHS) reagents according to the supplier's instructions. Goat anti-human Fc IgGs were coupled to the chips to achieve approximately 10,000 response units (RU) in each flow cell. Unreacted coupling groups were blocked with 1M ethanolamine. For kinetics measurements, antibodies were captured to achieve approximately 300 RU. Threefold serial dilutions of human CLL-1 was injected in HBS-P buffer (0.01M HEPES pH7.4, 0.15M NaCl, 0.005% surfactant P20) at 25° C. with a flow rate of 30 µl/min. Association rates (kon) and dissociation rates (koff) were calculated using a 1:1 Langmuir binding model (BIAcore™ T200 Evaluation Software version 2.0). The equilibrium dissociation constant (Kd) was calculated as the ratio koff/kon.

The binding affinity of the CDR graft humanized 6E7 antibody was compared to chimeric 6E7. Additional variants of the CDR graft humanized 6E7 antibody were made to evaluate the contribution of other vernier positions to binding to CLL-1. For 6E7, initially four additional light chains (L1: CDRs graft+(L4, L48, and K49), L2: CDRs graft+L4, L3: CDRs graft+K49, and L4: CDRs graft+K49) and five additional heavy chains (H1: CDRs graft+(A67, L69, V71, K73), H2: CDRs graft+A67, H3: CDRs graft+L69, H4:CDRs graft+V71, and H5: CDRs graft+K73). K49 on the light chain was the key mouse vernier residue, and L69 and V71 on the heavy chain were determined to be the key mouse vernier residues based on mutational analysis (data not shown). Chimeric 6E7 bound with a KD of 9.59E-10 M, while CDRs graft+K49(LC)+(A67, L69, V71, K73 (HC)), CDRs graft+K49(LC)+(L69, V71 (HC)) bound with a KD of 1.40E-9M, and 1.37E-9M, respectively.

The binding affinity of the CDR graft humanized 21C9 antibody was compared to chimeric 21C9 antibody. Additional variants of the CDR graft humanized 21C9 antibody were made to evaluate the contribution of other vernier positions to binding to CLL-1. For 21C9, initially three additional light chains (L1: CDRs graft+(F36 and S43), L2: CDRs graft+F36, L3: CDRs graft+S43) and five additional heavy chains (H1: CDRs graft+(A67, L69, V71, K73), H2: CDRs graft+A67, H3: CDRs graft+L69, H4:CDRs graft+V71, and H5: CDRs graft+K73). F36 on the light chain was the key mouse vernier residue. Chimeric 21C9 bound with a KD of 8.615E-9 M, while CDRs graft+(F36 and S43 (LC))+L69 (HC) and CDRs graft+F36 (LC)+L69 (HC), bound with a KD of 1.053E-8M and 9.785-9M, respectively. L69 on the heavy chain were determined to be the key mouse vernier residues.

The humanized 6E7.L4H1e and 21C9.L2H3 were tested for their ability to bind human and cyno CLL-1 as described above except that cynoCLL-1 replaced huCLL-1 in the cyno binding assay. Binding properties for the humanized antibodies are shown below in Table 5. The binding affinity of the humanized 6E7.L4H1e was 0.34, 0.29, 0.22, and 0.35 Kd (nM) as determined by Scatchard using HL-60, EOL-1, 293AD/cynoCLL1, and 293AD/huCLL-1 cells, respectively. The binding affinity of humanized 21C9.L2H3 was 1.3, 0.74, 2.4, and 3.6 Kd (nM) as determined by Scatchard using HL-60, EOL-1, 293AD/cynoCLL1, and 293AD/huCLL-1 cells, respectively.

For the humanized 6E7.L4H1e CDR-H2 N54 antibody variants, A54 had acceptable binding characteristics which were most similar to N54. For the humanized 21C9.L2H3 CDR-H2 N54 antibody variants, all the variants showed a drop in affinity to huCLL-1 in off-rate (10-30 fold) and cynoCLL-1 in on rate (60-500 fold). The binding affinity of the humanized 6E7.L4H1e was 0.67, 0.68, 0.6, and 0.25 Kd (nM) as determined by Scatchard using 293AD/cynoCLL1, 293AD/huCLL-1, HL-60, and EOL-1 cells, respectively. The binding affinity of humanized 6E7.L4H1eN54A was 0.9, 0.89, 0.64, and 0.32 Kd (nM) as determined by Scatchard using 293AD/cynoCLL1, 293AD/huCLL-1, HL-60, and

TABLE 5

| Antibody | huKD (M) | huka (1/Ms) | hukd (1/s) | cynoKD (M) | cynoka (1/Ms) | cynokd (1/s) |
|---|---|---|---|---|---|---|
| 6E7.L4H1e | 6.218E−10 | 8.236E+5 | 5.121E−4 | 3.170E−10 | 7.391E+5 | 2.343E−4 |
| 21C9.L2H3 | 1.171E−8 | 2.244E+5 | 2.628E−3 | 9.472E−9 | 1.683E+5 | 1.594E−3 |

The humanized antibodies 6E7.L4H1e and 21C9.L2H3 were tested under thermal stress (40° C., pH 5.5, 2 weeks) and 2,2'-azobis (2-amidinopropane) hydrochloride (AAPH) Analysis. Samples were thermally stressed to mimic stability over the shelf life of the product. Samples were buffer exchanged into 20 mM His Acetate, 240 mM sucrose, pH 5.5 and diluted to a concentration of 1 mg/mL. One mL of sample was stressed at 40C for 2 weeks and a second was stored at −70C as a control. Both samples were then digested using trypsin to create peptides that could be analysed using liquid chromatography(LC)-mass spectrometry(MS) analysis. For each peptide in the sample retention time, from the LC as well as high resolution accurate mass and peptide ion fragmentation information (amino acid sequence information) were acquired in the MS. Extracted ion chromatograms (XIC) were taken for peptides of interest (native and modified peptide ions) from the data sets at a window of +−10 ppm and peaks were integrated to determine area. Relative percentages of modification were calculated for each sample by taking the (area of the modified peptide) divided by (area of the modified peptide plus the area of the native peptide) multiplied by 100.

Both 6E7.L4H1e and h21C9.L2H3 have $N^{54}G^{55}$ in DR-H2, which is susceptible to deamination (t0=13.2% and t2 wk 14.5% for 6E7.L4H1e and r0=11% and t2 wk=11.9%). N54 variants of both antibodies were tested to determine if potential deamination could be reduced without affecting binding to hu and cynoCLL-1. See Table 6.

EOL-1 cells, respectively. Alignment of the heavy and light variable domain amino acid sequences of humanized 6E7 and 21C9 antibodies are shown in FIG. 2A-B and FIG. 3A-B, respectively.

E. Epitope Mapping

To determine the binding epitope of the CLL-1, examination of (a) free antigen CLL-1 and (b) three different antigen-mAb complexes using hydroxyl radical footprinting (HRF) techniques was performed. The samples were exposed to hydroxyl radicals for intervals of 0, 10, 15, and 20 milliseconds (ms) using the X28c Beam line at the Brookhaven National Laboratory. The labeled samples were subjected to deglycosylation using PNGase F. A pilot experiment was first carried out on the deglycosylated samples for optimizing the experimental protocol. The pilot investigation using MS revealed that the samples contained significant amount of polymer contamination, requiring additional clean up. In order to remove the polymer contamination, the samples were precipitated using Trichloroacetic acid in acetone, and subjected to LC-MS analysis. The precipitation step was successful, and the polymer contamination signal in the MS was significantly attenuated. The cleaned samples were subjected to reduction and alkylation, digestion using Trypsin, followed by liquid chromatography coupled with high-resolution mass spectrometry (LC-MS). The MS data was analyzed using ProtMapMS, resulting in dose response plots for each peptide. Results from the free antigen were compared against each of the complex forms. A homology-

TABLE 6

| Antibody | huKD (M) | huka (1/Ms) | hukd (1/s) | cynoKD (M) | cynoka (1/Ms) | cynokd (1/s) |
|---|---|---|---|---|---|---|
| 6E7.L4H1eN54 | 1.082E−9 | 9.096E+5 | 9.837E−4 | 2.256E−9 | 8.044E+5 | 1.815E−3 |
| 6E7.L4H1eA54 | 3.082E−9 | 7.103E+5 | 2.189E−3 | 3.143E−9 | 6.087E+5 | 1.913E−3 |
| 6E7.L4H1eE54 | 5.090E−9 | 4.882E+5 | 2.485E−3 | 4.256E−9 | 6.641E+5 | 2.827E−3 |
| 6E7.L4H1eS54 | 1.413E−8 | 5.098E+5 | 7.205E−3 | 6.371E−9 | 5.133E+5 | 3.270E−3 |
| 6E7.L4H1eD54 | 1.132E−7 | 3.044E+5 | 3.444E−2 | 4.870E−8 | 1.785E+5 | 8.694E−3 |
| 21C9.L2H3N54 | 1.510E−8 | 1.889E+5 | 2.853E−3 | 9.302E−9 | 2.358E+5 | 2.194E−3 |
| 21C9.L2H3S54 | 2.859E−7 | 1.416E+5 | 4.047E−2 | 5.669E−6 | 3656 | 2.072E−2 |
| 21C9.L2H3A54 | 6.215E−7 | 1.113E+5 | 6.915E−2 | 4.818E−5 | 445.3 | 2.146E−2 |
| 21C9.L2H3E54 | 8.625E−7 | 1.022E+5 | 8.816E−2 | 4.961E−5 | 747.5 | 3.709E−2 |
| 21C9.L2H3D54 | 8.017E−7 | 2.858E+5 | 2.291E−2 | 2.172E−7 | 4.072E+4 | 8.846E−3 | based model of the antigen was generated using Swiss-Model software, and the solvent protected regions were mapped for each of the three complexes.

The overall sequence coverage obtained using Trypsin mapping was 90.05%. The missing regions were comprised primarily of tryptic peptides that were shorter than 4 residues in length, which can be inherently difficult to detect due to their weak retention properties on the LC column. The HRF process introduces stable side chain oxidative modifications resulting in specific mass shifts, which were identified from the tandem mass spectrometry data. The selected ion chromatograms (SIC) were extracted and integrated for the unoxidized and all oxidized forms of peptide ion (with particular m/z). These peak area values were used to characterize reaction kinetics in the form of dose response (DR) plots, which measure the loss of intact peptide as a function of the hydroxyl radical exposure. The solvent protected regions in the complex experience gradual oxidation reaction as opposed to the free antigen. Differences in the rate of oxidation (called rate constant, RC) serve to highlight the location of the epitope.

ProtMapMS was used to process the MS data, resulting in RC values for each peptide. Final results are shown in Table 6. Peptide location and the corresponding sequence are shown in columns 1 and 2. The third column shows the protection ratio, PR (=RCAntigen/RCComplex) for complex 1 (6E7.L4H1eA54 antibody and CLL-1 antigen). Similarly, fourth and fifth columns show the corresponding protection ratios for complex 2 (21C9.L2H3 antibody engineered with a light chain comprising a cysteine residue at K149 according to Kabat numbering (K149C) and CLL-1 antigen) and complex 3 (R&D Systems monoclonal anti-CLL1 antibody (Clone 687317) and CLL-1 antigen). If the PR value for a given peptide for a particular is less than 1, the corresponding region experienced gain in solvent accessibility due to structural changes introduced during complex formation. A PR value close to 1 indicates that the solvent accessibility of the region remains unchanged, while a PR>1 suggests that the corresponding region exhibits protection from the solvent as a function of the complex formation. The PR values for most of the peptides for each complex are close to 1, indicating minimal change in solvent accessibility for the corresponding regions. Peptide 142-158 consistently shows the highest PR value for all three antibodies, implying significant protection for the region. In addition to protection of the peptide 142-158, the R&D Systems monoclonal anti-CLL1 antibody (Clone 687317, unlike 6E7.L4H1eAG and 21C9.L2H3, also showed significant protection of the region 103-116 as evidenced by the overlapping peptides 103-116 and 105-116.

TABLE 6

| Pep locn of SEQ ID NO: 1 | Sequence | SEQ ID NO: | RCA/RC1 | RCA/RC2 | RCA/RC3 |
|---|---|---|---|---|---|
| 65-69 | DYKDDDDKLEHVTLK | 52 | 1.4 | 1.0 | 1.0 |
| 68-69 | DDDDKLEHVTLK | 53 | 1.1 | 0.9 | 0.8 |
| 75-87 | MNKLQNISEELQR | 54 | 1.4 | 1.1 | 0.90 |
| 78-87 | LQNISEELQR | 55 | 1.3 | 1.0 | 0.8 |
| 88-102 | NISLQLMSNMNISNK | 56 | 1.1 | 0.5 | 0.5 |
| 103-116 | IRNLSTTLQTIATK | 50 | 1.1 | 0.8 | 2.1 |
| 105-116 | NLSTTLQTIATK | 51 | 1.2 | 1.0 | 2.2 |
| 105-119* | NLSTTLQTIATKLCR | 57 | NA | NA | NA |
| 120-124* | ELYSK | 58 | NA | NA | NA |
| 137-141 | WIWHK | 59 | 1.0 | 0.6 | 1.3 |
| 142-158 | DSCYFLSDDVQTWQESK | 49 | 3.1 | 2.0 | 3.1 |
| 159-160 | MACAAQNASLLK | 60 | 1.0 | 1.2 | 0.8 |
| 171-181 | INNKNALEFIK | 61 | 1.7 | 1.3 | 1.1 |
| 175-181 | NALEFIK | 62 | 1.3 | 1.0 | 1.3 |
| 175-185* | NALEFIKSQSR | 63 | NA | NA | NA |
| 186-201 | SYDYWLGLSPEEDSTR | 64 | 1.0 | 1.0 | 1.0 |
| 186-204* | SYDYWLGLSPEEDSTRGMR | 65 | NA | NA | NA |
| 205-117 | VDNIINSSAWVIR | 66 | 1.2 | 1.0 | 1.0 |
| 218-232 | NAPDLNNMYCGYINR | 67 | 1.2 | 1.0 | 0.9 |
| 233-243 | LYVQYYFICTYK | 68 | 1.0 | 1.1 | 1.0 |
| 246-250* | MICEK | 69 | NA | NA | NA |
| 251-263 | MANPVQLGSTYFR | 70 | 0.99 | 1.1 | 1.0 |

F. Internalization of Anti-CLL-1 Antibody

To determine whether anti-CLL-1 antibody gets internalized upon binding, HL-60 or HL-60 cells were pre-incubated for 2 hours at 37° C. with 0.3 mg/ml hIgG in RPMI medium to reduce non-specific binding to FcR before seeding in cell culture treated 4-well chamber slides (Nalge Nunc International). Antibody directly conjugated to Dylight 488 at a final concentration of 1 μg/mL was incubated with hIgG-blocked cells on ice for 30 minutes in the dark. The cells were immediately imaged to show membrane staining (TO) and followed with time-lapsed photography over a 10 hour period at 37° C. with a Leica SP5 confocal microscope. A representative example, ch21C9, is rapidly internalized within 30 minutes by HL-60 cells (data not shown). Localization of ch21C9 to the lysosome was confirmed using an in vitro cell-based assay.

Example 2: Efficacy of CLL1 T-Cell Dependent Bispecific (TDB) Antibody

The following examples show that an engineered T-cell dependent bispecific antibody comprising the binding determinants of an anti-human CLL-1 on one arm and an anti-human CD3e on the other arm is a potent immune-modulating molecule that can redirect a persons' immune system to kill Acute Myeloid Leukemia tumor cells and normal CD14+ monocytes from human donors. TDB Efficacy was demonstrated by monitoring the killing of AML tumor cell lines (EOL-1, HL-60, THP-1, U937, Nomo-1, PL-21, ML-2 and Molm-13) by untouched human CD8+ T cells or by monitoring the killing of autologous CD14+ mononuclear cell with autologous T cells in a population of human PBMCs.

The TDB used in the following examples contained the CLL-1 binding determinants from anti-CLL-1 mouse and humanized monoclonal antibody clones from three different epitope bins of 1) 6E7 and/or 21C9, 2) 2061, and 3) 28H12, and the binding determinants from a humanized anti-CD3ε clone, high affinity antibody 38E4v1 and low affinity antibody 40G5c as determined by Biacore (hCD3ε 1-27 Fc (1.0 and 13 nM respectively), hCD3εγ (0.5 and 12 nM, respectively) and cynoCD3εγ (0.7 and 14 nM, respectively) as well as very high affinity antibody 38E4v11 with a hCD3 (0.05 nM; Fab Biacore measurements to hCD3ε-5.00E+07 ka (1/Ms), 1.60E-03 kd (1/s), and 0.032 KD (nM)). Fab Biarcore measurements to hCD3ε for 38E4v1 were 8.15E+06 ka (1/Ms), 3.17E-03 kd (1/s), and 0.389 KD (nM). 38E4v1, 38E4v11, and 40G5c bind a human CD3ε polypeptide (a fragment of the human CD3ε polypeptide consisting of amino acids 1-26 (SEQ ID NO:86) or 1-27 (SEQ ID NO:87)) and amino acid residue Glu5 of CD3ε is not required for binding (data not shown; see also PCT/US14/70951, which is incorporated by reference in its entirety).

A. Materials and Methods

In all experiments, the target cells, AML tumor cell lines, PBMC, or AML patient bone marrow cells, were pre-incubated for 1-2 hours at 37° C. in RPMI medium containing 10% FCS, 2 mM Glutamine and 0.3 mg/ml purified low endotoxin human IgG (Molecular Innovations, HU-GF-ED) to prevent non-specific binding of the TDB to cells with surface expression of FcγRs. In the first example, PBMCs were isolated from normal human donors, and untouched $CD8^+$ T cells in the PBMCs were enriched using the kit from Miltenyi Biotec GmbH (Miltenyi; 130-096-495). The assay was performed in a 96-well round bottom plate (Costar 3799) containing 60,000 cells/well of human $CD8^+$ T cells and 20,000 cells/well of hIgG-blocked target cells; the effector to target ratio (E:T) was 3:1. TDB (e.g., h6E7 (6E7.L4H1e)-38E4v1, h21C9 (h21C9.L2H3)-38E4v1 or negative control anti-gD-38E4v1) was added as a 10× working solution serially diluted 3-fold to a final assay concentration spanning 0-10 ug/ml or 0-1 ug/ml. The order of addition was as follows, 50 ul of 2× target cells, 11 ul of 10×3-fold serially diluted TDB, and 50 ul of 2×$CD8^+$ T cells. The contents were mixed on a Titer Plate Shaker (Thermo) at setting 6 for 15 sec and incubated for at 37° C. for about 40 hrs. The plate was mixed once each day. Depletion of hCLL-1 expressing EOL-1, THP-1, HL-60, Nomo-1, ML-2, PL-21, U937 and Molm-13 cells were monitored using either an anti-CD123-APC (BD Pharmingen; 560087) or anti-CD33-APC reagent (BD Pharmingen; 551378) and propidium iodide by FACS. Activation of $CD8^+$ T cells was monitored using a combination of anti-CD8-FITC (BD Pharmingen; 555634), anti-CD69-PE (BD Pharmingen; 555531) and anti-CD25 (BD Pharmingen; 555434). Fluoresbrite calibration microspheres (Polysciences, Warrington, Pa.) were added to each sample to ensure acquisition of a consistent number of events. Data analyses was done using Flowjo v9.7.5 and EC50's were determined using the program PRISM-4 (GraphPad Software)

For the second example, human or cynomolgus PBMCs were isolated by Hypaque-Ficoll gradient centrifugation (Ficoll-Paque Plus, GE Healthcare), washed at low speed to remove platelets and resuspended in RPMI containing hIgG to block non-specific binding by TDBs to FcγRs. The assay was performed as described above, except that PBMCs at a concentration of 200,000/well were incubated with 11 ul of 10×3-fold serially diluted TDB. The E:T ratio was not determined and was donor dependent. Target cell killing ($CD14^+$ monocytes) and activation of effector T cells ($CD8^+$) were evaluated at ~40 hours by FACS. Depletion of hCLL-1 expressing $CD14^+$ monocytes was monitored using an anti-CD14-APC reagent (Human BD Pharmingen; 555399, Cyno Miltenyi: 130-091-243) and propidium iodide. Activation of CD8+ T cells was done as outlined in the section above.

Generation of TDBs—TDB antibodies were produced as full-length antibodies in the knob-into-hole format as human IgG1, as previously described (Atwell et al. J. Mol. Biol. 270: 26-35, 1997). Half antibodies were expressed in either E. coli or Chinese hamster ovary (CHO) cells, purified by Protein A-affinity chromatography, and the proper half antibody pairs were annealed in vitro as described previously (Spiess et al., Nat. Biotechnol. 2013). If TDB antibody production was carried out in CHO cells, the antibody may include an aglycosylation mutation, for example, at residue N297 (e.g., N297G), such that the TDB antibody was an effector-less variant and unable to initiate antibody-dependent cell-mediated cytotoxicity (ADCC).

After annealing, the anti-CLL-1/CD3 TDB antibodies were purified by Hydrophobic Interaction Chromatography (HIC) and characterized by analytical gel filtration, mass spectrometry, and polyacrylamide gel electrophoresis. The purified antibodies ran as a single peak (>99% of the signal) in gel filtration with less than 0.2% aggregates. No homodimers were detected by mass spectrometry.

B. Results

The efficacy of different anti-CLL1 antibody groups were tested in the TDB format. Bin 1 which includes parental h6E7 and h6E7 variants and parental h21C9, Bin 2 which includes 2061, and Bin 3 which includes 28H12. As shown in FIG. 4A, parental h6E7 (6E7.L4H1eN54) as well as variant 6E7.L4H1eA54 (Bin 1) in combination with 38E4v1 resulted in significant tumor cell (EOL-1) killing, which was both dose dependent and antigen-specific, compared to the non-targeting anti-gD arm in combination with 38E4v1. Furthermore, the product of deamination version of h6E7 (6E7.L4H1eD54), which has significantly reduced affinity for hCLL-1 (113.2 nM), showed negligible cell killing in combination with 38E4v1. Epitope bin 2-anti-CLL-1 antibody, 2061, while having a similar affinity for human CLL-1 as 6E7.L4H1eA54 had significantly reduced tumor cell (EOL-1) killing in combination with the same anti-CD3 arm (38E4v1). Epitope bin 3-anti-CLL-1 antibody, 28H12, in combination with 38E4v1 showed negligible tumor cell killing. See FIG. 4A. A summary of the results is provided in Table 7 below. Based on these results, human/cyno CLL-1 epitope bin 1 was further explored.

| Name | huCLL-1 [nM] | cyCLL-1 [nM] | Cell killing EC50 (ng/ml) |
|---|---|---|---|
| h6E7.L4H1N54 | 1.1 | 2.2 | 14 |
| h6E7.L4H1A54 | 3.1 | 3.1 | 34 |
| H6E7.L4H1D54 | 113.2 | 48.7 | >1000 |
| 20B1 | 4.5 | 6.1 | 531 |
| 28H12 | 18 | 0.3 | >1000 |

Figure 4B:
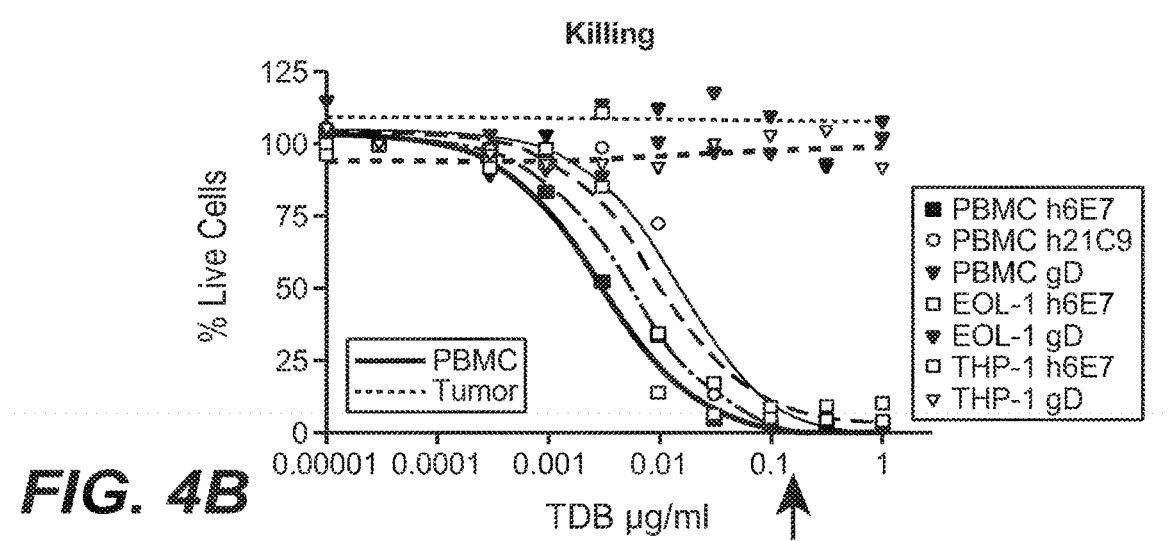
Figure 4C:
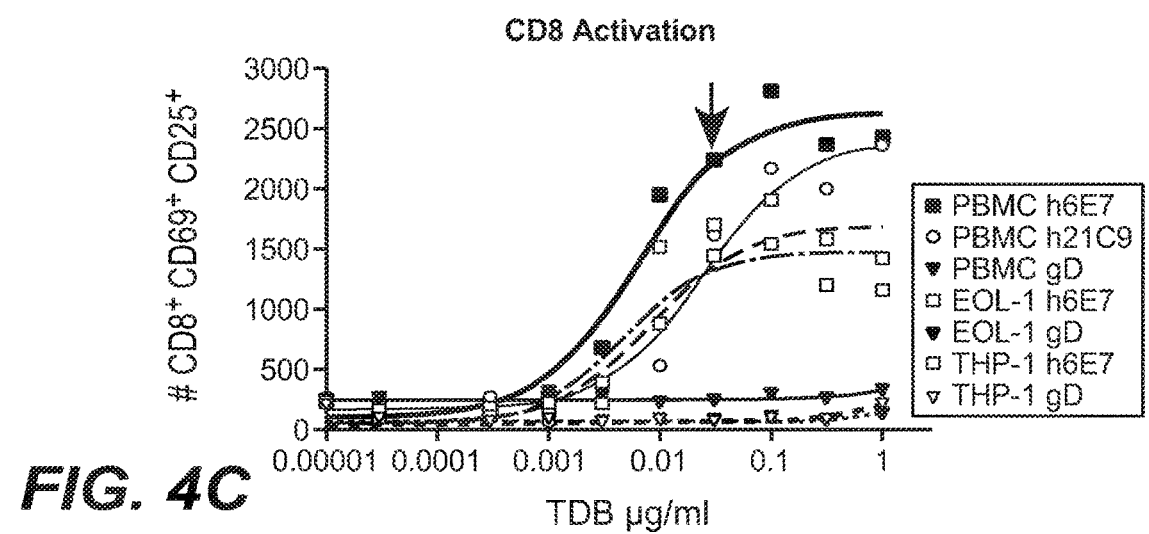

Both h6E7 and h21C9 are part of CLL-1 epitope bin 1. Experiments were performed as shown in FIG. 4B, to test the efficacy of h6E7 and h21C9 anti-CLL-1 TDBs killing either AML tumor cell lines (EOL-1/THP-1) or autologous $CD14^+$ cells expressing human CLL-1 from a single donor. Both CLL-1 TDBs, h6E7 (6E7.L4H1e)×38E4v1 and h21C9 (h21C9.L2H3)×38E4v1, showed significant killing of target cells in a dose-dependent manner compared to the negative control TDB, anti-gD×38E4v1, which showed no specific killing or $CD8^+$ T cell activation at a maximum TDB concentration of 1 μg/ml. Furthermore, the TDB concentration eliciting maximal killing coincided with maximal CD8+ T cell activation (FIG. 4C). The EC50s for killing target cells by h6E7 (6E7.L4H1e)×38E4v1 were 9.1 ng/ml (EOL-1), 5.4 ng/ml (THP-1), 2.8 ng/ml (human CD14+ monocytes), and by h21C9 (h21C9.L2H3)×38E4v1 was 14.8 ng/ml (human CD14+ monocytes).

Figure 5A:
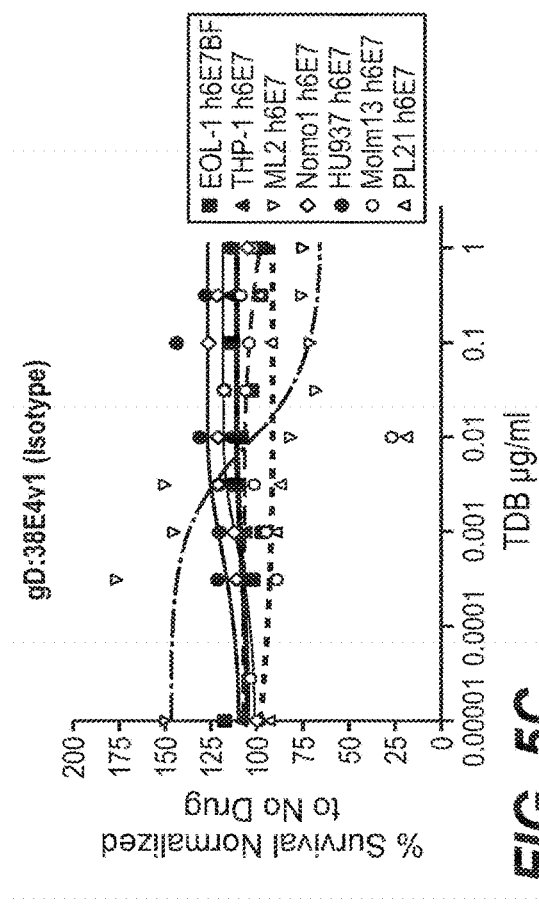
FIG. 5A-D shows potency of anti-CLL-1 TDBs on various AML tumor cell lines comparing percent survival normalized to drug at various TDB concentrations (μg/mL) using gDx38E4v1, h21C9 (h21C9.L2H3)x38E4v1, and h6E7 (6E7.L4H1e)x38E4v1.
Figure 5B:
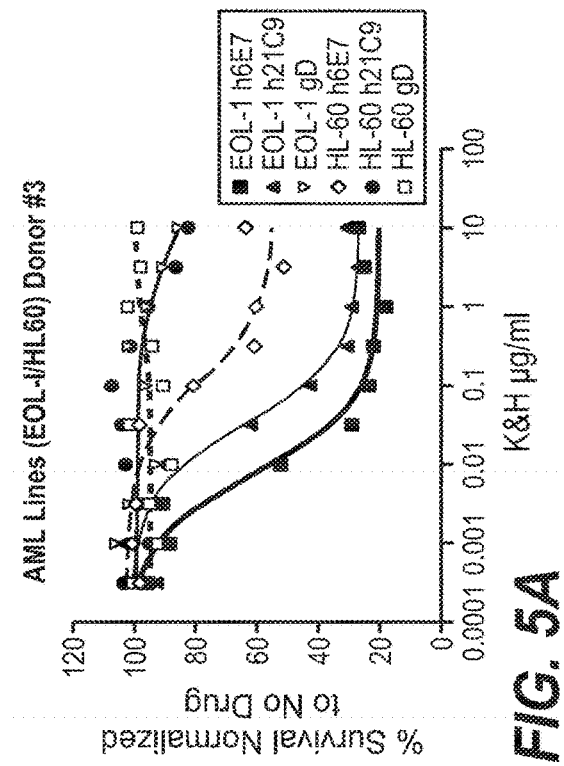
Figure 5C:
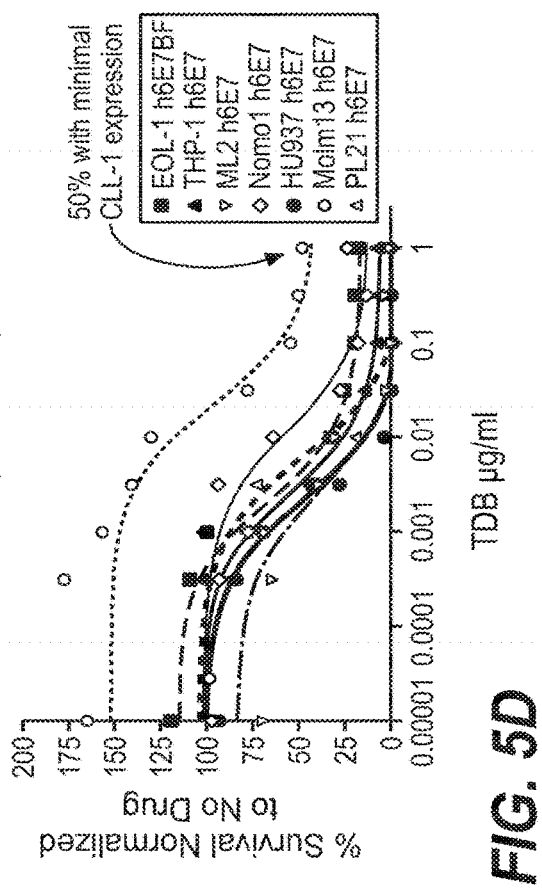
Figure 5D:
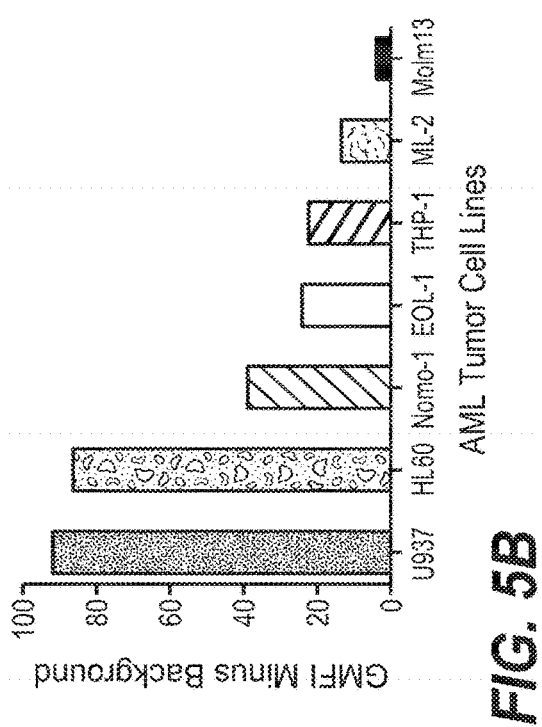

In experiments using other donors (FIG. 5A), h21C9 (h21C9.L2H3)×38E4v1 showed significant killing of EOL-1 (EC50s of 16.3 ng/ml) and very weak activity on HL-60, whereas h6E7 (6E7.L4H1e)×38E4v1 exhibited significant killing of EOL-1 (EC50 of 7.4 ng/ml) and HL-60 (EC50 of 95.6 ng/ml). CLL-1 expression and killing data from AML cell lines representing different subtypes of the disease is shown on a third donor (FIGS. 5B & C), which included a Bis-Fab TDB lacking the hIgG Fc region, h6E7 (6E7.L4H1e)×38E4v1, on EOL-1 cells (dotted line) has similar killing to h6E7 (6E7.L4H1e)×38E4v1 hIgG TDB. Overall, h6E7 (6E7.L4H1e)×38E4v1 showed good in vitro potency, and was also effective even on the low cell surface CLL-1 expressing cell line, Molm-13.

Figure 6A:
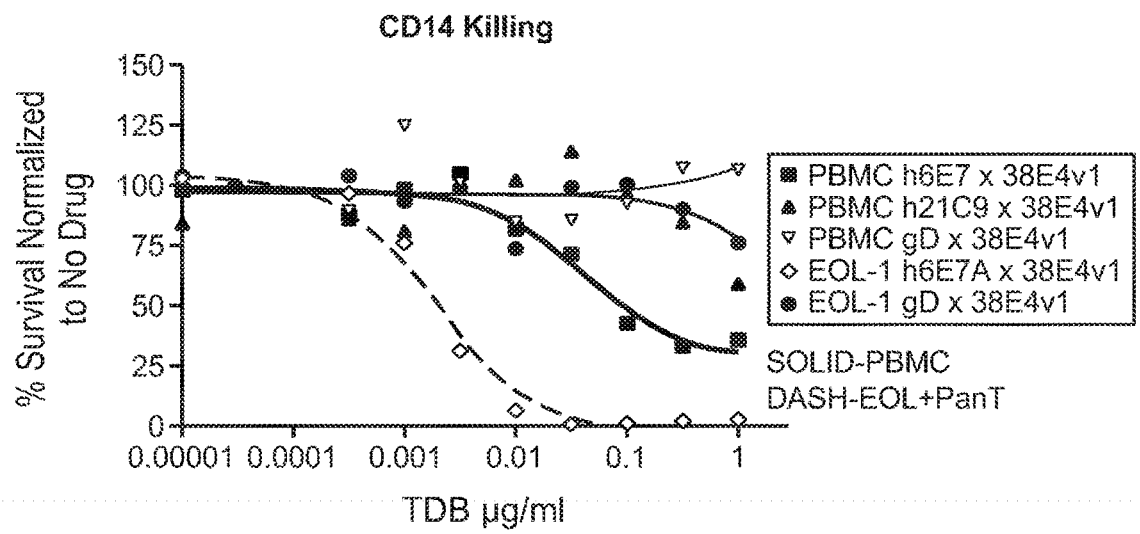
FIG. 6A-B shows in vitro characterization of h6E7 (6E7.L4H1e)x38E4v1 and h21C9 (h21C9.L2H3)x38E4v1 is killing of cynomolgus CD14+ cells in the presence of autologous cynomolgus PBMCs containing all subtypes of T cells and CD8 (CD8+, CD69+, CD25+) T cell activation at various TDB concentrations (μg/mL).
Figure 6B:
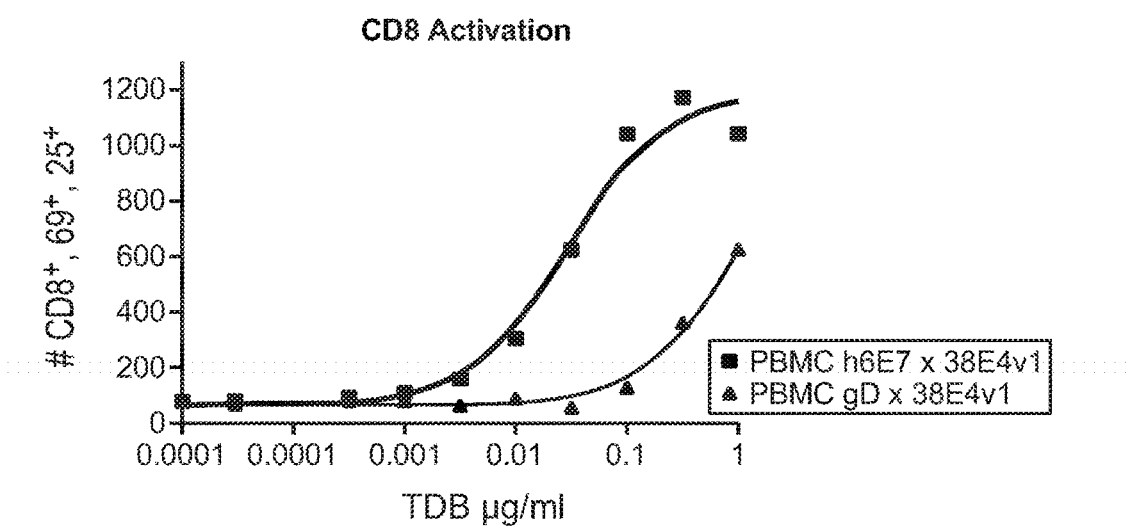

As shown in FIG. 6A, h6E7 (6E7.L4H1e)×38E4v1 and to a lesser extent h21C9 (h21C9.L2H3)×38E4v1 is capable of killing cynomolgus CD14+ cells in the presence of autologous cynomolgus PBMCs containing all subtypes of T cells. In addition, pan-T cells isolated from PBMCs in the presence of EOL-1 target cells and 6E7 (6E7.L4H1e)×38E4v1 showed significant killing of target cells with an EC50 of ~5 ng/ml, which is similar to that observed with human T cells. The TDB concentration eliciting maximal killing coincided with maximal CD8+ T cell activation (FIG. 6B).

A summary of the average EC50s determined from multiple donors is shown in Table 8. As shown in Table 7 using HL-60 cells, EOL-1 cells, and Human Autologous CD14+, the efficacy of h6E7 (6E7.L4H1e) was approximately 5 to 17 times greater than h21C9 (h21C9.L2H3) with the same anti-CD3 arm (38E4v1). Table 8.

|  | Disease Model | 6E7 (EC50 [ng/ml]) | 21C9 (EC50 [ng/ml]) |
| --- | --- | --- | --- |
| U937 | Histiocytic Lymphoma (Myeloid Lineage) | 2.1* | ND |
| HL-60 | Acute Promyelocytic Leukemia (M3) | 104 (n = 2) | 1761 |
| PL-21 | Acute Myeloid Leukemia (FLT3 ITD) | 5.9* | ND |
| NOMO-1 | Acute Myeloid Leukemia (M5A; MLL-AF9) | 12.2* | ND |
| EOL-1 | Eosinophilic Leukemia (M4 eos) | 4.1 (n = 5) | 51.1 |
| THP-1 | Acute Monocytic Leukemia (M5) | 3.6 (n = 3) | ND |
| ML-2 | Acute Myeloid Leukemia (M4; MLL-AF9) | 2.5* | ND |
| Molm-13 | Lowest expressor of CLL-1 | 23 (<25% dead) | ND |
| Human Autologous CD14+ | Normal Monocytes | 2.8 (n = 3) | 14.8 |

Figure 7A:
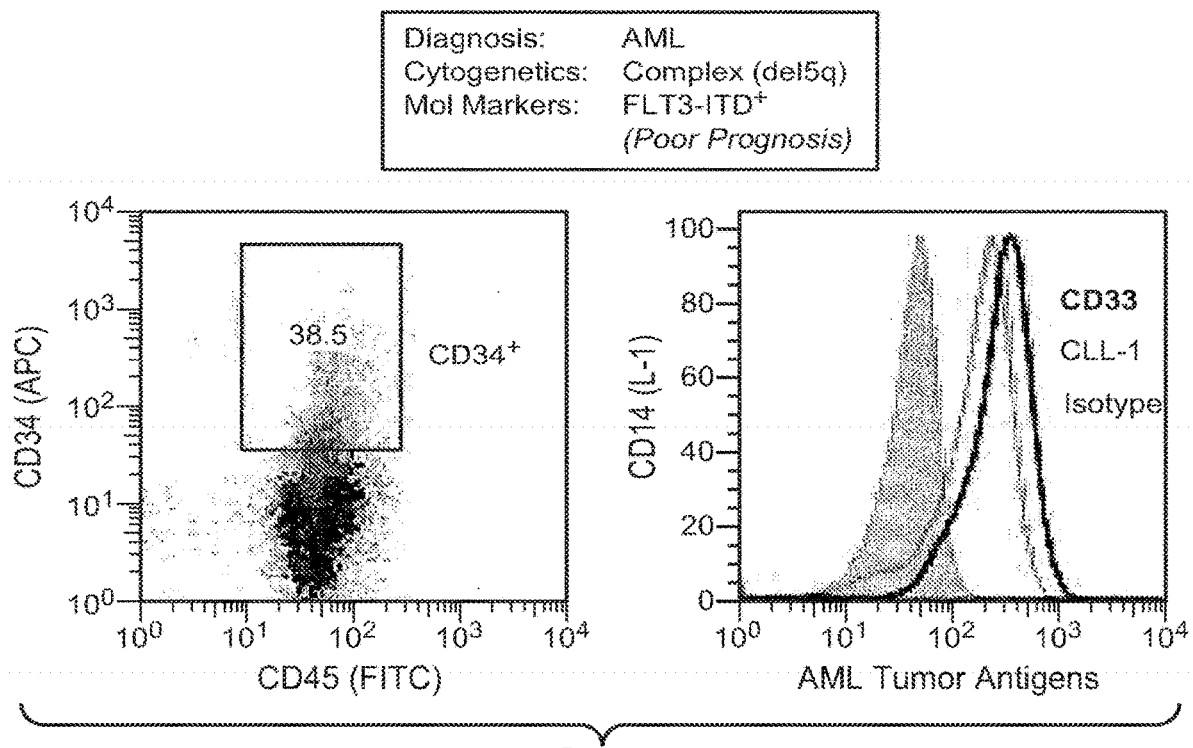
FIG. 7A-B shows in vitro potency of anti-CLL-1 TDB on AML patient bone marrow using h6E7 (6E7.L4H1e)x38E4v1 and gDx38E4v1.

In another example, potency of h6E7 (6E7.L4H1e)×38E4v1 TDB was tested on a patient sample with a confirmed diagnosis of AML and significant expression of both CD33 and CLL-1 on CD34+ cells by flow cytometry (FIG. 7A). The in vitro killing assay was performed as described above using isolated naïve allogeneic human CD8+ T-cells and frozen density-gradient purified bone marrow cells from an AML patient (Stanford Blood Bank, Stanford, Calif.). The experiment was done in the following medium containing the following supplements to support hematopoietic stem cells/progenitors: Iscove's Modified Dulbecco's Medium (IMDM), 10% heat inactivated FCS, 2 mM Glutamine, 1x StemSpan CC100 cytokine cocktail (StemCell Technologies), 20 ng/ml human GM-CSF, 20 ng/ml human G-CSF and 0.3 mg/ml low endotoxin human IgG (Molecular Innovations, Novi, Mich.). The E:T ratio was 3:1 using 150,000 and 50,000 cells, respectively and performed as described above for ~40 h.

Figure 7B:
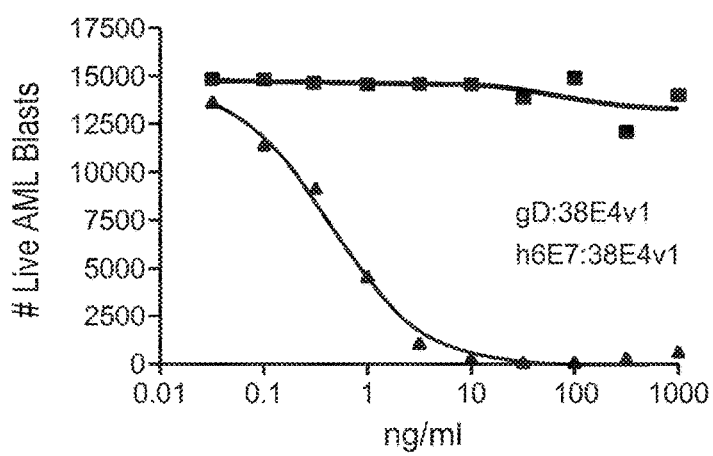

FIG. 7B shows that h6E7×38E4v1 was able to kill AML blasts in a dose-dependent manner compared to the Ig-matched non-targeting TDB, anti-gD×38E4v1. The number of live AML blasts remained unchanged during the 40 h incubation with the anti-gD×38E4v1 TDB suggesting that killing by h6E7 (6E7.L4H1e)×38E4v1 was TDB-specific not due to the growth conditions.

C. In Vivo Efficacy of Anti-CLL-1 TDB

The T cell dependent bispecific (TDB) antibody used in the following examples comprises the human CLL-1 and human CD3e antigen binding determinants. The anti-human CLL-1 arm comprises either the sequence of 6E7 (6E7.L4H1e) or optimized variants h6E7 (N54-A or -S or -E or -Q or -D) humanized Fab and an anti-human CD3e arm sequence comprising either h40G.5c, 38E4v1, or 38E4v11 (corresponding to either low, high, or very high affinity for hCD3ε) humanized Fab.

Figure 8A:
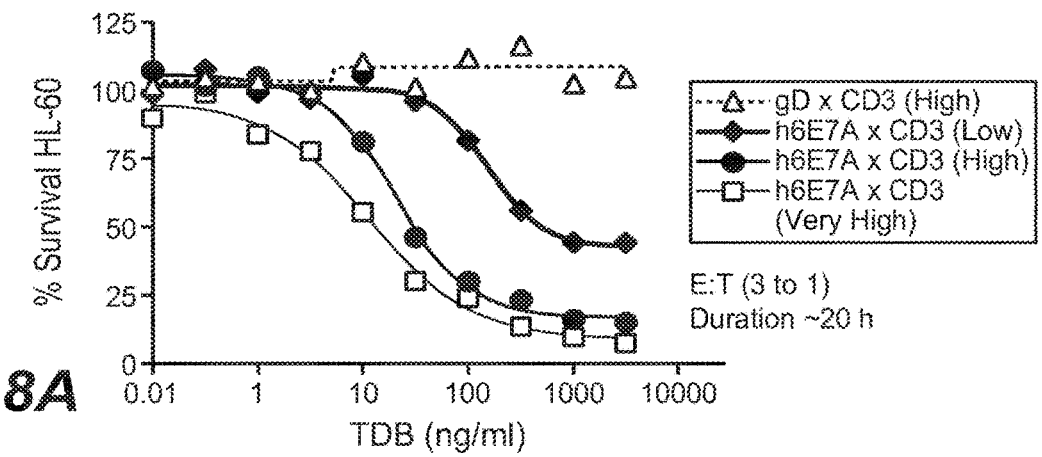
Figure 8B:
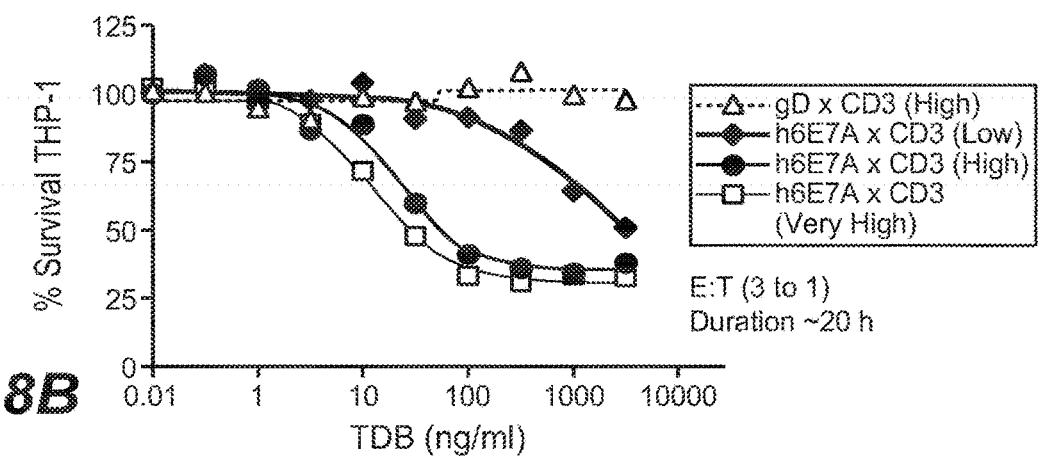
Figure 8C:
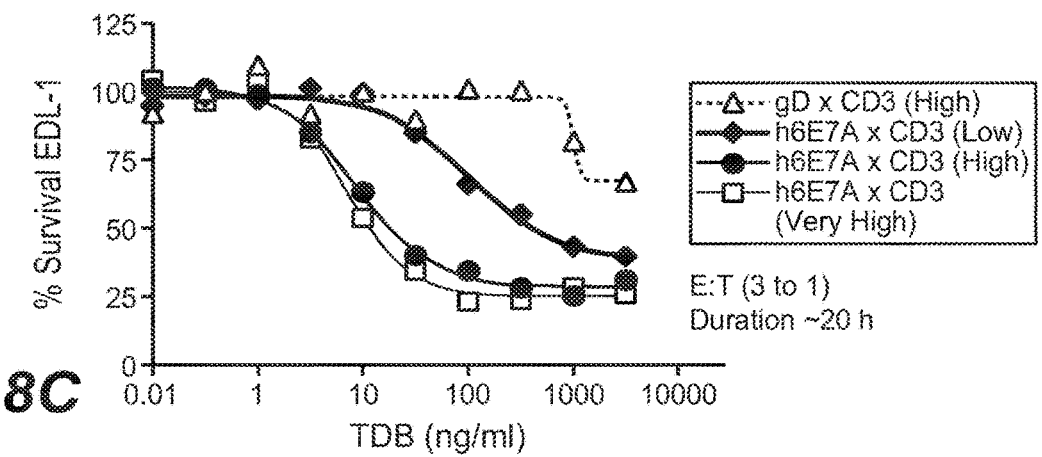
Figure 8E:
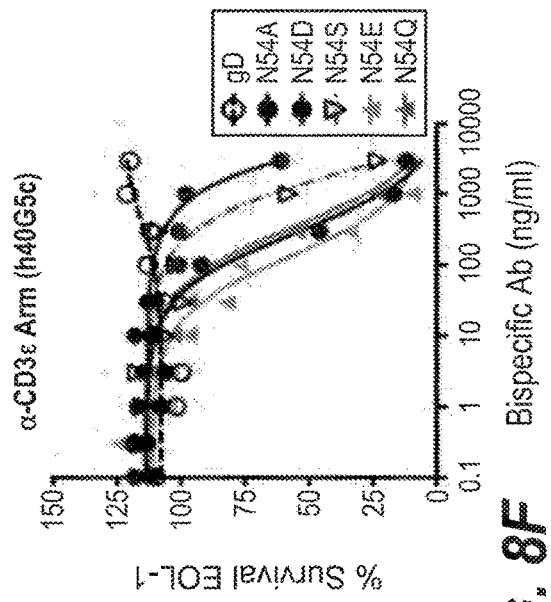
Figure 8F:
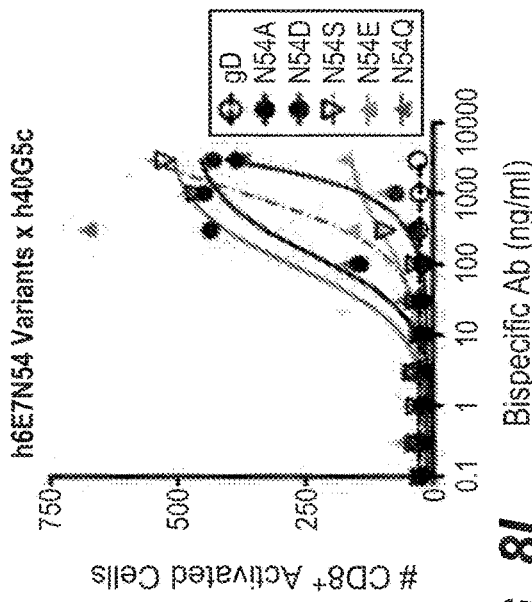
Figure 8H:
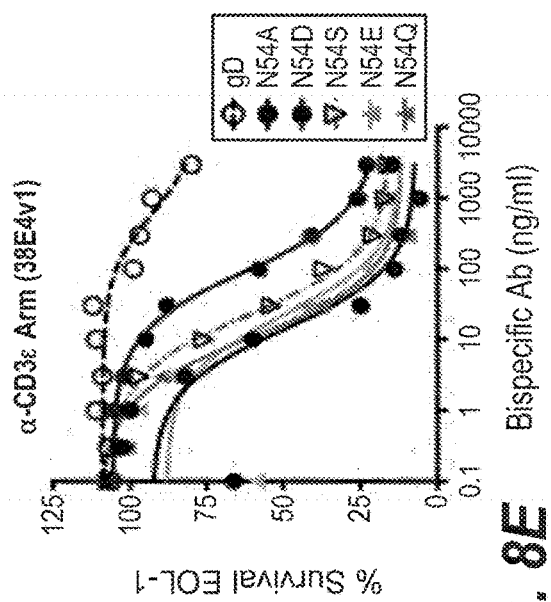
FIG. 8H-I shows CD8 T cell activation in response to h6E7N54 variants paired with the high affinity anti-CD3 arm (38E4v1) or the low affinity anti-CD3 arm (h40G5c).
Figure 8I:
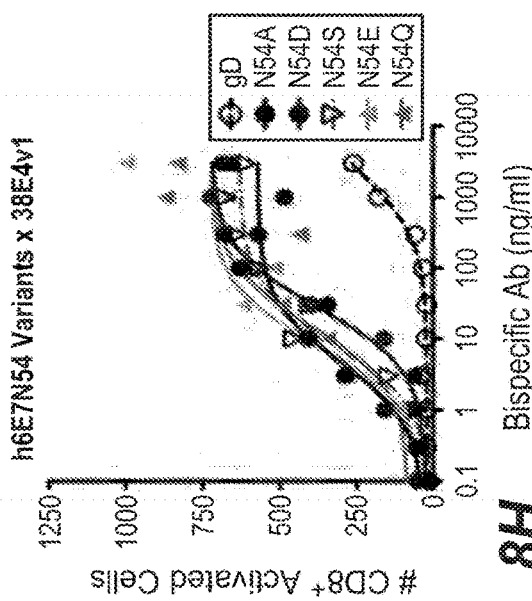

In vitro characterization of h6E7N54A (also called 6E7.L4H1eA54) was done as described for the in vitro killing assay above. FIG. 8A-D shows that 6E7.L4H1eA54 TDBs carrying either the low affinity (h40G5c) or high (38E4v1) or very high (38E4v11) affinity hCD3e arm are capable of killing AML tumor cell lines with similar potency in a dose-dependent manner. In addition, in vitro assessment of optimized variants of h6E7.L4H1e N54-A or -S or -E or -Q or -D humanized Fab paired with anti-human CD3ε Fab, comprising either 38E4v1 or h40G5c, was done to determine the potency of the hCLL-1 arm. FIG. 8E-G shows that higher affinity of the h6E7 arm to human CLL-1 correlated with improved in vitro potency compared to the N54D variant-aspartic acid (D) is the product of asparagine (N) deamidation, and this modification of N54 leads to lower affinity binding to CLL-1. The rank order of potency for the h6E7 variants was similar, regardless of whether the human CD3ε arm was 38E4v1 or h40G5c. However, as shown in FIG. 8H-I, utilization of the high affinity anti-human CD3ε arm (38E4v1) resulted in elevated levels of T cell activation at lower bispecific antibody concentrations compared to that of the low affinity human CD3 arm, h40G5c. Overall, the EC50s were similar for h6E7 variants (N54-A or -S or -E or -Q) in the presence of 38E4v1, and h6E7 variants (N54-A or -E or -Q) in the presence of h40G5c.

Genetically engineered mice co-expressing human CLL-1 and human CD3ε were characterized and used for testing the efficacy of an anti-human CLL-1 TDB in vivo. Human CLL-1 (CLEC12a) BAC transgenic C57BL/6N mice (Charles River, Wilmington, Mass.) and human CD3ε BAC transgenic C57BL/6N mice were generated at Genentech and maintained in accordance with the American Association of Laboratory Animal Care guidelines. Additionally, double BAC transgenic mice co-expressing both human CLL-1 and human CD3ε was accomplished by breeding of the parental hCLL-1 and hCD3ε BAC transgenic animals. Studies to demonstrate the potency of an anti-human CLL-1×anti-CD3ε TDB in vivo were conducted in compliance with the National Institutes of Health Guide for the Care and Use of Laboratory Animals and were approved by the Institutional Animal Care and Use Committee at Genentech.

Figure 9A:
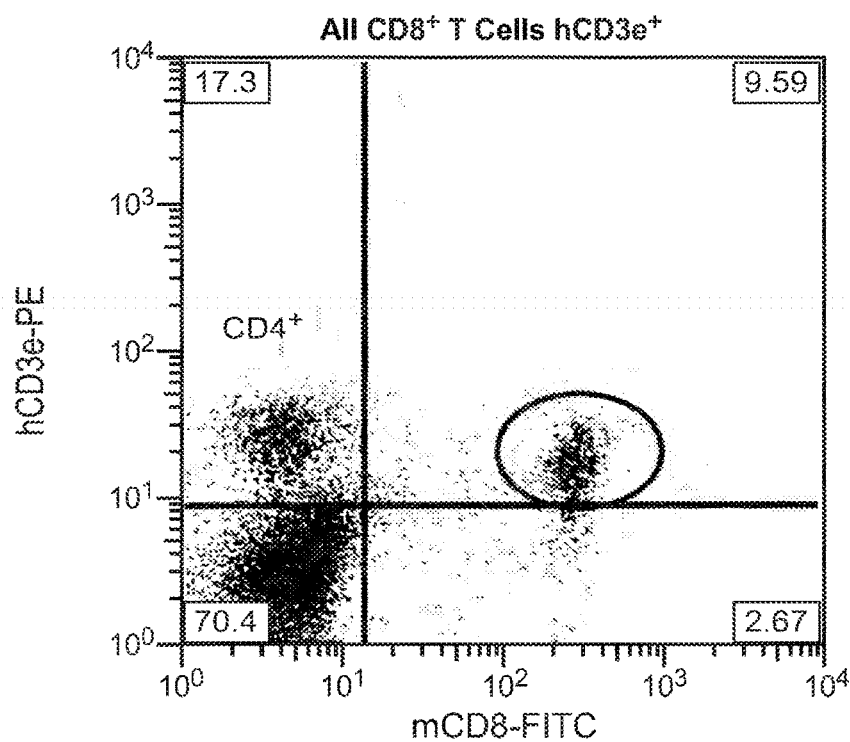
FIG. 9A-B shows expression of hCLL-1 and hCD3e transgenes in double BAC-Tg (hCL-1/hCD3ε) mice.
Figure 9B:
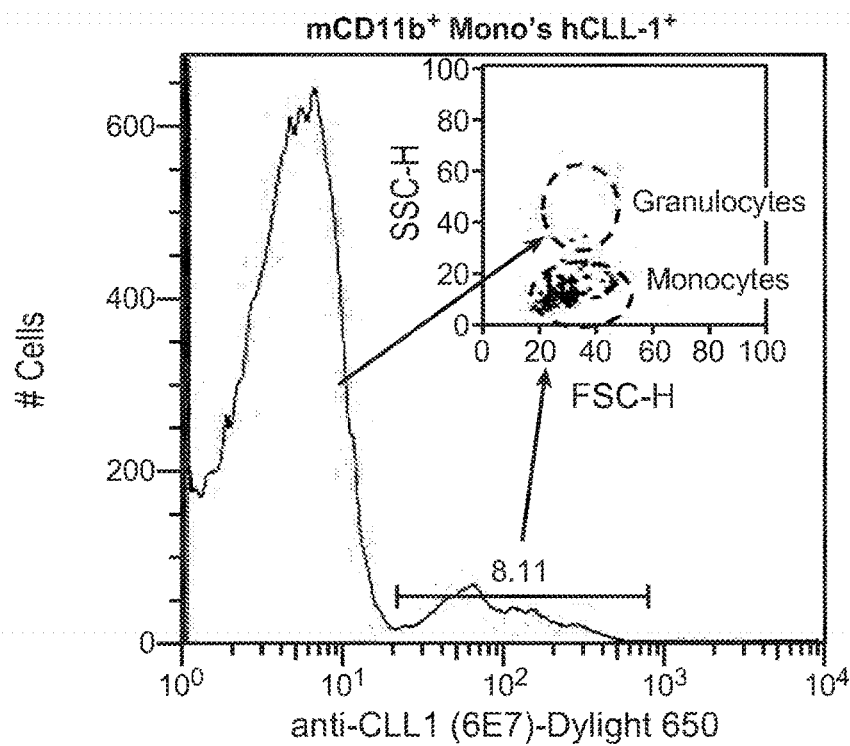
Figure 10A:
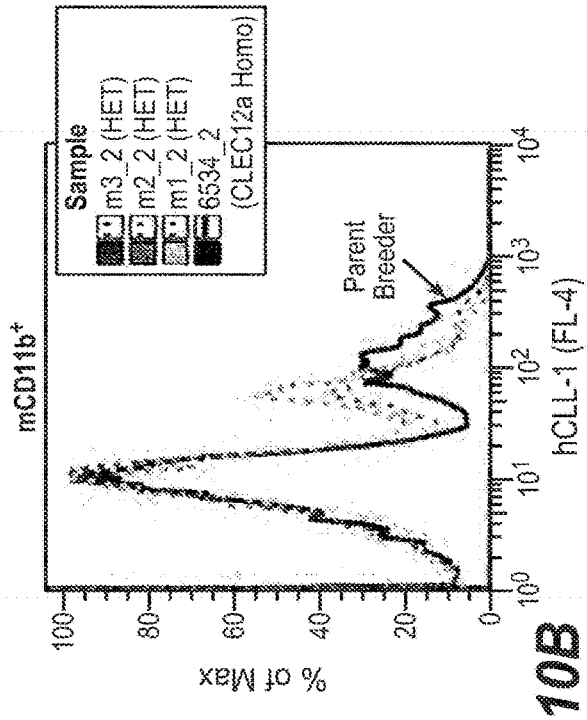
FIG. 10A-D shows expression of hCLL-1 and hCD3e transgenes in heterozygous double BAC-Tg (hCL-1/hCD3ε) mice compared to homozygous parents.
Figure 10B:
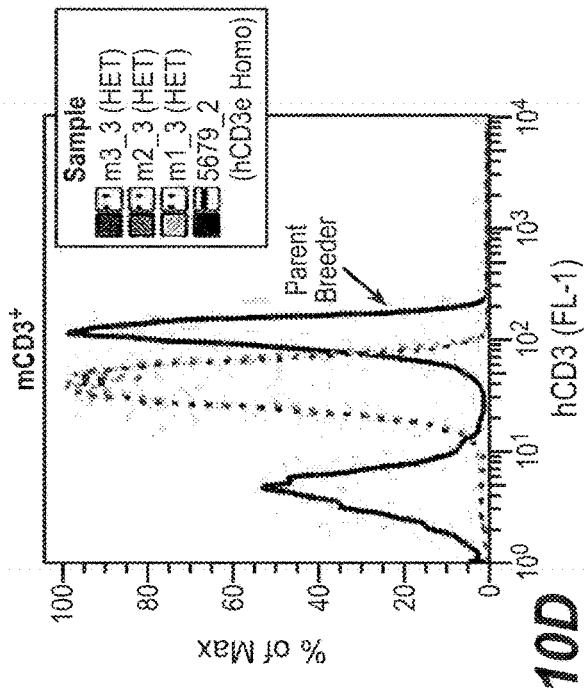
Figure 10C:
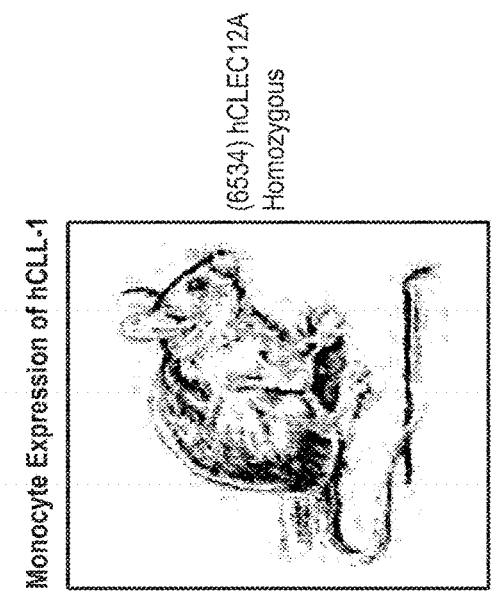
Figure 10D:
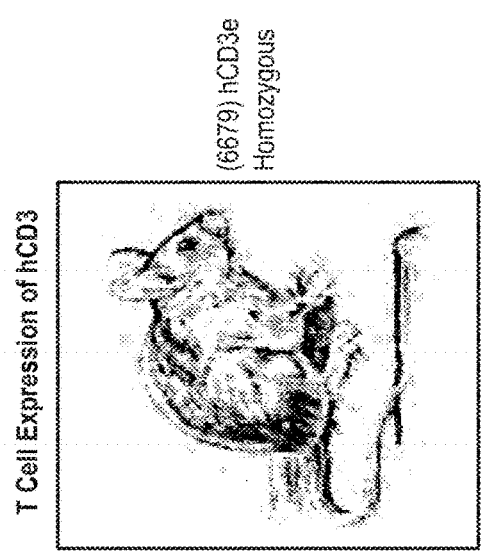

Double BAC-Tg (2×BAC-Tg) mice were characterized by flow cytometry and shown to express both transgenes—human CLL-1 and human CD3ε. Blood from transgenic mice was treated with ACK lyses buffer to remove red blood cells and pre-incubated with a blocking solution (5% mouse, 5% rat and 0.2 mg/ml human IgG, 0.5% BSA, 2 mM EDTA in PBS) for 20 minutes on ice to reduce non-specific binding to FcγRs. Confirmation of human CD3ε surface expression on 2×BAC-Tg CD8$^+$ effector T cells was determined by staining with a rat anti-mouse CD8-FITC (Miltenyi) and a mouse anti-human CD3-PE (BD Biosciences), and confirmation of human CLL-1 expression on 2×BAC-Tg CD11b$^+$ monocytes was demonstrated by staining with a rat anti-mouse CD11b-FITC (BD Biosciences) and variant h6E7A (6E7L4H1eA54-Dylight 650 (Genentech). FIG. 9 shows that blood from double BAC-Tg (hCLL-1/hCD3ε) mice express human CD3 on mouse CD8$^+$ T cells, and human CLL-1 on mouse CD11b$^+$ monocytes but not mouse granulocytes. In addition, FIG. 10 shows that the level of expression of either transgene is similar to that of their corresponding parent.

Figure 11:
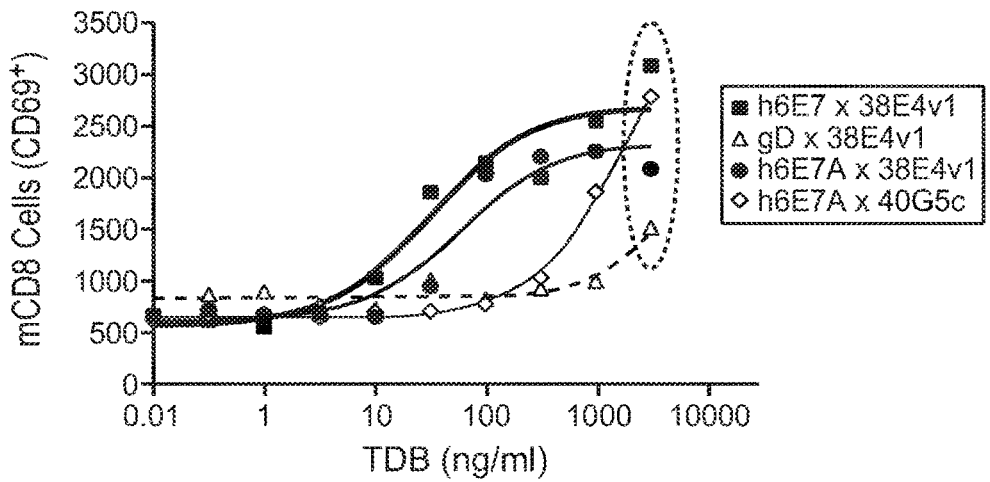
FIG. 11 shows ex vivo activation of CD8+ T cells in double BAC-Tg (hCL-1/hCD3e) treated with anti-CLL-1 TDBs, gDx38E4v1, 6E7 (6E7.L4H1e)x38E4v1, N54A (6E7.L4H1eA54)x38E4v1, and N54A (6E7.L4H1eA54)x40G5 (40G5c).

To demonstrate that the chimeric CD8$^+$ T cells (expressing both mouse and human CD3) were capable of being activated by a TDB comprising an anti-human CD3ε arm, blood was stimulated ex vivo with various concentrations of TDBs for 20-40 hours as described in Section A. In this experiment, PBMCs from 2×BAC-Tg mice were isolated by density gradient centrifugation using Histopaque-1083 (Aldrich-Sigma, St Louis, Mo.) followed by a low speed spin to remove platelets. The final concentration range of TDB was 0.3-3000 ng/ml that also included a no TDB control for each test article. The TDBs used were: anti-gD×38E4v1 (isotype matched negative control) or parental h6E7 (6E7.L4H1eN54)×38E4v1 or variant h6E7N54A (6E7.L4H1eA54)×38E4v1 or variant h6E7N54A (6E7.L4H1eA54)×h40G5c. After either ˜20 or ˜40 hours the cells were stained with anti-mouse CD8-FITC and anti-mouse CD69 (eBioscience, San Diego, Calif.) to quantitate T cell effector activation by flow cytometry. FIG. 11 shows that all CLL-1 specific TBDs were capable of achieving maximal activation at 3000 ng/ml.

In vivo efficacy studies to test the potency of TDB antibodies containing various arm combinations of anti-human CLL-1 and anti-human CD3 were done using the 2×BAC-Tg mice. Mice were randomized into groups of 5 and given a single intravenous dose on Day 0 of either 0.1 mg/kg or 0.5 mg/kg. The mice were randomized into groups as follows: Group 1 (Vehicle; Histidine buffer), Group 2 (anti-gD×38E4v1 @ 0.5 mg/kg), Group 3 (anti-gD×h40G5 @ 0.5 mg/kg), Group 4 (h6E7N54A (6E7.L4H1eA54)× 38E4v1 @ 0.1 mg/kg), Group 5 (h6E7N54A (6E7.L4H1eA54)×38E4v1 @ 0.5 mg/kg), Group 6 (h6E7N54A (6E7.L4H1eA54)×h40G5 @ 0.1 mg/kg), Group 7 (h6E7N54A (6E7.L4H1eA54)×h40G5 @ 0.5 mg/kg), and Group 8 (h6E7N54A (6E7.L4H1eA54)×38E4v11 @ 0.5 mg/kg); the anti-gD TDB represents a non-CLL-1 targeting isotype-matched antibody control. Prior to randomization and dosing, all animals were phenotyped by flow cytometry to confirm that the expected expression profile of both transgenes and that the CD8$^+$ cells were not activated as judged by the expression of surface CD69. Activation of CD8$^+$ cells and counts of CD11b$^+$ monocytes were done by flow cytometry on Day −6, 1, 7, and 14. At the time of analyses, blood from an individual naïve 2×BAC-Tg mouse was used for setting the BD FACS Caliber and for establishing a baseline. At termination (day 15), blood from mice was collected for PK analyses.

Figure 12:
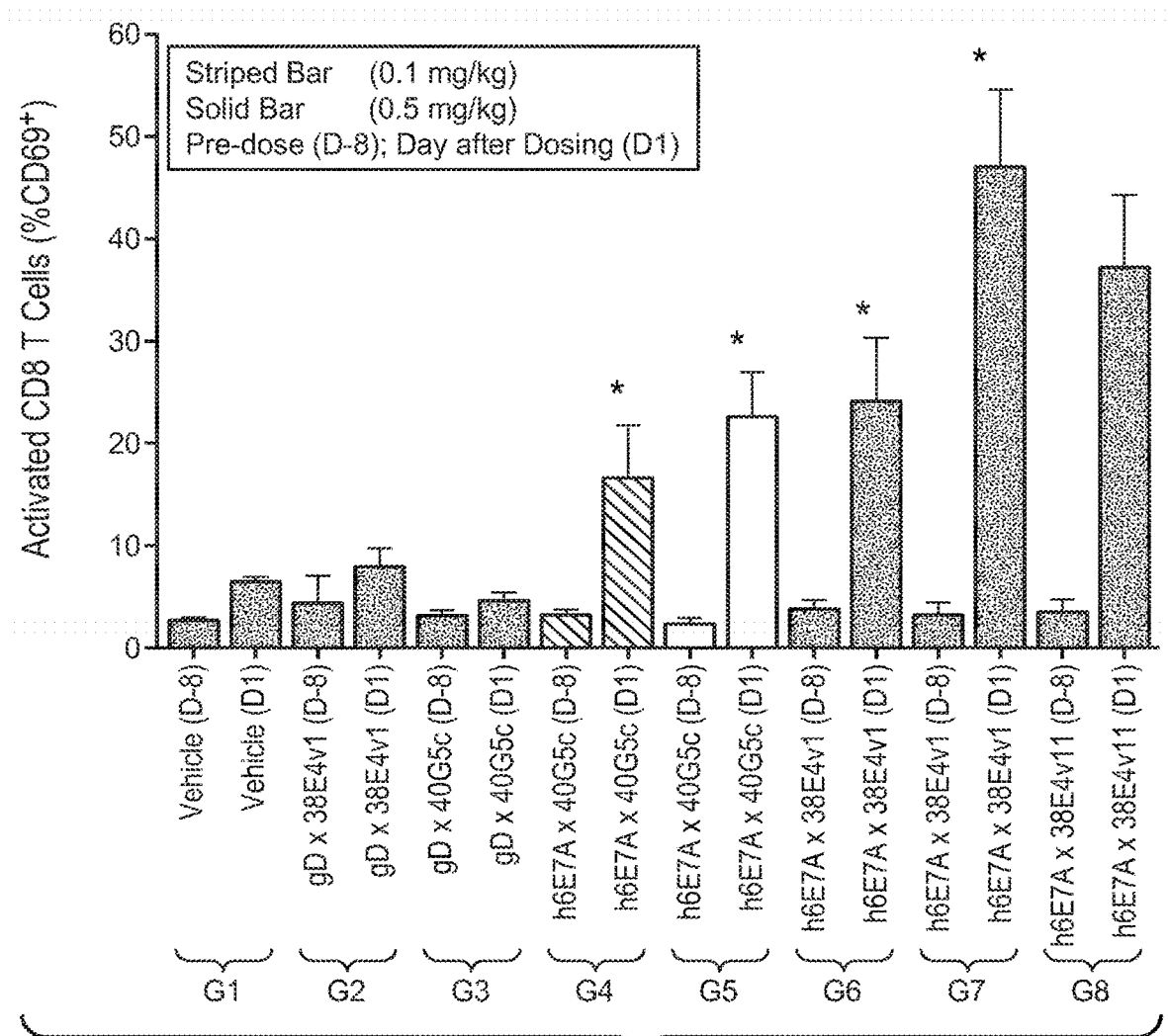
FIG. 12 shows in vivo activation of CD8+ T cells double BAC-Tg (hCL-1/hCD3e) treated with anti-CLL-1 TDBs, gDx38E4v1, gDx40G5c, h6E7A (6E7.L4H1eA54)x40G5c, h6E7A (6E7.L4H1eA54)x38E4v1, and h6E7A (6E7.L4H1eA54)x38E4v11.
Figure 13A:
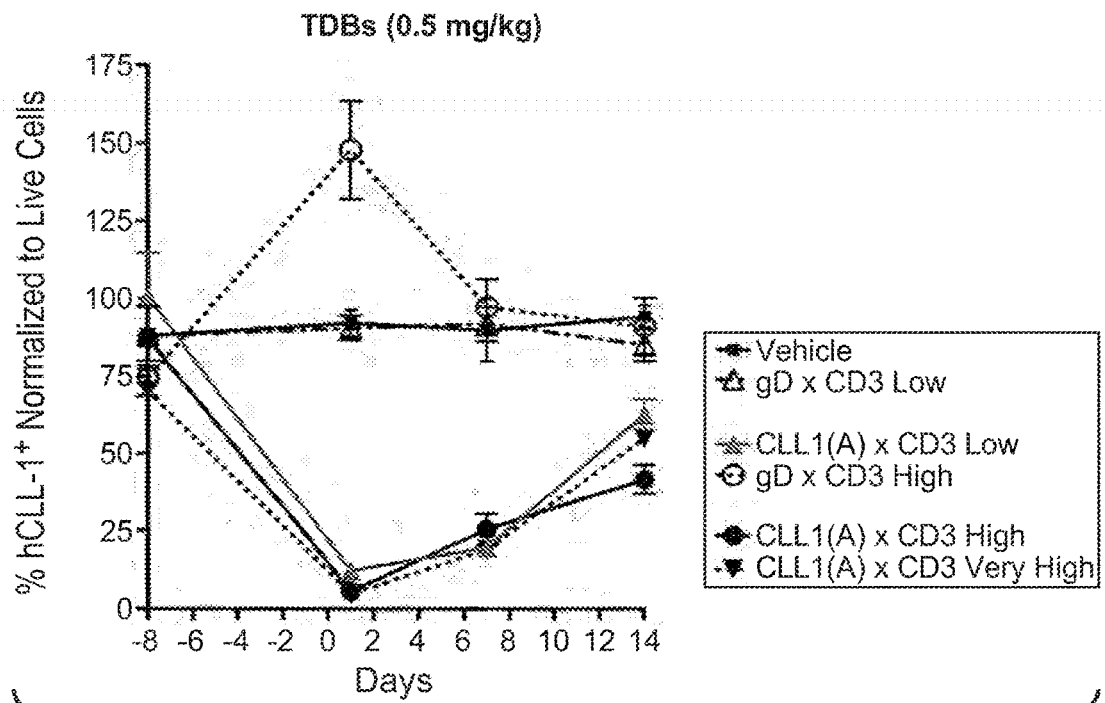
FIG. 13A-B shows in vivo depletion of hCLL-1+ cells in hCLL-1/hCD3e BAC-Tg mice treated with anti-CLL-1 TDBs with anti-CLL-1 TDBs, gDxCD3 High (38E4v1), gDxCD3 Low (40G5c), CLL1(A) (6E7.L4H1eA54)xCD3 Low (40G5c), CLL1(A) (6E7.L4H1eA54)xCD3 High (38E4v1), and CLL1(A) (6E7.L4H1eA54)xCD3 Very High (38E4v11).
Figure 13B:
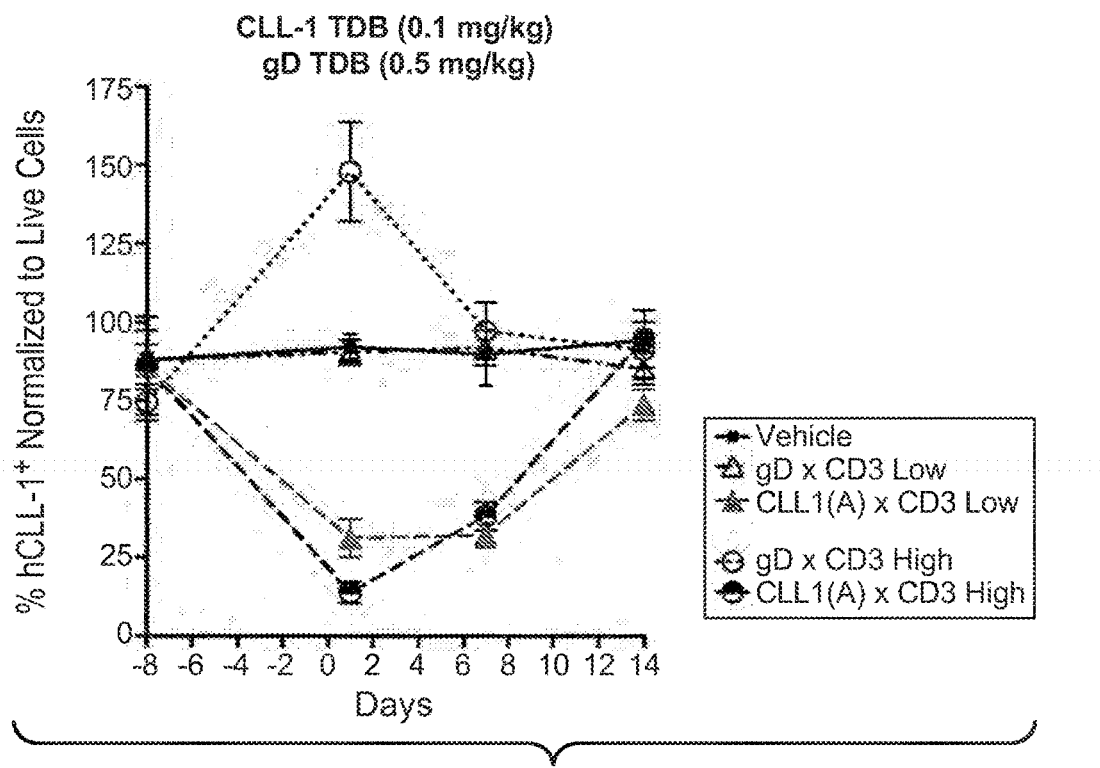

FIG. 12 shows that after the day of dosing (Day 1), only animals in Groups 4-8 had significantly elevated levels of CD69 expression. Potency was measured by monitoring depletion of mCD11b$^+$/hCLL-1$^+$ cells using an anti-mouse CD11b-FITC and an anti-human CLL-1-Alexa 647 antibody (50C1; BD Biosciences, San Jose, Calif.) that was shown not to cross-block our therapeutic antibodies h6E7 or h21C9. Potency correlated with antigen-specific activation of CD8$^+$ effector cells, as maximum depletion of hCLL-1$^+$ cells was achieved the day after dosing by mice treated with (G5) h6E7N54A (6E7.L4H1eA54)×38E4v1 TDB at 0.5 mg/kg and (G8) h6E7N54A (6E7.L4H1eA54)×38E4v11 TDB at 0.5 mg/kg, and significant depletion in mice treated with (G4) h6E7N54A (6E7.L4H1eA54)×38E4v1 @ 0.1 mg/kg or (G7) h6E7N54A (6E7.L4H1eA54)×h40G5c @ 0.5 mg/kg or (G6) h6E7 (6E7.L4H1eN54)×h40G5c at 0.1 mg/kg (FIG. 13). Over the course of the experiment, anti-CLL-1 specific TDBs at 0.5 mg/kg were most effective, regardless of whether the TDB included either a low, high, or very high affinity hCD3ε binding arm. At Day 14, at least ˜25-50% depletion was maintained by mice in Groups 5 and 7. No activation of CD8$^+$ T cells or depletion of hCLL-1$^+$ cells was observed in the vehicle or non-CLL-1 targeting isotype matched TDB control groups. In a similar experiment, the potency of parental and variants of h6E7 was very similar (data not shown).

D. In Vitro Safety Assessment of Anti-CLL-1 TDB

Figure 14B:
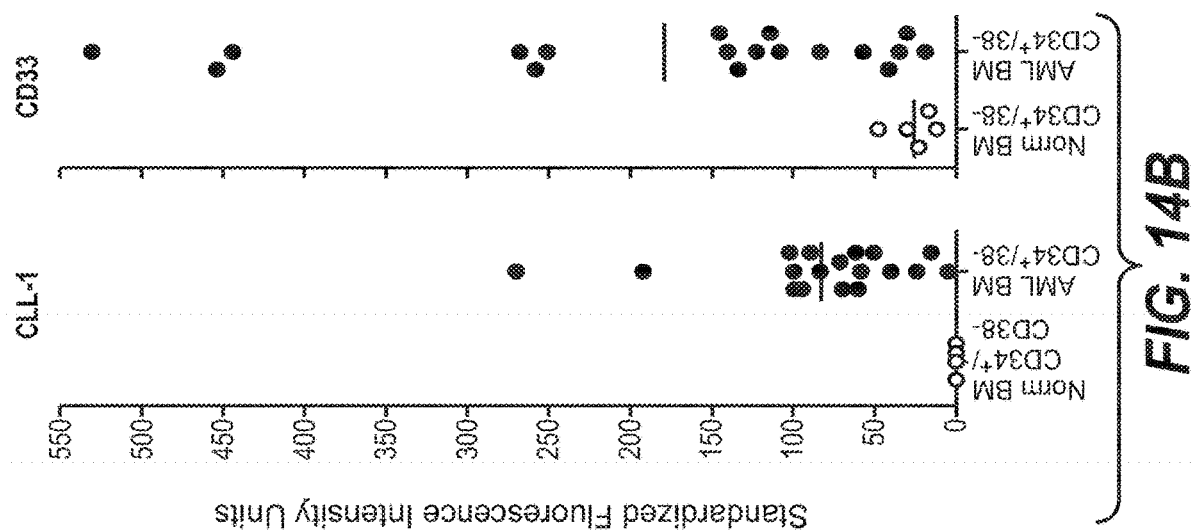
FIG. 14A-B shows expression profile of CLL-1 (A) and (B) and CD33 (B) on normal and AML human leukocytes.
Figure 14A:
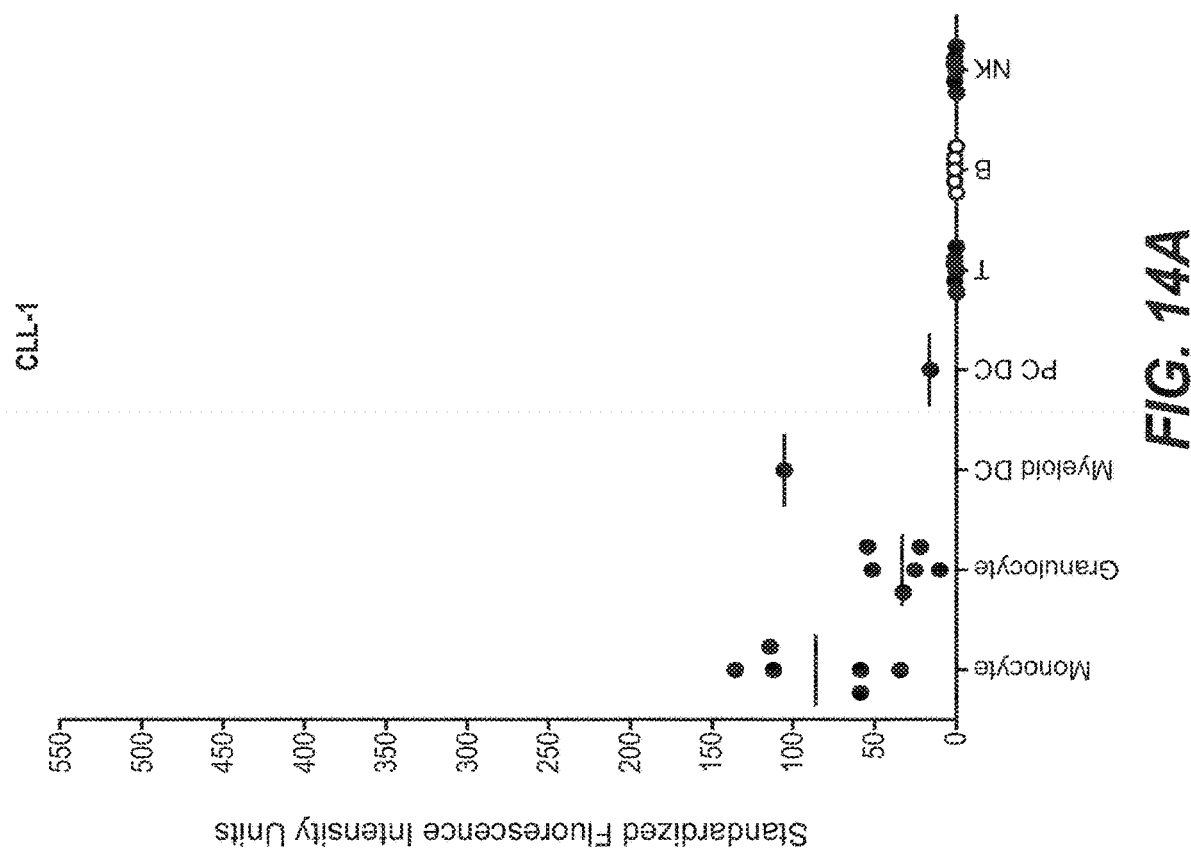

Human hematopoietic stem cells (HSC; CD34$^+$, CD38$^-$) express CD33 but appear not to express CLL-1. Therefore, to determine whether a TDB specific for CLL-1 could be an effective and safer therapeutic than a TDB targeting CD33, human bone marrow cells were treated with anti-gD× 38E4v1 TDB or h6E7 (6E7.L4H1e)×38E4v1 TDB followed by enumeration of resultant GEMM (granulocyte, erythrocyte, monocyte, megakaryocyte) colony-forming units derived from HSCs and progenitor cells. By definition, HSCs possess the property of self-renewal and formation of progentiors and differentiated lineage-specific cells whereas progenitors have the capacity to form colonies of differentiated lineage-specific cells but are incapable of self-renewal. Our phenotyping of HSCs (CD34$^+$ and CD38$^-$) and progenitor/differentiated (CD34$^+$ CD38$^+$) cells show only CLL-1 expression by the later compared to CD33 which is detected on CD34$^+$/CD38$^-$ and progenitor/differentiated cells (FIG. 14).

In the following example, a human Colony-Forming Cell (CFU) assay, MethoCult, (StemCell Technologies, Vancouver, BC, Canada) was used to determine the effect of an anti-human CLL-1 TDB treatment on the ability of human bone marrow-derived HSCs to proliferate and differentiate in culture. In this assay, one may predict that immature hematopoietic cells (HSCs) void of CLL-1 expression should be spared depletion by treatment with a CLL-1 TDB whereas the lineage committed progenitors and differentiated cells expressing CLL-1 on the cell surface should be abolished by the treatment.

Fresh human bone marrow and blood from the same donor was acquired from ALLCELLS (Alameda, Calif.), and processed by density-gradient separation. Human CD8+ T cells were isolated from the blood PBMCs and together with bone marrow leukocytes used in the in vitro killing assay as described in Section A. The effector (CD8+ T cells) to target (BM leukocytes) ratio was 3 (150,000 cells): 1 (50,000 cells). Target cells were resuspended in Iscove's Modified Dulbecco's Medium (IMDM) containing the following supplements to support HSCs: 10% heat inactivated FCS, 2 mM Glutamine, StemSpan CC100 cytokine cocktail (StemCell Technologies), 20 ng/ml human GM-CSF, 20 ng/ml human G-CSF and 0.3 mg/ml low endotoxin human IgG (Molecular Innovations, Novi, Mich.) and pre-incubated for 1 h at 37° C. to block Fcγ Rs before the addition of CD8+ T cells and TDBs. The final concentration of TDB in the 100 ul assay volume was either 5 or 50 ng/ml. The test article was h6E7 (6E7.L4H1e)×38E4v1 TDB and the IgG-matched non-targeting negative control was an anti-human gD×38E4v1 TDB. The cells were incubated for 40 h. Depletion of CD14+ monocyte by FACS was checked on two replicates, and the remaining 3 replicates were harvested, washed and resuspended in 3 ml of MethoCult. An aliquot of 1.1 ml was dispensed from a 3 ml syringe with a 16 g blunt end needle into a 35 mm dish (StemCell Technologies); two platings per treatment group. The dishes were incubated for 14 days, and monitored from day 7 through day 14.

Figure 15A:
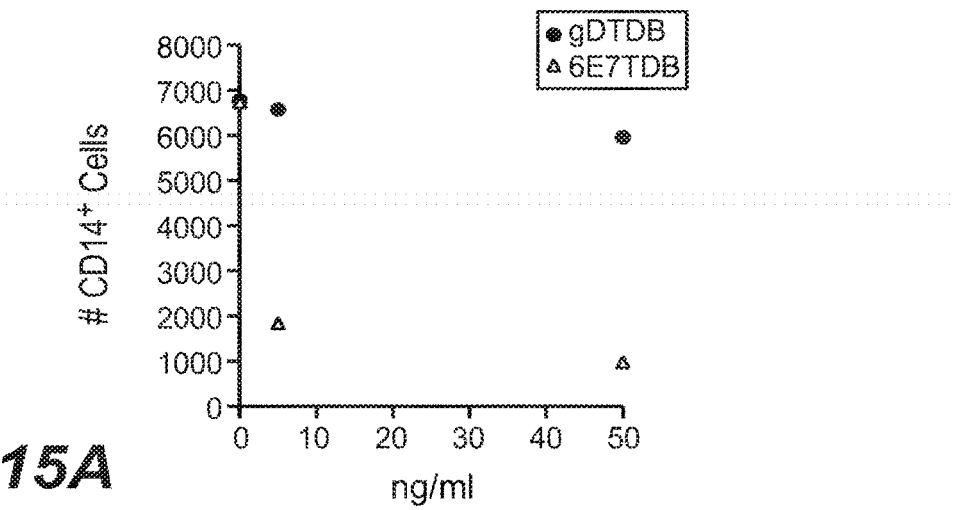
FIG. 15A-C shows impact on hematopoiesis following treatment of human bone marrow cells with anti-CLL-1 h6E7A (6E7.L4H1eA5)x38E4v1 TDB.
Figure 15B:
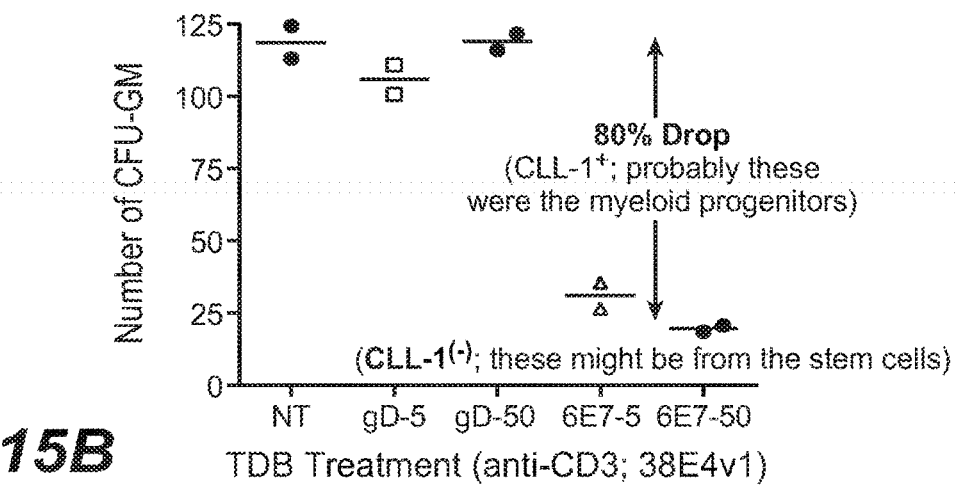
Figure 15C:
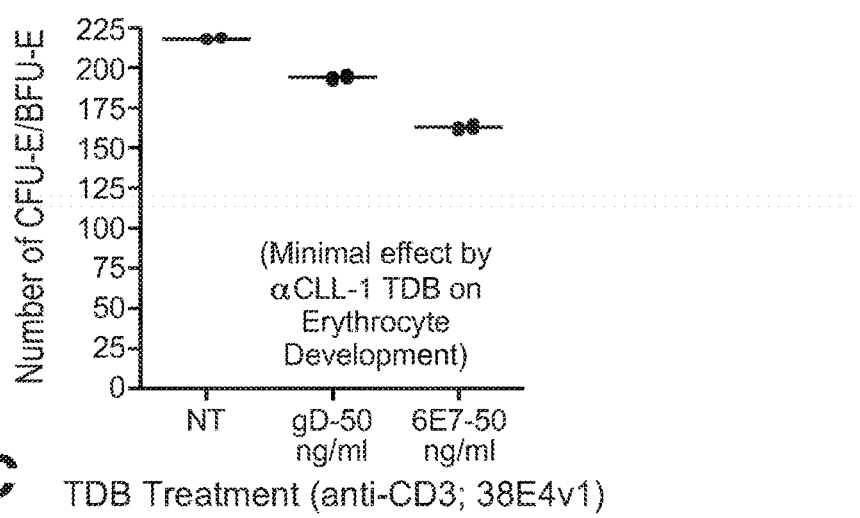

The killing assay showed specific depletion of CD14+ bone marrow monocytes by the h6E7 (6E7.L4H1e)×38E4v1 TDB at both the 5 and 50 ng/ml concentrations compared to the anti-human gD×38E4v1 negative control TDB (FIG. 15A). This confirmed that the anti-CLL-1 TDB was functional. The enumeration of CFU-GM, -M, and -GEMM was done on day 10 and the results are shown in FIG. 15B. An ~80% drop in CFU-GM, -M and GEMM was observed for cells treated with h6E7 (6E7.L4H1e)×38E4v1 at 5 ng/ml and 50 ng/ml compared to cells treated with anti-human gD×38E4v1 or no treatment. It is assumed that this loss of CFU represents the depletion of hematopoietic myeloid progenitor and mature lineage differentiated cells that express human CLL-1. The remaining CFUs are mostly likely the result of the self-renewal and differentiation capacity of human CLL-1$^{(-)}$ HSCs. This result provides evidence that a TDB targeting cells expressing human CLL-1 does not drastically affect the capacity of hematopoiesis. A similar experiment using 200-fold more h6E7 (6E7.L4H1e)×38E4v1 TDB gave similar results. In addition, the regeneration of erythrocytes was accessed at day 14. Treatment with h6E7 (6E7.L4H1e)×38E4v1 TDB showed a slight diminution in CFU-E and BFU-E of ~25% compared to untreated cells and ~16% to the anti-human gD×38E4v1 TDB (FIG. 15C). The results suggest that erythroid regeneration by HSCs was mostly intact. Lastly, sorting of human bone marrow CD34+ cells expressing either CD33 or CLL-1 and plating in the MethoCult assay showed only reconstitution of CFU-GM, CFU-G, or CFU-M for the CD34+/CLL-1+ population whereas the CD34+/CD33+ population produced additional cell lineages (CFU-E and CFU-GEMM) that is indicative of a more primitive hematopoietic cell (data not shown).

E. In Vivo Pharmacokinetics and Pharmacodynamics of Anti-CLL-1 TDB

Combinations of anti-human CLL-1 h6E7N54A (6E7.L4H1eA54) and anti-human CD3ε (h40G5c or 38E4v1 or 38E4v11) bispecific antibodies were studied in vivo to determine their PK and PD in peripheral blood, bone marrow and spleen. Non-specific and target-specific PK were characterized in SCID beige and 2XBAC-Tg mice, respectively. Mice were randomized into groups of 3 and given a single intravenous dose on Day 0 of 0.5 mg/kg. Mice were assigned to the following groups: Group 1 (h6E7N54A (6E7.L4H1eA54)×h40G5c), Group 2 (h6E7N54A (6E7.L4H1eA54)×38E4v1) and Group 3 (h6E7N54A (6E7.L4H1eA54)×38E4v11). The study using the hCLL-1×hCD3ε BAC-Tg mice (2×BAC-Tg) was conducted as described above, and blood and tissues were collected at the following time points: Day −7 (pre-dose), and post dose at 15 min, 2 h, 6 h, Day 1, 7, and 14. All time points, except for the pre-dose, were terminal. Bispecific antibody concentrations and cytokine concentrations were measured in blood. T cell activation and reduction of target cell numbers were measured in blood and tissues. Flow analyses were performed on an 8-color BD LSR Fortessa cell analyzer.

Figures 17A, 17B:
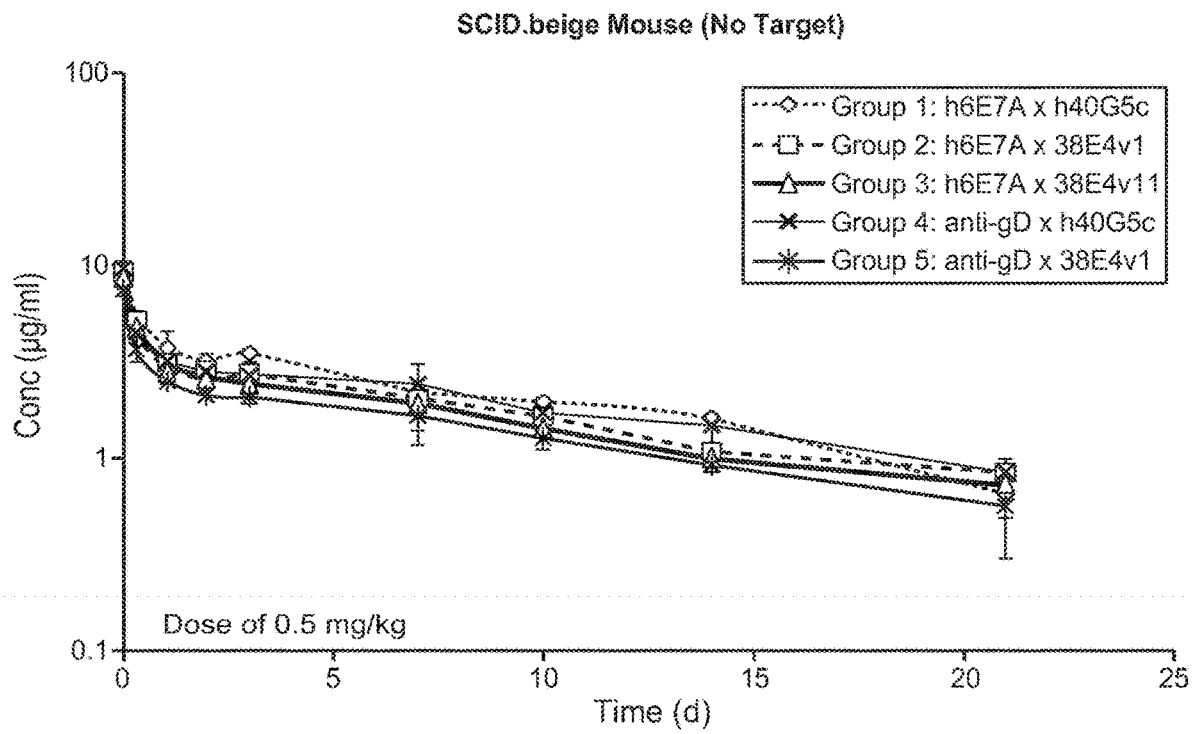
FIG. 17A-D shows pharmacokinetic (PK) data in SCID.beige mice (A and B) and hCLL-1/hCD3e BAC-Tg mice (C and D) treated with anti-CLL-1 TDBs.
Figures 17C, 17D:
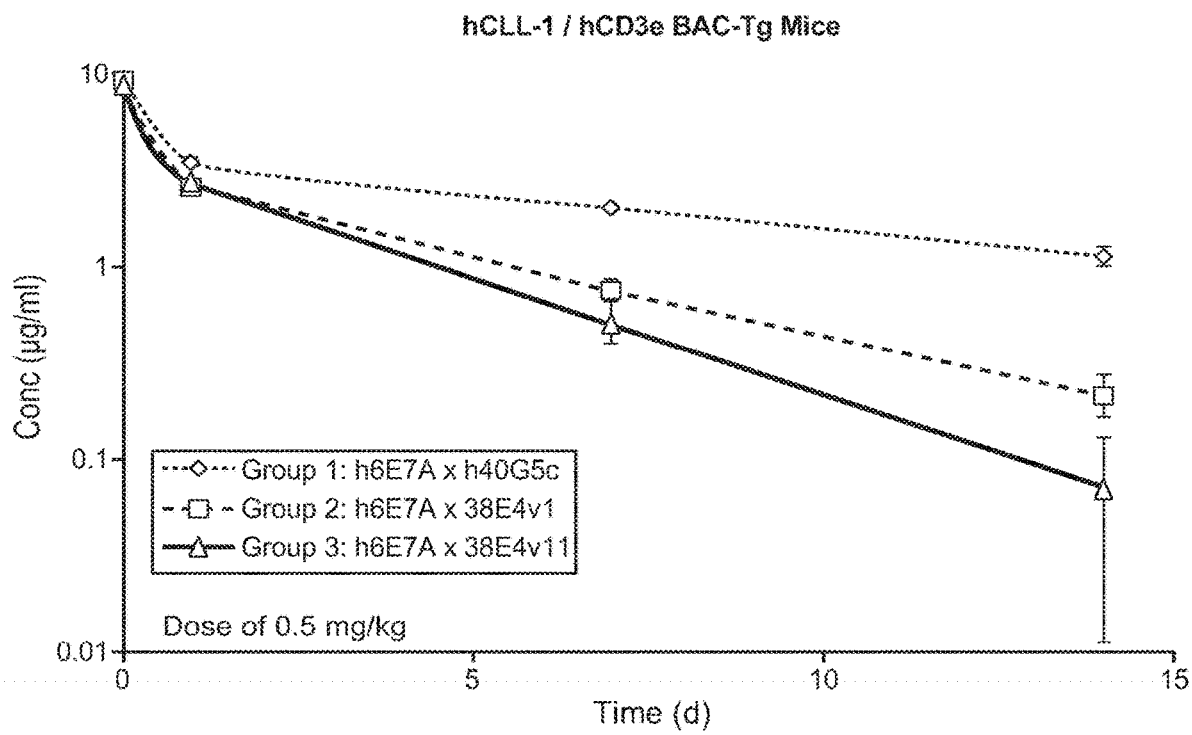

FIG. 17A shows that in SCID mice (void of T cells (CD3) and myeloid cells expressing human CLL-1) the bispecific antibodies (Groups 1-3) have similar antibody concentrations over time compared to non-CLL-1 targeting isotype-matched antibody controls (anti-gD×h40G5c and anti-gD×38E4v1). The PK parameters are summarized in the FIG. 17B, and illustrate that in the absence of target the anti-hCLL-1×anti-CD3ε bispecific antibodies demonstrate similar PK and clearance comparable to anti-gD controls. When these bispecific antibodies were examined in mice expressing both targets (human CD3ε and human CLL-1), Cmax values were comparable between the hCLL-1×anti-CD3ε molecules. However, CD3 arm affinity dependent differences in exposure were observed (FIG. 17C). The h6E7N54A×h40G5c had the slowest clearance (CL=10.6 mL/d/Kg) which translated into higher drug exposure over time (AUC=47.1 d.μg/mL) compared to bispecific antibodies comprising 38E4v1 (CL=23.5 mL/d/Kg, AUC=21.3 d.μg/mL) or 38E4v11 (CL=37.4 mL/d/Kg, AUC=18.1 d.μg/mL) (FIG. 17D).

Figure 18A:
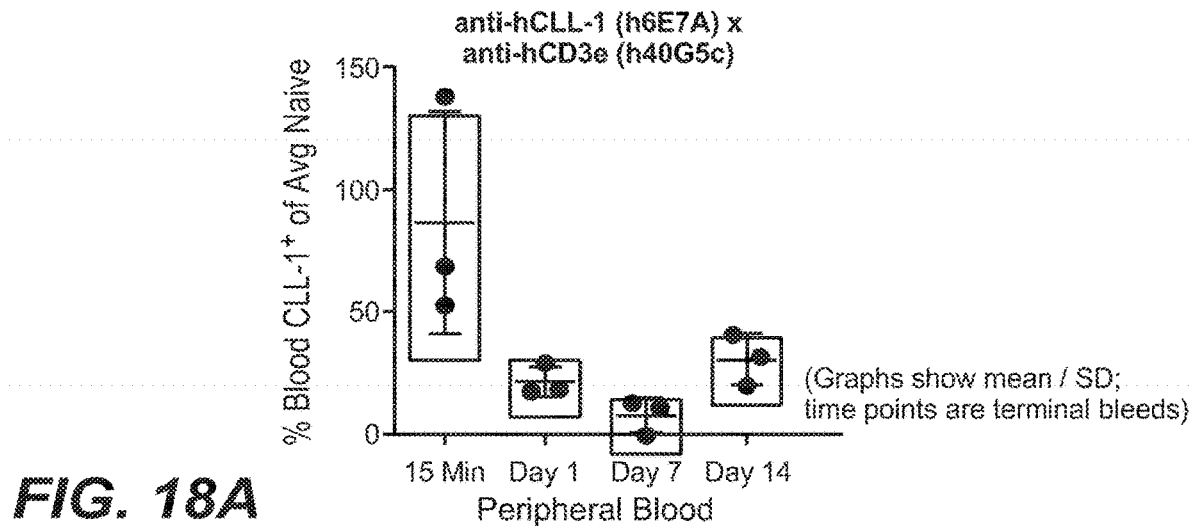
FIG. 18A-C shows pharmacodynamics (PD) data in peripheral blood (A), bone marrow (B), and spleen (C) of hCLL-1/hCD3e BAC-Tg mice treated with h6E7A (6E7.L4H1eA54)xh40G5c TDB.
Figure 18B:
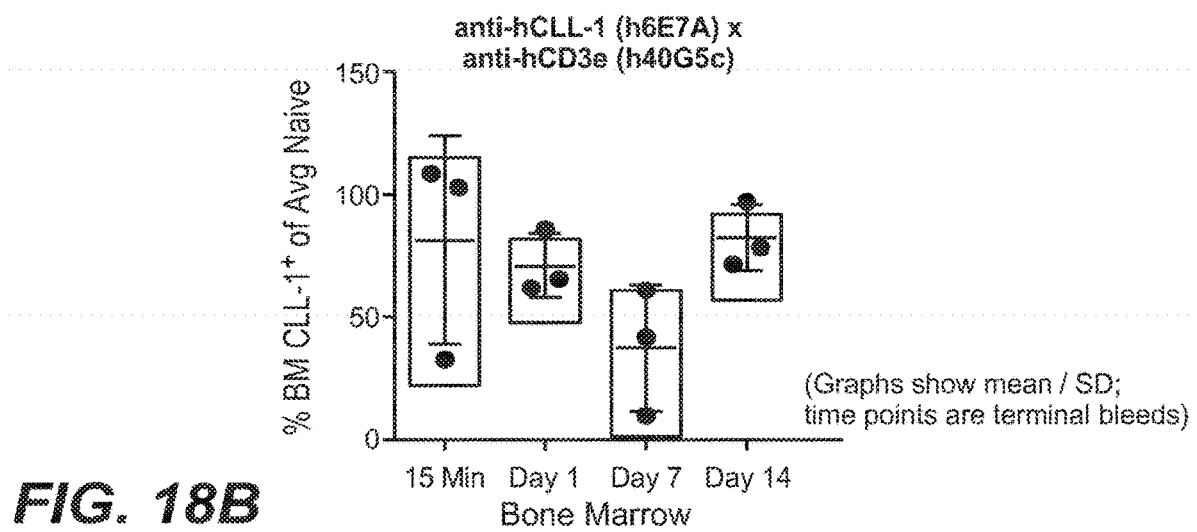
Figure 18C:
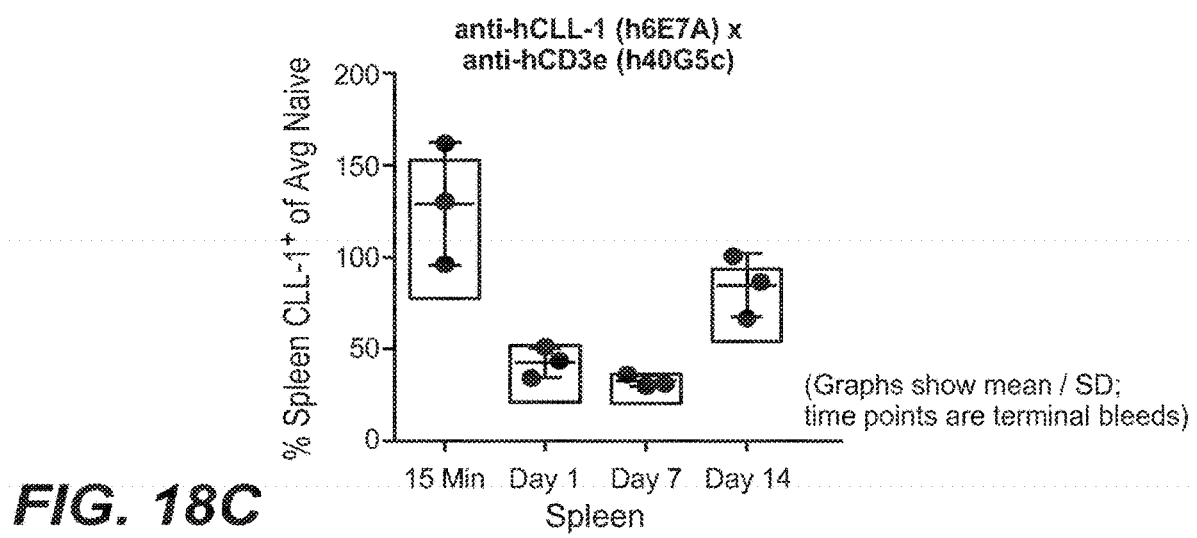
Figure 19A:
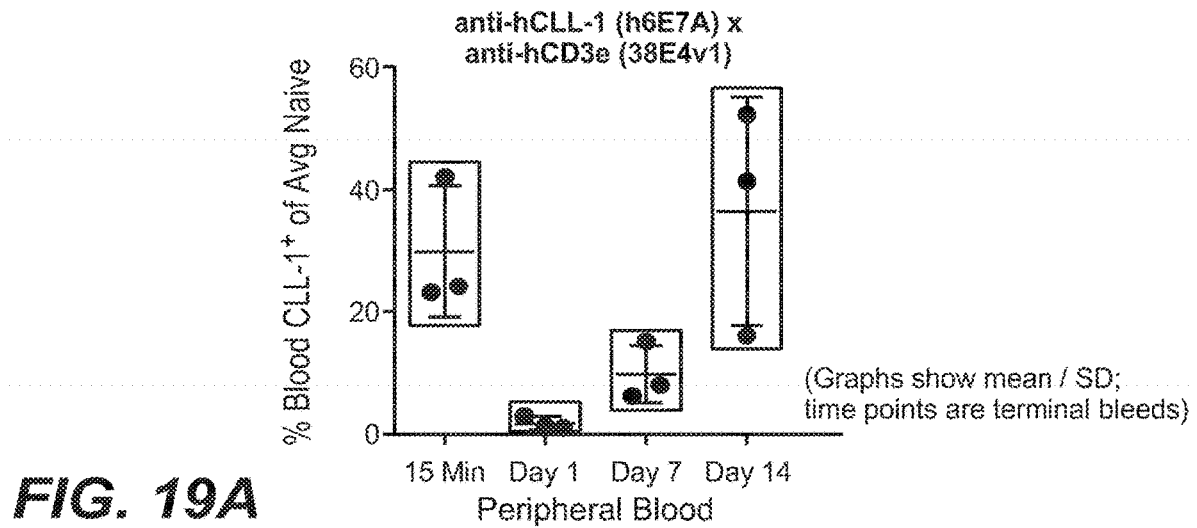
FIG. 19A-C shows PD data in peripheral blood (A), bone marrow (B), and spleen (C) of hCLL-1/hCD3e BAC-Tg mice treated with h6E7N54A (6E7.L4H1eA54)x38E4v1 TDB.
Figure 19B:
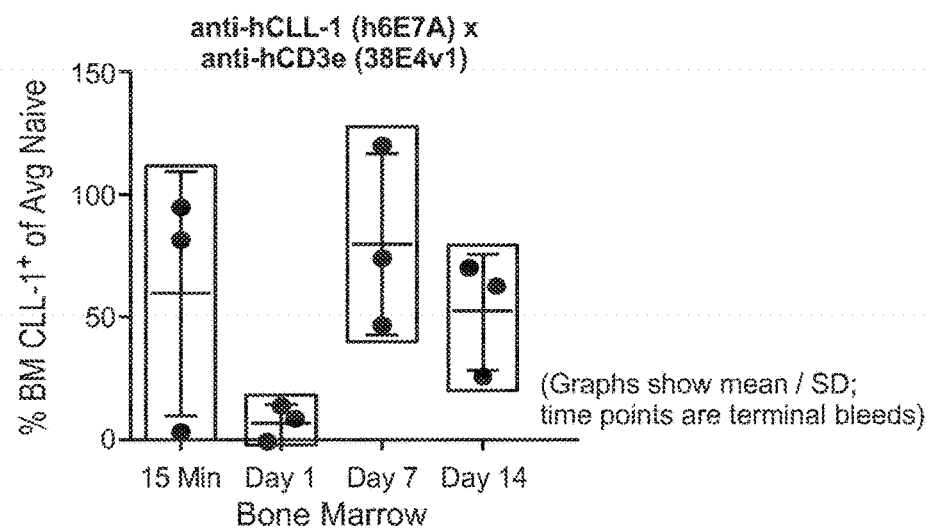
Figure 19C:
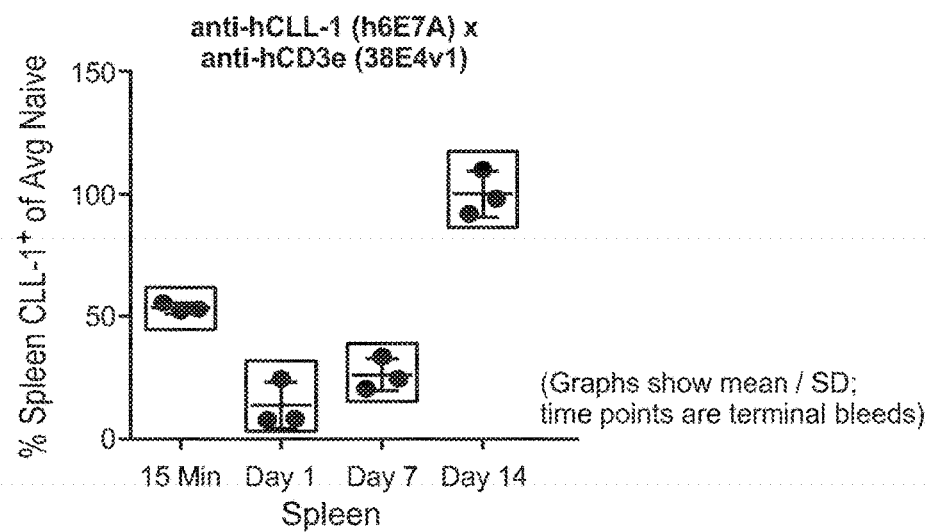
Figure 20A:
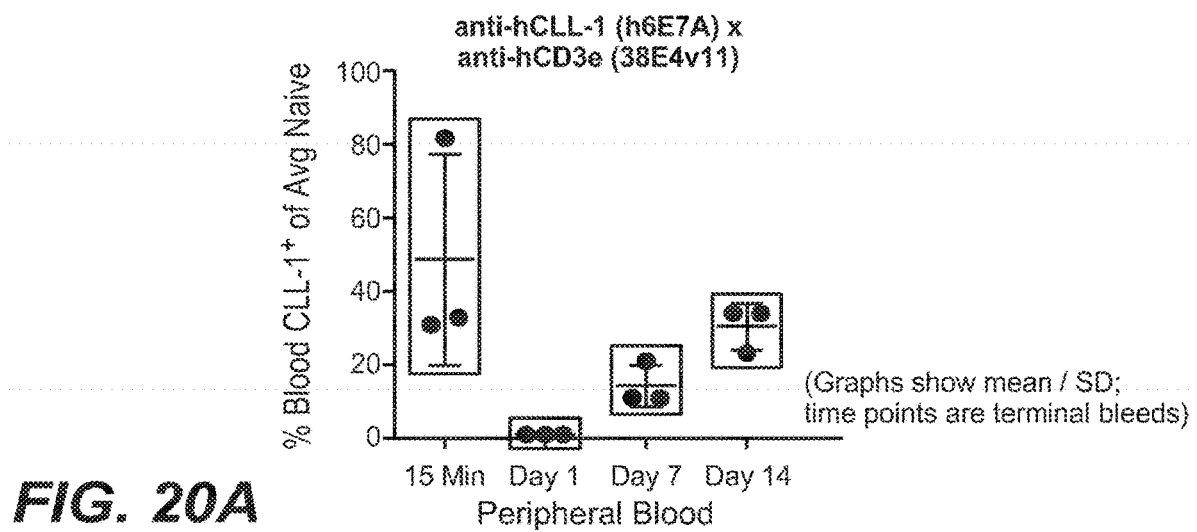
FIG. 20A-C shows PD data in peripheral blood (A), bone marrow (B), and spleen (C) of hCLL-1/hCD3e BAC-Tg mice treated with h6E7N54A (6E7.L4H1eA54)x38E4v11 TDB.
Figure 20B:
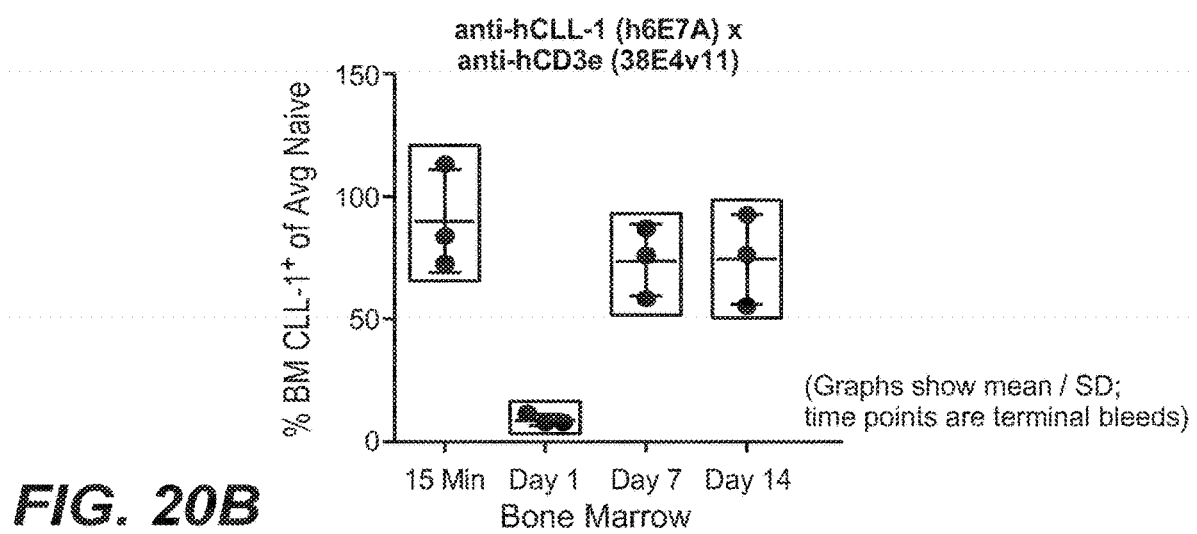
Figure 20C:
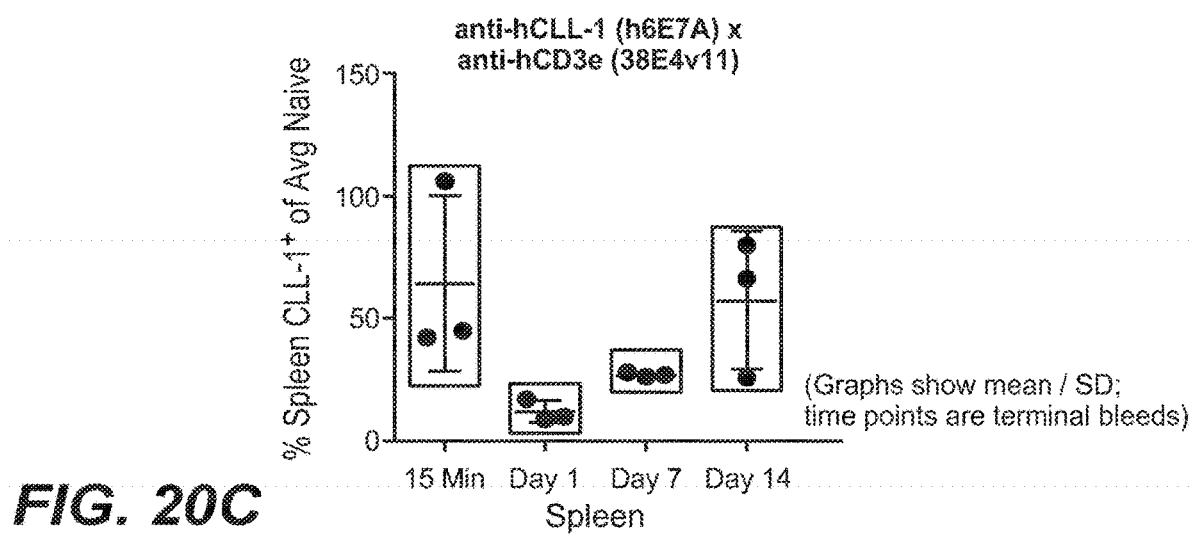
Figure 21A:
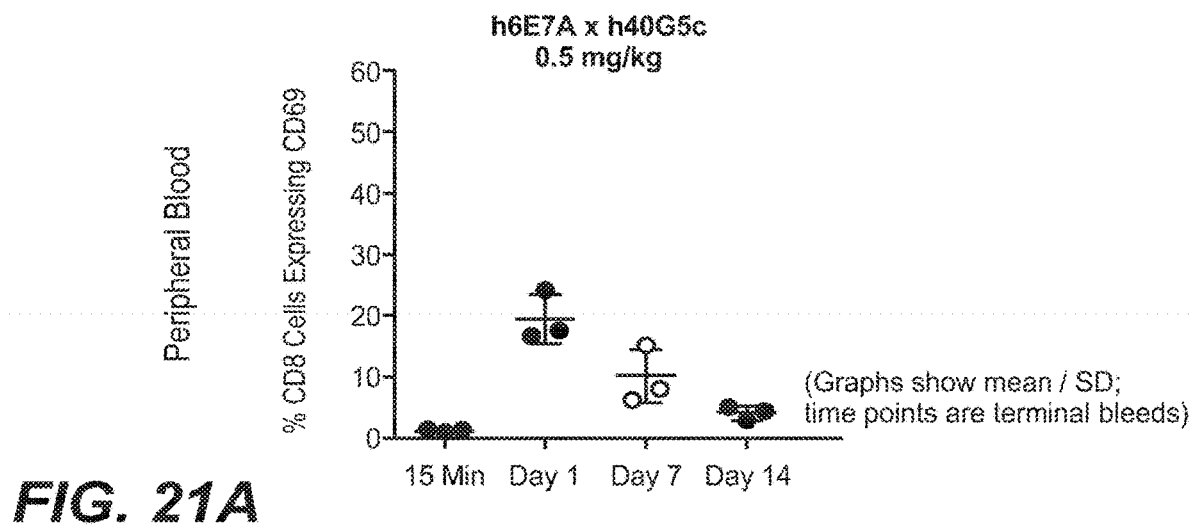
FIG. 21A-F shows upregulation of CD69 on mouse CD8+ cells correlated with the time point associated with maximal target diminution in hCLL-1/hCD3e BAC-Tg mice treated with h6E7A (6E7.L4H1eA54)xh40G5c TDB (A and D), h6E7N54A (6E7.L4H1eA54)x38E4v1 TDB (B and E), and h6E7N54A (6E7.L4H1eA54)x38E4v11 TDB (C and F).
Figure 21B:
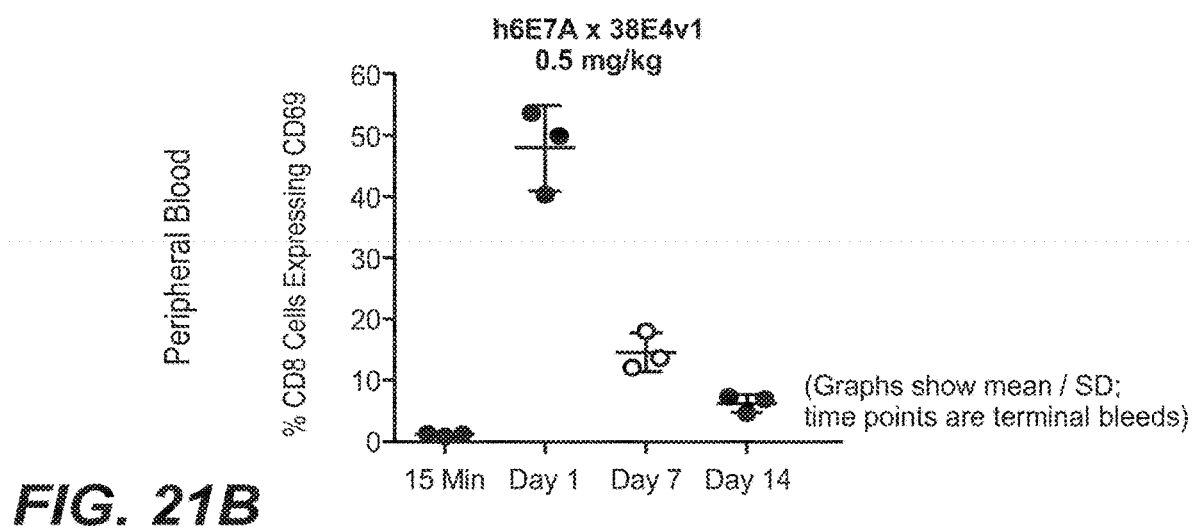
Figure 21C:
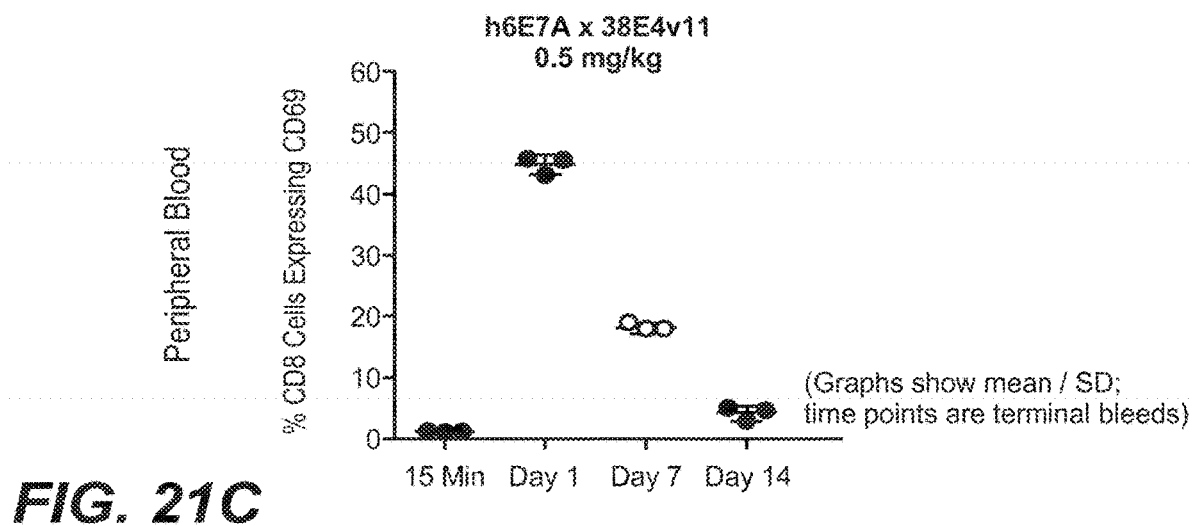
Figure 21D:
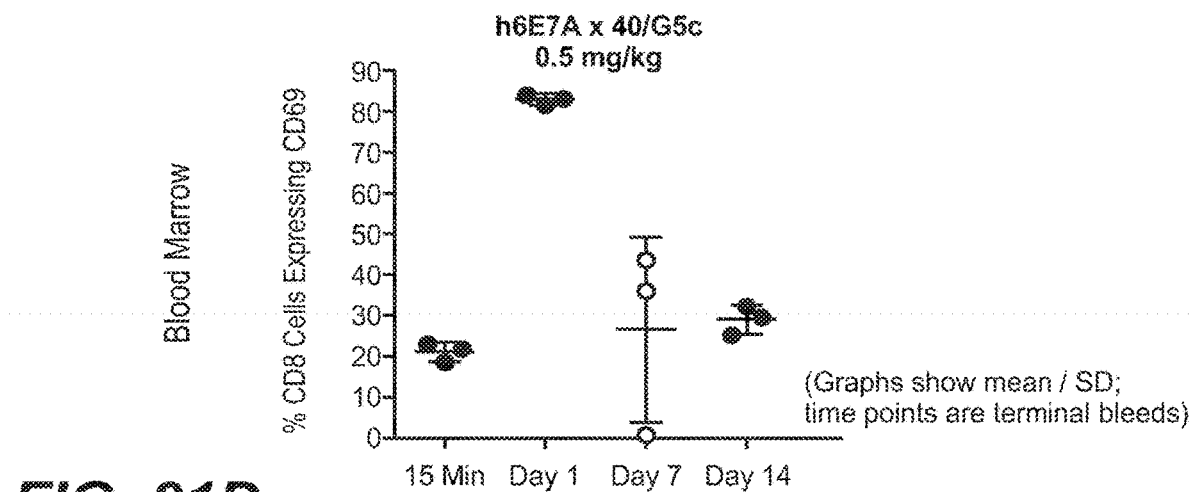
Figure 21E:
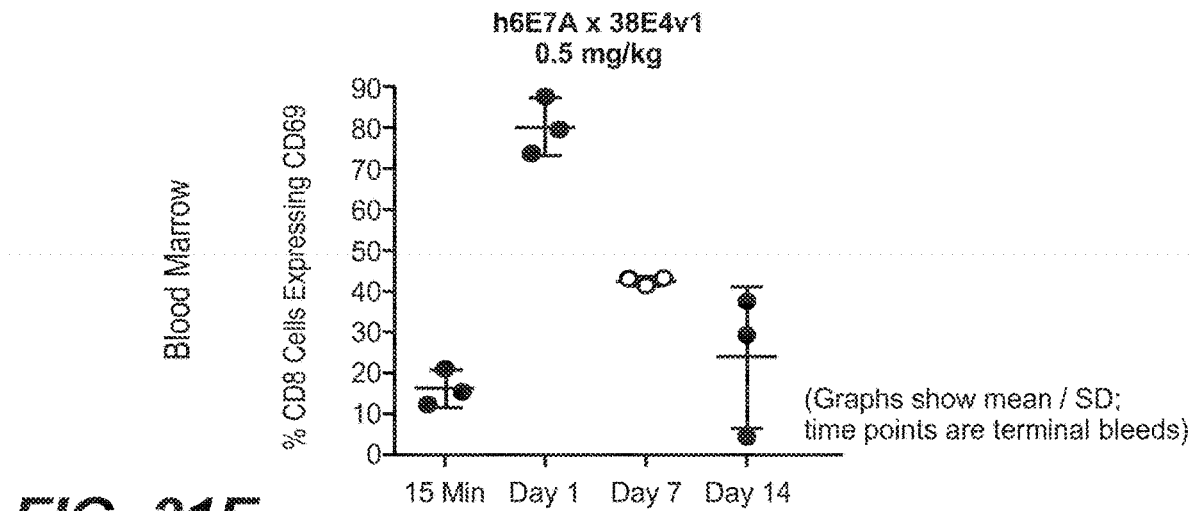
Figure 21F:
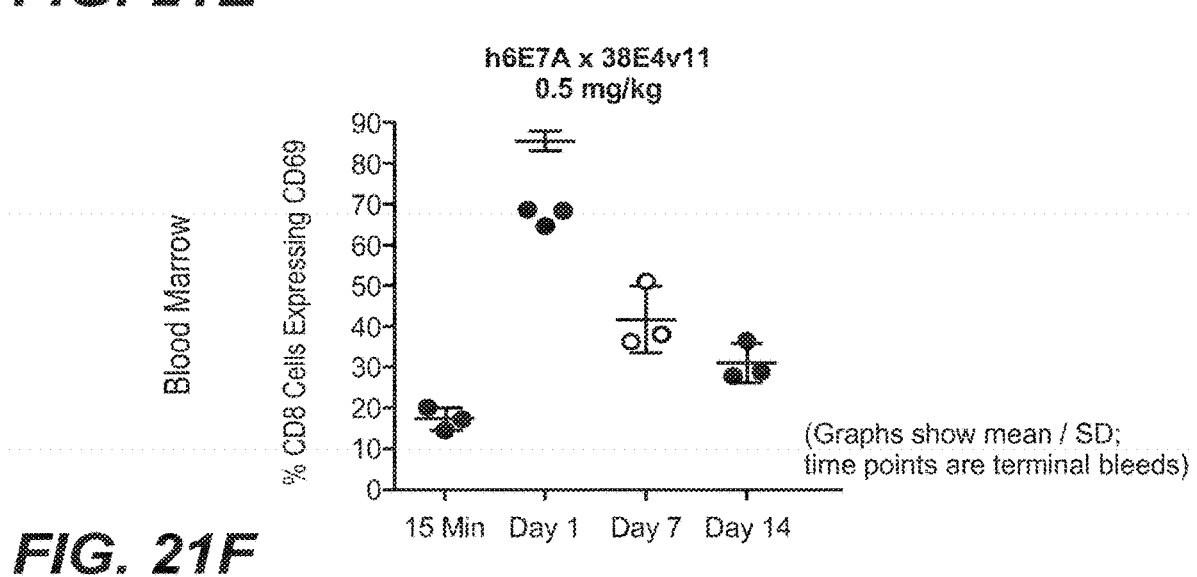

A reduction in mouse cells expressing human CLL-1 was used as a measure of PD in peripheral blood, bone marrow and spleen. FIG. 18 shows that a single 0.5 mg/kg dose of h6E7A (6E7.L4H1eA54)×h40G5c resulted in maximal target reduction around Day 7 in peripheral blood with a concomitant diminution of target cells in bone marrow and spleen. Similar and more profound effects were seen with h6E7N54A (6E7.L4H1eA54)×38E4v1 (FIG. 19) and h6E7N54A (6E7.L4H1eA54)×38E4v11 (FIG. 20). The upregulation of CD69 on mouse CD8+ cells also correlated with the time point associated with maximal target diminution (FIG. 21). The lack of target cells in blood, bone marrow and spleen suggests that the diminution of target cells expressing hCLL-1 was not because of margination to bone marrow or spleen. Similar results were seen in pooled lymph nodes (data not shown).

Figure 22C:
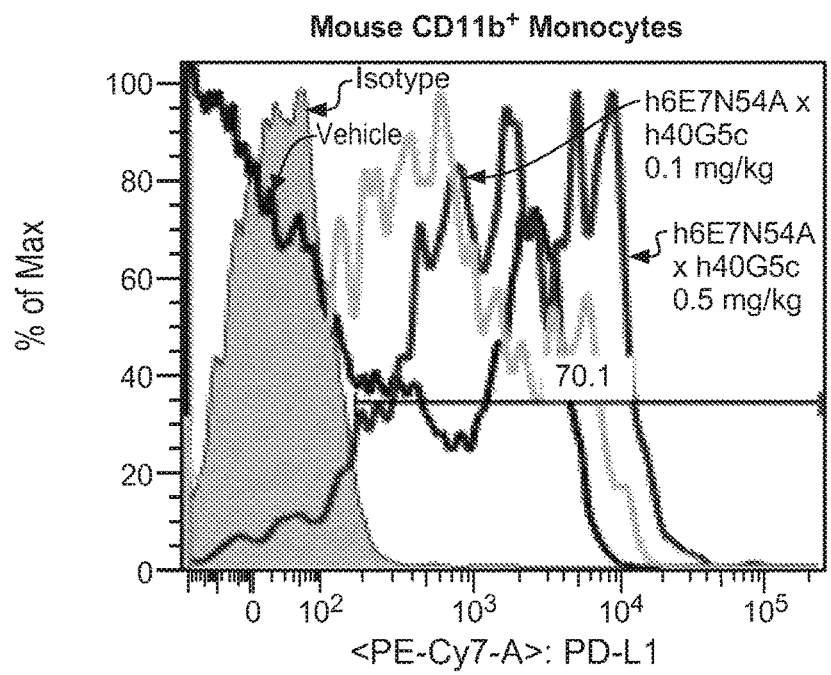
FIG. 22C-D shows upregulation of PD-L1 on monocytes and granulocytes in hCLL-1/hCD3e BAC-Tg mice treated with anti-CLL-1/CD3 TDB antibody.
Figure 22D:
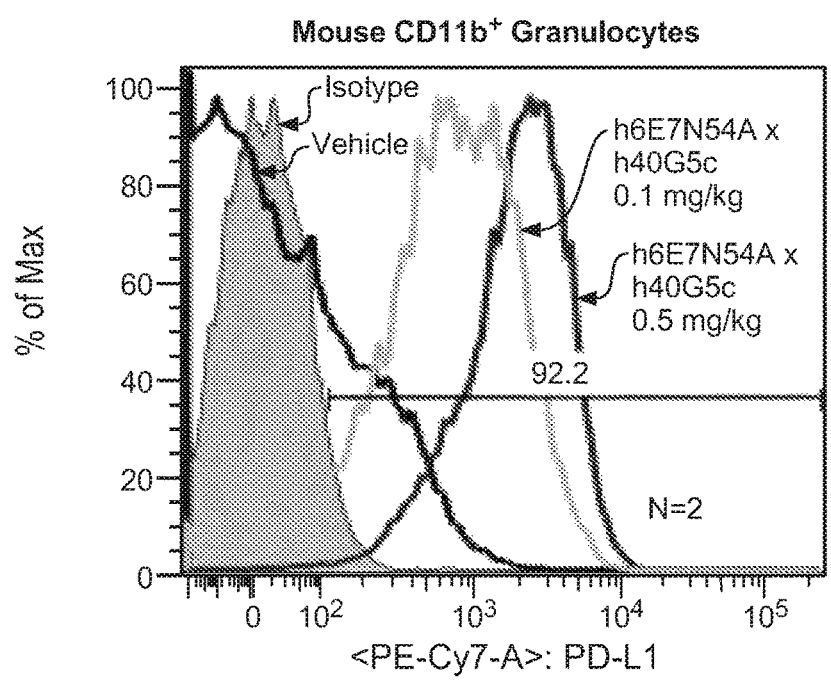

In another experiment, 2×BAC-Tg mice were treated with vehicle or anti-PD-L1 (6E11) or h6E7N54A (6E7.L4H1eA54)×h40G5c at 0.1 mg/kg or h6E7N54A (6E7.L4H1eA54)×h40G5c 0.5 mg/kg or a combination of h6E7N54A (6E7.L4H1eA54)×h40G5c and anti-PD-L1. Administration of anti-PD-L1 was given at 10 mg/kg IV on Day 0, and followed by twice weekly IP dosing at 5 mg/kg. The results of two independent in vivo studies show that combination treatment with h6E7N54A (6E7.L4H1eA54)×h40G5c at 0.5 mg/kg and anti-PD-L1 at 10 mg/kg resulted in better overall myeloid reduction compared to mice treated with either single agent (FIG. 22A-B). However, in this mouse model only monocytes and a sub-population of granulocytes, eosinophils, express detectable levels of human CLL-1 by flow cytometry. It is possible that the majority of granulocytes in the 2×-BAC-Tg model express human CLL-1, but below the limit of detection by flow cytometry. In cynomolgus monkey and humans, there is significant cell surface expression of CLL-1 on monocytes and granulocytes. The improvement in granulocyte reduction in the 2×BAC-Tg model might be explained by that fact that h6E7N54A (6E7.L4H1eA54)×h40G5c may upregulate PD-L1 on myeloid cells. To address this hypothesis, blood from mice treated with either vehicle or h6E7N54A (6E7.L4H1eA54)×h40G5c at 0.1 mg/kg or h6E7N54A (6E7.L4H1eA54)xh40G5c at 0.5 mg/kg were analyzed at Day 7 (study end) for the presence of cell surface PD-L1 on CD11b⁺ myeloid cells. FIG. 22C-D shows that mice treated with single agent, h6E7N54A (6E7.L4H1eA54)xh40G5c, exhibited significant upregulation of PD-L1 expression on granulocytes compared to the negative control group (Vehicle). A similar response was evident on monocytes. Overall, the level of PD-L1 upregulation was associated with the dose of h6E7N54A (6E7.L4H1eA54)xh40G5c. These results demonstrate that h6E7N54A (6E7.L4H1eA54)x h40G5c has the ability to modulate immune checkpoint molecules like PD-L1, and that combining an anti-PD-L1 therapeutic with an anti-CLL-1 directed bispecific antibody like h6E7N54A (6E7.L4H1eA54)xh40G5c or h6E7N54A (6E7.L4H1eA54)xh38E4v1 or h6E7N54A (6E7.L4H1eA54)xh38E4v11 is another therapeutic strategy for AML.

Example 3: Toxicity, Toxicokinetic (TK), and PD Study in Cynomolgus Monkeys

Anti-CLL-1/CD3 TDB antibodies described above (h6E7A (6E7.L4H1eA54)xh40G5c (low affinity anti-human CD3ε arm) and h6E7A (6E7.L4H1eA54)xh38E4v1 (high affinity anti-human CD3ε arm)) were assessed in cynomolgus monkeys to determine toxicity, toxicokinetics (TK), and pharmacodynamics (PD). This study was conducted using purpose bred, naïve, *Macaca fascicularis* of Mauritius origin. Animals selected for the study were demonstrated to express CLL-1 on circulating CD11b+ myeloid cells (granulocytes and monocytes) by flow cytometry. Four groups of male cynomolgus monkeys were administered vehicle or anti-CLL-1/CD3 TDB antibody via a single intravenous infusion and studied for 8-29 days for target cell depletion and recovery, as summarized in Table 9.

TABLE 9

Study design of single dose toxicity, TK, and PD study in cynomolgus monkeys

| Group | Test article | Affinity (CLL-1/CD3) | Regimen | Dose (mg/kg) | N | Scheduled necropsy (day post dose) |
|---|---|---|---|---|---|---|
| 1 | vehicle | — | Single | 0 | 3 | 29 |
| 2 | h6E7A × h40G5c | H/L | dose, | 0.5 | 3 | 29 |
| 3 | h6E7A × h40G5c | H/L | 1 hr. IV | 0.2 | 3/3 | 8/22 |
| 4 | h6E7A × h38E4v1 | H/H | infusion | 0.5 | 3 | 29 |

Serum was collected at multiple time points and stored at −70C for ELISA to determine the amount of test article in each serum sample. Serum concentration-time profiles were used to estimate PK parameters using WinNonlin software (Pharsight; Mountain View, Calif.). PD effects were determined by standard hematological assessments (differential leukocyte counts) and by measuring the reduction in CD11b⁺ myeloid cells in the peripheral blood and bone marrow by flow cytometry. Bone marrow flow cytometry was conducted as follows: fresh bone marrow aspirates were processed by gradient centrifugation using 90% Hypaque-Ficoll to remove contaminating red blood cells. Subsequently, purified bone marrow cells were stained with antibodies specific to non-human primate CD4 (Pe-Cy7), CD8 (Pacific Blue), C20 (FITC), CD11b (APC) and CLL-1 (PE) in the presence of the viability dye, 7AAD, using the live cell staining conditions described above. Serum cytokine levels were analyzed with a multiplex assay and serum biochemistry was assessed using standard assays.

Four animals were euthanized prior to their scheduled necropsy (all three animals in Group 4 and one in Group 2). All three animals in Group 4 given the anti-CLL-1/CD3 TDB antibody with the high affinity CD3 arm (h6E7A (6E7.L4H1eA54)xh38E4v1) (0.5 mg/kg) displayed fever and moribund condition that correlated with markedly elevated serum cytokine levels (including TNF-α, IFN-γ, IL-2, IL-4, IL-5, and IL-6). These animals were euthanized on Day 1 (N=1) or 2 (N=2) and had microscopic evidence of circulatory collapse consistent with cytokine release syndrome. Due to this toxicity, the anti-CLL-1/CD3 TDB antibody with the high affinity CD3 arm (h6E7A (6E7.L4H1eA54)xh38E4v1) was not evaluated further.

Animals in Group 2 displayed fever between 4-8 days post dose. One of these animals developed poor appetite and malaise requiring early euthanasia on day 6. A specific cause for the morbidity of this animal was not identified and a lower dose of 0.2 mg/kg anti-CLL-1/CD3 TDB antibody with the low affinity CD3 arm (h6E7A (6E7.L4H1eA54)x h40G5c) was investigated in Group 3. This dose was well tolerated in all animals, with no fever or other clinical signs for the duration of the study. A reduced cytokine response was observed in animals administered the anti-CLL-1/CD3 TDB antibody with the low affinity CD3 arm (h6E7A (6E7.L4H1eA54)xh40G5c), with little elevation in most of the proinflammatory cytokines evaluated compared to those animals administered the anti-CLL-1/CD3 TDB antibody with the high affinity CD3 arm (h6E7A (6E7.L4H1eA54)x h38E4v1). All Group 3 animals survived to the scheduled necropsies on Day 8 (N=3) and Day 22 (N=3).

In general, clinical pathology changes for anti-CLL-1/CD3 TDB antibodies with low and high affinity CD3 arms were similar and consistent with target-related marked decreases in myeloid and lymphoid cells, cytokine release, and an associated acute phase inflammatory response. The Group 4 animals and the animal requiring an unscheduled necropsy in Group 2 had a similar magnitude of hematology (PD) effects but generally more pronounced acute phase response compared to monkeys given 0.2 mg/kg of the anti-CLL-1/CD3 TDB antibody with the low affinity CD3 arm (h6E7A (6E7.L4H1eA54)xh40G5c) that survived to scheduled necropsies.

Figure 23A:
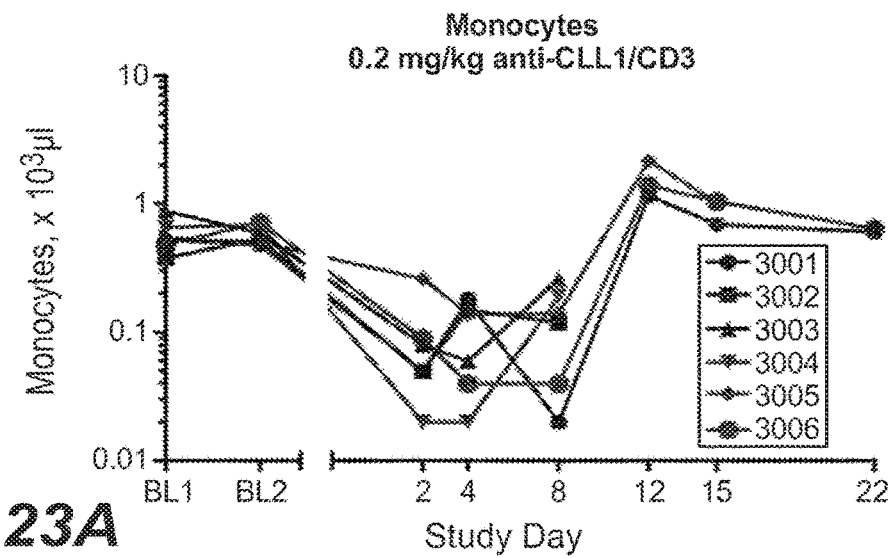
FIG. 23A-D shows myeloid cell numbers or CLL-1-positive cell numbers in cynomolgus monkeys treated with the low affinity anti-CLL-1/CD3 TDB antibody ((6E7.L4H1eA54)xh40G5c).
Figure 23B:
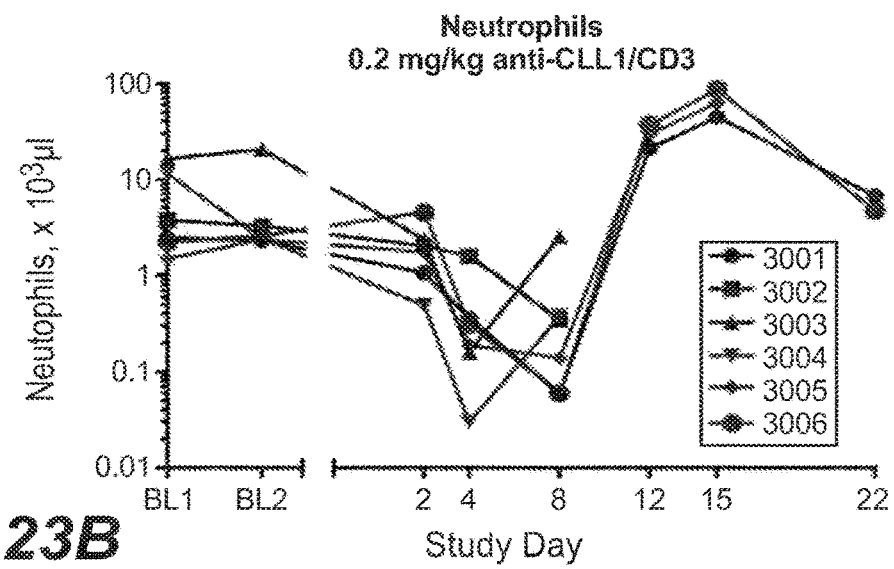
Figure 24:
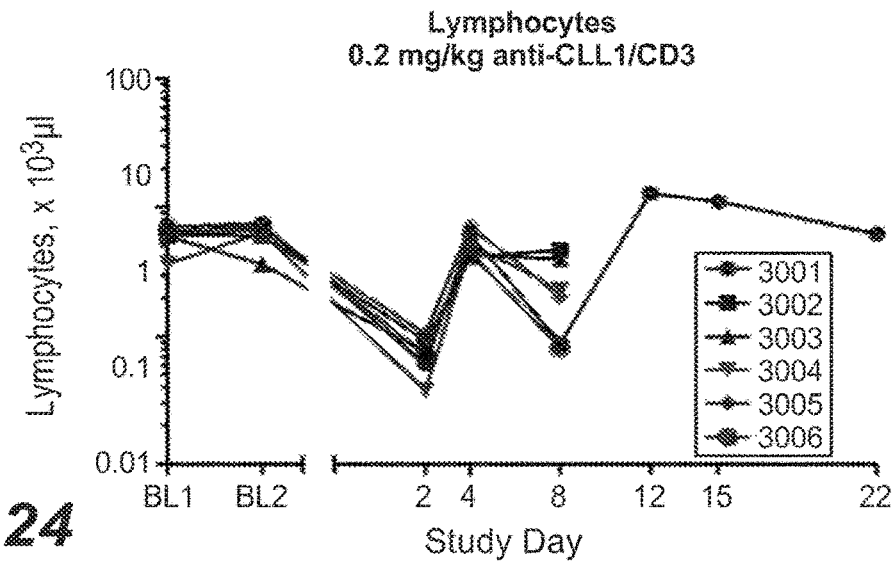
FIG. 24 shows circulating lymphocyte numbers in cynomolgus monkeys treated with the low affinity anti-CLL-1/CD3 TDB antibody ((6E7.L4H1eA54)xh40G5c).
Figure 23C:
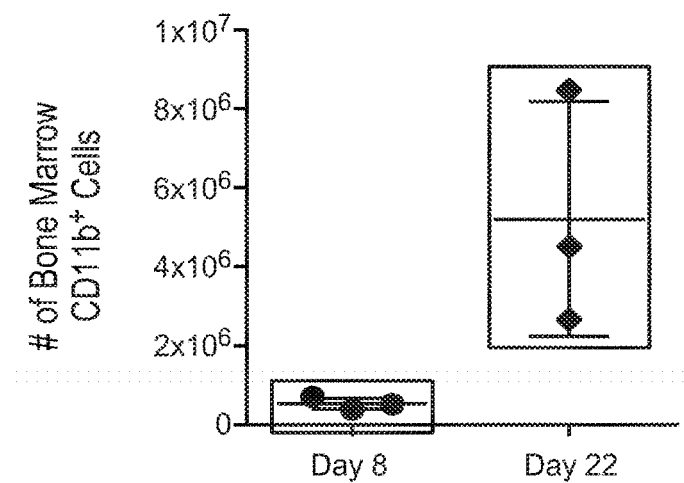
Figure 23D:
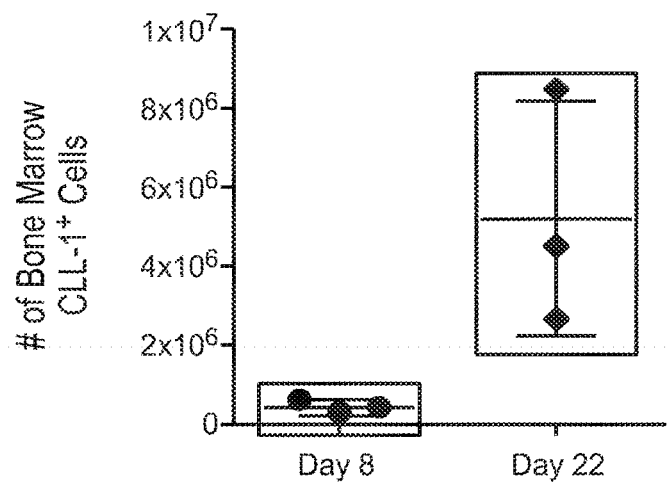

Animals receiving the anti-CLL-1/CD3 TDB antibody (6E7.L4H1eA54)xh40G5c) with the low affinity CD3 arm displayed the expected myeloid cell reduction due to pharmacological activity of the bispecific antibody. There were marked reductions of monocytes and neutrophils predominantly on Day 2-4 and 4-8, respectively (FIGS. 23A and B), that correlated with markedly decreased late stage myeloid cells in the bone marrow and neutrophils in the spleen at day 6 (unscheduled) and day 8 necropsies. Flow cytometry assessment of bone marrow from animals euthanized on day 8 confirmed a significant reduction in total CD11b⁺ myeloid cells (FIG. 23C). In addition, all of the CD11b⁺ cells co-expressed cynomolgus CLL-1 (see FIG. 23D), thus demonstrating target specificity, with a concomitant depletion of both blood and the bone marrow myeloid cells. Circulating lymphocytes were reduced beginning on Day 2 (FIG. 24). There was rebound recovery for neutrophils, monocytes, and lymphocytes by Day 12, with markedly increased neutrophils at 0.2 mg/kg on Day 15 that were considered to be a continuation of the rebound response and correlated with increases in G-CSF that occurred by Day 8. All leukocyte counts for individual animals trended toward or approximated baseline by Day 22 or Day 29 and there was complete recovery of microscopic changes in the spleen and bone marrow by Day 22 and Day 29, respectively.

The reduction in clinical signs, morbidity, and diminished cytokine release compared to the high affinity version indicates the improved safety profile of the anti-CLL-1/CD3 TDB antibody with the low affinity CD3 arm (h6E7A (6E7.L4H1eA54)×h40G5c) compared to the anti-CLL-1/CD3 TDB antibody with the high affinity CD3 arm (h6E7A (6E7.L4H1eA54)×h38E4v1).

Figure 25:
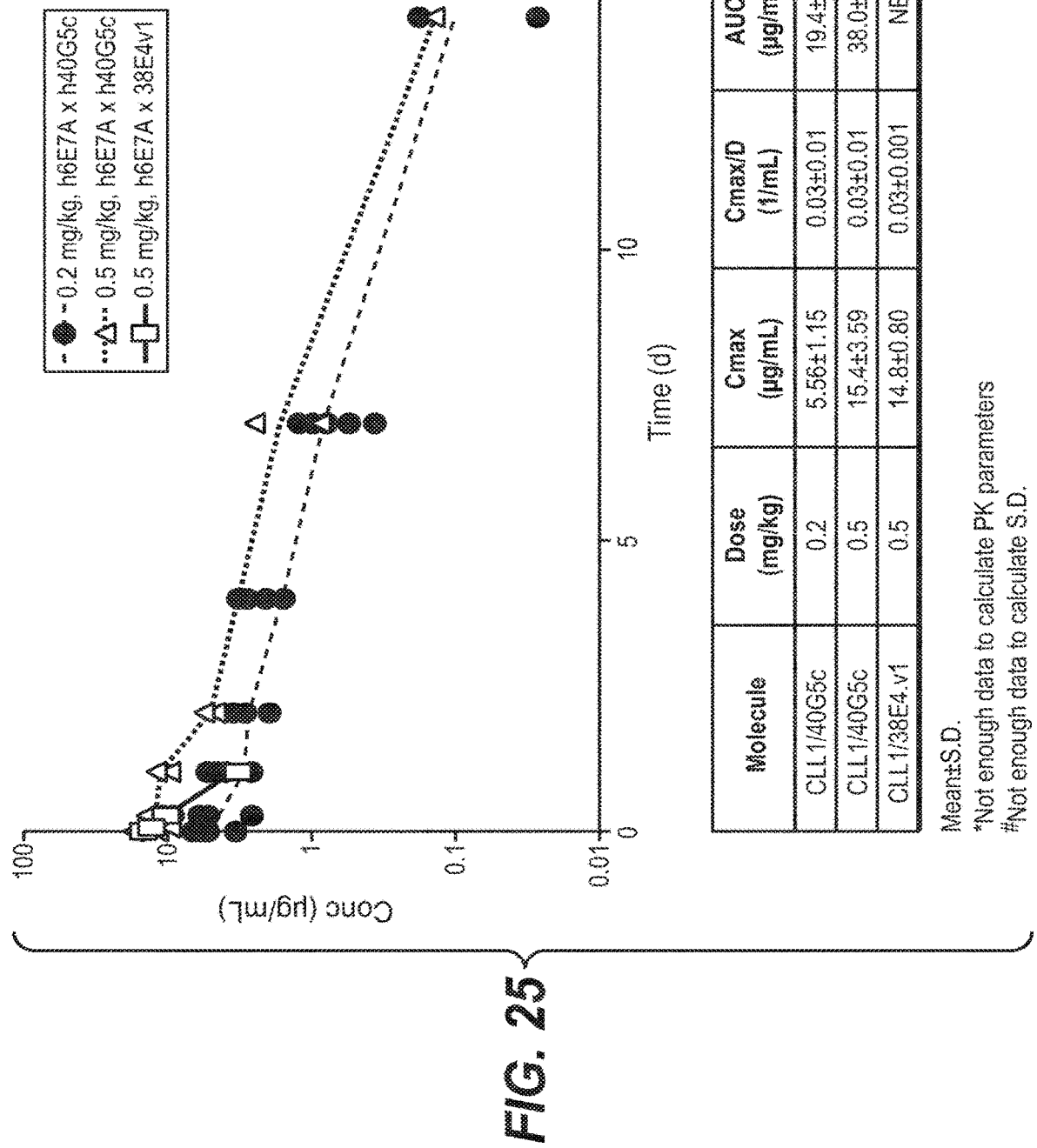
FIG. 25 shows PK parameters in cynomolgus monkeys treated with anti-CLL-1/CD3 TDB antibodies.

Drug exposure was confirmed in all animals in the treatment groups. The concentration-time profile and PK parameter summary are shown in FIG. 25. Dose proportional Cmax was observed for the h6E7A×h40G5c TDB antibody ((6E7.L4H1eA54)×h40G5c) between 0.2 and 0.5 mg/kg. Positive anti-therapeutic antibodies ("ATA") were confirmed in all samples on day 15. Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| NAME | SEQUENCE | SEQ ID NO |
|---|---|---|
| Human CLL-1 (UniProt No. Q5QGZ9; NCBI Ref. NP_612210.4) | MSEEVTYADL QFQNSSEMEK IPEIGKFGEK APPAPSHVWR PAALFLTLLC LLLLIGLGVL ASMFHVTLKI EMKKMNKLQN ISEELQRNIS LQLMSNMNIS NKIRNLSTTL QTIATKLCRE LYSKEQEHKC KPCPRRWIWH KDSCYFLSDD VQTWQESKMA CAAQNASLLK INNKNALEFI KSQSRSYDYW LGLSPEEDST RGMRVDNIIN SSAWVIRNAP DLNNMYCGYI NRLYVQYYHC TYKKRMICEK MANPVQLGST YFREA | 1 |
| Human CLL-1 ECD (aa 65-265 of SEQ ID NO: 1) | HVTLKIEMKKMNKLQNISEELQRNISLQLMSNMNISNKIRNLSTTLQTIA TKLCRELYSKEQEHKCKPCPRRWIWHKDSCYFLSDDVQTWQESKMACAAQ NASLLKINNKNALEFIKSQSRSYDYWLGLSPEEDSTRGMRVDNIINSSAW VIRNAPDLNNMYCGYINRLYVQYYHCTYKKRMICEKMANPVQLGSTYFRE A | 2 |
| Human CLL-1 C-type lectin-like domain (CTLD) (aa 133-250 of SEQ ID NO: 1 | CPRRWIWHKDSCYFLSDDVQTWQESKMACAAQNASLLKINNKNALEFIKS QSRSYDYWLGLSPEEDSTRGMRVDNIINSSAWVIRNAPDLNNMYCGYINR LYVQYYHCTYKKRMICEK | 3 |
| Cyno CLL-1 | MSEEVTYADLKFQNSSETEKIQEIAKFGGKAPPAPSCVWRPAALFLTVLC LLMLIGLGVLGSMFHITLKTAMKKMNKLQNINEELQRNVSLQLMSNMNSS NKIRNLSTTLQTIATRLCRELYSKEQEHKCKPCPRRWIWHKDSCYFLSDD VRTWQESRMACAAQNASLLKINNKNALEFIKSQSTSYPYWLGLSPEKDYS YGTSVDDIINSSAWVTRNASDLNNMFCGYINRIYVHYDYCIYRKKMICEK MANPVQLGFIHFREA | 4 |
| m6E7-HVR L1<br>6E7L4H1e-HVR L1<br>6E7L4H1eA54-HVR L1 | RASQSVSTSSYNYMH | 5 |
| m6E7-HVR L2<br>6E7L4H1e-HVR L2<br>6E7L4H1eA54-HVR L2 | YASNLES | 6 |
| m6E7-HVR L3<br>6E7L4H1e-HVR L3<br>6E7L4H1eA54-HVR L3 | QHSWEIPLT | 7 |
| m6E7-HVR H1<br>6E7L4H1e-HVR H1<br>6E7L4H1eA54-HVR H1 | DYYMH | 8 |
| m6E7-HVR H2<br>6E7L4H1e-HVR H2 | RINPYNGAAFYSQNFKD | 9 |
| m6E7-HVR H3<br>6E7L4H1e-HVR H3<br>6E7L4H1eA54-HVR H3 | ERGADLEGYAMDY | 10 |
| 6E7L4H1eA54-HVR H2 | RINPYAGAAFYSQNFKD | 11 |
| m20B1-HVR L1 | SASSSISYMY | 12 |
| m20B1-HVR L2 | DTSKLAS | 13 |
| m20B1-HVR L3 | HQRSSWT | 14 |
| m20B1-HVR H1 | SYDIN | 15 |
| m20B1-HVR H2 | WIYPGDGTTEYNERFKG | 16 |
| m20B1-HVR H3 | SYDYDYAMDY | 17 |

-continued

| NAME | SEQUENCE | SEQ ID NO |
|---|---|---|
| m21C9-HVR L1<br>21C9.L2H-HVR L1 | KASQDVSTAVA | 18 |
| m21C9-HVR L2<br>21C9.L2H-HVR L2 | SPSYRYT | 19 |
| m21C9-HVR L3<br>21C9.L2H-HVR L3 | QQLYSTPYT | 20 |
| m21C9-HVR H1<br>21C9.L2H-HVR H1 | DYYLD | 21 |
| m21C9-HVR H2<br>21C9.L2H-HVR H2 | RVNPYNGGTIYNQKFKG | 22 |
| m21C9-HVR H3<br>21C9.L2H-HVR H3 | DHYRYDPLLDY | 23 |
| m28H12-HVR L1 | RASQSVSSSSYSYMH | 24 |
| m28H12-HVR L2 | YASNLES | 25 |
| m28H12-HVR L3 | QHSWEIPYT | 26 |
| m28H12-HVR H1 | DTYMH | 27 |
| m28H12-HVR H2 | RIDPANGDTDYDPKFQG | 28 |
| m28H12-HVR H3 | SGPPYYVMDY | 29 |
| m6E7 $V_L$ | DIVLTQSPSSLIVSLGQRATISCRASQSVSTSSYNYMHWYQQKPGQPPKL<br>LLKYASNLESGVPARFSGSGSGTDFTLNIHPVEEEDTATYYCQHSWEIPL<br>TFGAGTKLEIK | 30 |
| m6E7 $V_H$ | QVQLQQSGPELVKPGASVKISCKASGYSFTDYYMHWVKQSHIKSLEWIGR<br>INPYNGAAFYSQNFKDKASLTVDKSSSTAYMELHSLTSEDSAVYYCAIER<br>GADLEGYAMDYWGQGTSVTVSS | 31 |
| 6E7L4H1e $V_L$ | DIQMTQSPSSLSASVGDRVTITCRASQSVSTSSYNYMHWYQQKPGKPPKL<br>LIKYASNLESGVPSRFSGSGSGTDFTLTISSLQPEDFATYYCQHSWEIPL<br>TFGQGTKVEIK | 32 |
| 6E7L4H1e $V_H$ | EVQLVQSGAEVKKPGASVKVSCKASGYSFTDYYMHWVRQAPGQGLEWIGR<br>INPYNGAAFYSQNFKDRVTLTVDTSTSTAYLELSSLRSEDTAVYYCAIER<br>GADLEGYAMDYWGQGTLVTVSS | 33 |
| 6E7L4H1eA54 $V_H$ | EVQLVQSGAEVKKPGASVKVSCKASGYSFTDYYMHWVRQAPGQGLEWIGR<br>INPYAGAAFYSQNFKDRVTLTVDTSTSTAYLELSSLRSEDTAVYYCAIER<br>GADLEGYAMDYWGQGTLVTVSS | 34 |
| m20B1 $V_L$ | DIVLTQSPAIMSASPGEKVTMTCSASSSISYMYWYQQKPGTSPKRWIYDT<br>SKLASGVPARFSGSGSGTSYSLTISSMEAEDAATYYCHQRSSWTFGGGTK<br>LEIK | 35 |
| m20B1 $V_H$ | EVQLQQSGPELVKPGALVKISCKASGYTFTSYDINWLKQRPGQGLEWIGW<br>TYPGDGTTEYNERFKGKATLTADKSSSTAYLQLSSLTSENSAVYFCARSY<br>DYDYAMDYWGQGTSVTVSS | 36 |
| m21C9 $V_L$ | DIQMTQSHKFMSTSVGDRVSITCKASQDVSTAVAWFQQKPGQSPKLLIYS<br>PSYRYTGVPDRFTGSGSGTDFTFTISSVQAEDLAVYYCQQLYSTPYTFGG<br>GTKLEIK | 37 |
| m21C9 $V_H$ | EVQLQQSGPELVKPGASVKMSCKASGYTFTDYYLDWVKQSHGESFEWIGR<br>VNPYNGGTIYNQKFKGKATLTVDKSSSTAYMDLNSLTSEDSAVYYCARDH<br>YRYDPLLDYWGQGTTLTVSS | 38 |
| 21C9.L2H3 $V_L$ | DIQMTQSPSSLSASVGDRVTITCKASQDVSTAVAWFQQKPGKAPKLLIYS<br>PSYRYTGVPSRFSGSGSGTDFTLTISSLQPEDFATYYCQQLYSTPYTFGQ<br>GTKVEIK | 39 |
| 21C9.L2H3 $V_H$ | EVQLVQSGAEVKKPGASVKVSCKASGYTFTDYYLDWVRQAPGQGLEWIGR<br>VNPYNGGTIYNQKFKGRVTLTRDTSTSTAYLELSSLRSEDTAVYYCARDH<br>YRYDPLLDYWGQGTLVTVSS | 40 |

| NAME | SEQUENCE | SEQ ID NO |
|---|---|---|
| m28H12 V_L | DIQMTQSPASLAVSLGQRATISCRASQSVSSSSYSYMHWYQQKPGQPPKL LIKYASNLESGVPARFSGRGSGTDFTLNIHPVEEEDTATYYCQHSWEIPY TFGGGTRLEIK | 41 |
| m28H12 V_H | QVQLQQSGAELVKPGASVKLSCTASGFNIKDTYMHWVKQRPEQGLEWIGR IDPANGDTDYDPKFQGKATVTADTSSNTAYLQLSSLTSEDTAVYYCTISG PPYYVMDYWGQGTSVTVSS | 42 |
| 6E7L4H1eE54-HVR H2 | RINPYEGAAFYSQNFKD | 43 |
| 6E7L4H1eS54-HVR H2 | RINPYSGAAFYSQNFKD | 44 |
| 6E7L4H1eConsensus-HVR H2 | RINPYX$_1$GAAFYSQNFKD, wherein X$_1$ is A, E, S, or N | 45 |
| 6E7L4H1eConsensus-HVR VH | EVQLVQSGAEVKKPGASVKVSCKASGYSFTDYYMHWVRQAPGQGLEWIGR INPYX$_1$GAAFYSQNFKDRVTLTVDTSTSTAYLELSSLRSEDTAVYYCAIE RGADLEGYAMDYWGQGTLVTVSS, wherein X$_1$ is A, E, S or N | 46 |
| 6E7L4H1eConsensus2-HVR H2 | RINPYX$_2$GAAFYSQNFKD, wherein X$_2$ is A, E, or S | 47 |
| 6E7L4H1eConsensus2-HVR VH | EVQLVQSGAEVKKPGASVKVSCKASGYSFTDYYMHWVRQAPGQGLEWIGR INPYX$_2$GAAFYSQNFKDRVTLTVDTSTSTAYLELSSLRSEDTAVYYCAIE RGADLEGYAMDYWGQGTLVTVSS, wherein X$_2$ is A, E, or S | 48 |
| 40G5c HVR-H1 | NYYIH | 71 |
| 40G5c HVR-H2 | WIYPGDGNTKYNEKFKG | 72 |
| 40G5c HVR-H3 | DSYSNYYFDY | 73 |
| 40G5c HVR-L1 38E4v1 HVR-L1 38E4v11 HVR-L1 CD3 consensus HVR-L1 | KSSQSLLNSRTRKNYLA | 74 |
| 40G5c HVR-L2 | WASTRES | 75 |
| 40G5c HVR-L3 38E4v11 HVR-L3 | TQSFILRT | 76 |
| 38E4v1 HVR-H1 38E4v11 HVR-H1 | SYYIH | 77 |
| 38E4v1 HVR-H2 38E4v11 HVR-H2 | WIYPENDNTKYNEKFKD | 78 |
| 38E4v1 HVR-H3 38E4v11 HVR-H3 | DGYSRYYFDY | 79 |
| 38E4v1 HVR-L2 38E4v11 HVR-L2 | WTSTRKS | 80 |
| 38E4v1 HVR-L3 | KQSFILRT | 81 |
| 40G5c V_H | EVQLVQSGAEVKKPGASVKVSCKASGYTFTNYYIHWVRQAPGQ GLEWIGWIYPGDGNTKYNEKFKGRATLTADTSTSTAYLELSSL RSEDTAVYYCARDSYSNYYFDYWGQGTLVTVSS | 82 |
| 40G5c V_L | DIVMTQSPDSLAVSLGERATINCKSSQSLLNSRTRKNYLAWYQ QKPGQPPKLLIYWASTRESGVPDRFSGSGSGTDFTLTISSLQA EDVAVYYCTQSFILRTFGQGTKVEIK | 83 |
| 38E4v1 V_H 38E4v11 V_H | EVQLVQSGAEVKKPGASVKVSCKASGFTFTSYYIHWVRQAPGQ GLEWIGWIYPENDNTKYNEKFKDRVTITADTSTSTAYLELSSL RSEDTAVYYCARDGYSRYYFDYWGQGTLVTVSS | 84 |
| 38E4v1 V_L | DIVMTQSPDSLAVSLGERATINCKSSQSLLNSRTRKNYLAWYQ QKPGQSPKLLIYWTSTRKSGVPDRFSGSGSGTDFTLTISSLQA EDVAVYYCKQSFILRTFGQGTKVEIK | 85 |

| NAME | SEQUENCE | SEQ ID NO |
|---|---|---|
| 1-26 CD3ε | QDGNEEMGGITQTPYKVSISGTTVILT | 86 |
| 1-27 CD3ε | QDGNEEMGGITQTPYKVSISGTTVILTC | 87 |
| CD3 consensus HVR-H1 | $X_3$YYIH, wherein $X_3$ is N or S | 88 |
| CD3 consensus HVR-H2 | WIYP$X_4$$X_5$$X_6$NTKYNEKFK$X_7$, wherein $X_4$ is G or E, $X_5$ is D or N, $X_6$ is D or G, and $X_7$ is D or G | 89 |
| CD3 consensus HVR-H3 | D$X_8$YS$X_9$YYFDY, wherein $X_8$ is S or G, and $X_9$ is N or R | 90 |
| CD3 consensus HVR-L2 | W$X_{10}$STR$X_{11}$S, wherein $X_{10}$ is A or T, and $X_{11}$ is E or K | 91 |
| CD3 consensus HVR-L3 | $X_{12}$QSFILRT, wherein $X_{12}$ is K or T, | 92 |
| 38E4v11 $V_L$ | DIVMTQSPDSLAVSLGERATINCKSSQSLLNSRTRKNYLAWYQQKPGQSPKLLIYWTSTRKSGVPDRFSGSGSGTDFTLTISSLQAEDVAVYYCTQSFILRTFGQGTKVEIK | 93 |
| PD-L1 $V_H$ | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS | 94 |
| PD-L1 $V_L$ | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKR | 95 |
| PD-L1 HVR-H1 | GFTFS$X_1$SWIH, wherein $X_1$ is D or G | 96 |
| PD-L1 HVR-H2 | AWI$X_2$PYGGS$X_3$YYADSVKG, wherein $X_2$ is S or L; $X_3$ is T or S | 97 |
| PD-L1 HVR-H3 | RHWPGGFDY | 98 |
| PD-L1 HVR-H1 | GFTFSDSWIH | 99 |
| PD-L1 HVR-H2 | AWISPYGGSTYYADSVKG | 100 |
| PD-L1 HVR-L1 | RASQ$X_4$$X_5$$X_6$T$X_7$$X_8$A, wherein $X_4$ is D or V; $X_5$ is V or I; $X_6$ is S or N; $X_7$ is A or F; $X_8$ is V or L | 101 |
| PD-L1 HVR-L2 | SAS$X_9$L$X_{10}$S, wherein $X_9$ is F or T; $X_{10}$ is Y or A | 102 |
| PD-L1 HVR-L3 | QQ$X_{11}$$X_{12}$$X_{13}$$X_{14}$P$X_{15}$T, wherein $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T | 103 |
| PD-L1 HVR-L1 | RASQDVSTAVA | 104 |
| PD-L1 HVR-L2 | SASFLYS | 105 |
| PD-L1 HVR-L3 | QQYLYHPAT | 106 |

What is claimed is:

1. A method of treating or delaying the progression of a cell proliferative disorder in a subject in need thereof, the method comprising administering to the subject an anti-CLL-1 antibody, wherein the antibody comprises:
   (a) a CLL-1 binding domain, wherein the CLL-1 binding domain comprises six hypervariable regions (HVRs) as follows:
      (i) an HVR-L1 comprising the amino acid sequence of SEQ ID NO: 5, an HVR-L2 comprising the amino acid sequence of SEQ ID NO: 6, an HVR-L3 comprising the amino acid sequence of SEQ ID NO: 7, an HVR-H1 comprising the amino acid sequence of SEQ ID NO: 8, an HVR-H2 comprising the amino acid sequence of SEQ ID NO: 45 and an HVR-H3 comprising the amino acid sequence of SEQ ID NO: 10; or
      (ii) an HVR-L1 comprising the amino acid sequence of SEQ ID NO: 12, an HVR-L2 comprising the amino acid sequence of SEQ ID NO: 13, an HVR-L3 comprising the amino acid sequence of SEQ ID NO: 14, an HVR-H1 comprising the amino acid sequence of SEQ ID NO: 15, an HVR-H2 comprising the amino acid sequence of SEQ ID NO: 16 and an HVR-H3 comprising the amino acid sequence of SEQ ID NO: 17; or
      (iii) an HVR-L1 comprising the amino acid sequence of SEQ ID NO: 18, an HVR-L2 comprising the amino acid sequence of SEQ ID NO: 19, an HVR-L3 comprising the amino acid sequence of SEQ ID NO: 20, an HVR-H1 comprising the amino acid sequence of SEQ ID NO: 21, an HVR-H2 comprising the amino acid sequence of SEQ ID NO: 22 and an HVR-H3 comprising the amino acid sequence of SEQ ID NO: 23; or
      (iv) an HVR-L1 comprising the amino acid sequence of SEQ ID NO: 24, an HVR-L2 comprising the amino acid sequence of SEQ ID NO: 25, an HVR-L3 comprising the amino acid sequence of SEQ ID NO: 26, an HVR-H1 comprising the amino acid sequence of SEQ ID NO: 27, an HVR-H2 comprising the amino acid sequence of SEQ ID NO: 28 and an HVR-H3 comprising the amino acid sequence of SEQ ID NO: 29; and
   (b) a CD3 binding domain, wherein the CD3 binding domain comprises six HVRs as follows:
      (i) an HVR-L1 comprising the amino acid sequence of SEQ ID NO: 74, an HVR-L2 comprising the amino acid sequence of SEQ ID NO: 75, an HVR-L3 comprising the amino acid sequence of SEQ ID NO: 76, an HVR-H1 comprising the amino acid sequence of SEQ ID NO: 71, an HVR-H2 comprising the amino acid sequence of SEQ ID NO: 72 and an HVR-H3 comprising the amino acid sequence of SEQ ID NO: 73; or
      (ii) an HVR-L1 comprising the amino acid sequence of SEQ ID NO: 74, an HVR-L2 comprising the amino acid sequence of SEQ ID NO: 80, an HVR-L3 comprising the amino acid sequence of SEQ ID NO: 76, an HVR-H1 comprising the amino acid sequence of SEQ ID NO: 77, an HVR-H2 comprising the amino acid sequence of SEQ ID NO: 78 and an HVR-H3 comprising the amino acid sequence of SEQ ID NO: 79; or
      (iii) an HVR-L1 comprising the amino acid sequence of SEQ ID NO: 74, an HVR-L2 comprising the amino acid sequence of SEQ ID NO: 80, an HVR-L3 comprising the amino acid sequence of SEQ ID NO: 81, an HVR-H1 comprising the amino acid sequence of SEQ ID NO: 77, an HVR-H2 comprising the amino acid sequence of SEQ ID NO: 78 and an HVR-H3 comprising the amino acid sequence of SEQ ID NO: 79.

2. The method of claim 1, wherein the cell proliferative disorder is a cancer.

3. The method of claim 2, wherein the cell proliferative disorder is AML, CML, and/or MDS.

4. The method of claim 1, further comprising administering to the subject daunorubicin and/or cytarabine.

5. The method of claim 1, further comprising administering to the subject a glucocorticoid.

6. The method of claim 5, wherein the glucocorticoid is dexamethasone.

7. The method of claim 1, further comprising administering to the subject a PD-1 axis binding antagonist.

8. The method of claim 7, wherein the PD-1 axis binding antagonist is an anti-PD-L1 antibody.

9. The method of claim 1, wherein the antibody comprises:
   (a) a CLL-1 binding domain, wherein the CLL-1 binding domain comprises:
      (i) a heavy chain variable region comprising the amino acid sequence of SEQ ID NO: 31 and a light chain comprising the amino acid sequence of SEQ ID NO: 30; or
      (ii) a heavy chain variable region comprising the amino acid sequence of SEQ ID NO: 33 and a light chain comprising the amino acid sequence of SEQ ID NO: 32; or
      (iii) a heavy chain variable region comprising the amino acid sequence of SEQ ID NO: 34 and a light chain comprising the amino acid sequence of SEQ ID NO: 32; or
      (iv) a heavy chain variable region comprising the amino acid sequence of SEQ ID NO: 36 and a light chain variable region comprising the amino acid sequence of SEQ ID NO: 35; or
      (v) a heavy chain variable region comprising the amino acid sequence of SEQ ID NO: 38 and the light chain variable region comprising the amino acid sequence of SEQ ID NO: 37; or (vi) a heavy chain variable region comprising the amino acid sequence of SEQ ID NO: 40 and a light chain comprising the amino acid sequence of SEQ ID NO: 39; or
(vii) a heavy chain variable region comprising the amino acid sequence of SEQ ID NO: 42 and the light chain variable region comprising the amino acid sequence of SEQ ID NO: 41; or
(viii) a heavy chain variable region comprising the amino acid sequence of SEQ ID NO: 46 and a light chain comprising the amino acid sequence of SEQ ID NO: 32;
and
(b) a CD3 binding domain comprising:
(i) a heavy chain variable region comprising the amino acid sequence of SEQ ID NO: 82 and the light chain variable region comprising the amino acid sequence of SEQ ID NO: 83; or
(ii) a heavy chain variable region comprising the amino acid sequence of SEQ ID NO: 84 and the light chain variable region comprising the amino acid sequence of SEQ ID NO: 93; or
(iii) a heavy chain variable region comprising the amino acid sequence of SEQ ID NO: 84 and the light chain variable region comprising the amino acid sequence of SEQ ID NO: 85.

10. The method of claim 1, wherein the CLL-1 binding domain comprises the following six hypervariable regions (HVRs): (a) an HVR-L1 comprising the amino acid sequence of SEQ ID NO:5; (b) an HVR-L2 comprising the amino acid sequence of SEQ ID NO:6; (c) an HVR-L3 comprising the amino acid sequence of SEQ ID NO:7; (d) an HVR-H1 comprising the amino acid sequence of SEQ ID NO:8; (e) an HVR-H2 comprising the amino acid sequence of SEQ ID NO:45; and (f) an HVR-H3 comprising the amino acid sequence of SEQ ID NO:10.

11. The method of claim 10, wherein the CLL-1 binding domain comprises HVR-H2 comprising the amino acid sequence of SEQ ID NO:11.

12. The method of claim 1, wherein the CD3 binding domain comprises an HVR-H1 comprising the amino acid sequence of SEQ ID NO: 71, an HVR-H2 comprising the amino acid sequence of SEQ ID NO: 72, an HVR-H3 comprising the amino acid sequence of SEQ ID NO: 73, an HVR-L1 comprising the amino acid sequence of SEQ ID NO: 74, an HVR-L2 comprising the amino acid sequence of SEQ ID NO: 75, and an HVR-L3 comprising the amino acid sequence of SEQ ID NO: 76.

13. A method of enhancing immune function in a subject having a cell proliferative disorder, the method comprising administering to the subject an effective amount of an anti-CLL-1 antibody, wherein the antibody comprises:
(a) a CLL-1 binding domain, wherein the CLL-1 binding domain comprises six hypervariable regions (HVRs) as follows:
(i) an HVR-L1 comprising the amino acid sequence of SEQ ID NO: 5, an HVR-L2 comprising the amino acid sequence of SEQ ID NO: 6, an HVR-L3 comprising the amino acid sequence of SEQ ID NO: 7, an HVR-H1 comprising the amino acid sequence of SEQ ID NO: 8, an HVR-H2 comprising the amino acid sequence of SEQ ID NO: 45 and an HVR-H3 comprising the amino acid sequence of SEQ ID NO: 10; or
(ii) an HVR-L1 comprising the amino acid sequence of SEQ ID NO: 12, an HVR-L2 comprising the amino acid sequence of SEQ ID NO: 13, an HVR-L3 comprising the amino acid sequence of SEQ ID NO: 14, an HVR-H1 comprising the amino acid sequence of SEQ ID NO: 15, an HVR-H2 comprising the amino acid sequence of SEQ ID NO: 16 and an HVR-H3 comprising the amino acid sequence of SEQ ID NO: 17; or
(iii) an HVR-L1 comprising the amino acid sequence of SEQ ID NO: 18, an HVR-L2 comprising the amino acid sequence of SEQ ID NO: 19, an HVR-L3 comprising the amino acid sequence of SEQ ID NO: 20, an HVR-H1 comprising the amino acid sequence of SEQ ID NO: 21, an HVR-H2 comprising the amino acid sequence of SEQ ID NO: 22 and an HVR-H3 comprising the amino acid sequence of SEQ ID NO: 23; or
(iv) an HVR-L1 comprising the amino acid sequence of SEQ ID NO: 24, an HVR-L2 comprising the amino acid sequence of SEQ ID NO: 25, an HVR-L3 comprising the amino acid sequence of SEQ ID NO: 26, an HVR-H1 comprising the amino acid sequence of SEQ ID NO: 27, an HVR-H2 comprising the amino acid sequence of SEQ ID NO: 28 and an HVR-H3 comprising the amino acid sequence of SEQ ID NO: 29; and
(b) a CD3 binding domain, wherein the CD3 binding domain comprises six HVRs as follows:
(i) an HVR-L1 comprising the amino acid sequence of SEQ ID NO: 74, an HVR-L2 comprising the amino acid sequence of SEQ ID NO: 75, an HVR-L3 comprising the amino acid sequence of SEQ ID NO: 76, an HVR-H1 comprising the amino acid sequence of SEQ ID NO: 71, an HVR-H2 comprising the amino acid sequence of SEQ ID NO: 72 and an HVR-H3 comprising the amino acid sequence of SEQ ID NO: 73; or
(ii) an HVR-L1 comprising the amino acid sequence of SEQ ID NO: 74, an HVR-L2 comprising the amino acid sequence of SEQ ID NO: 80, an HVR-L3 comprising the amino acid sequence of SEQ ID NO: 76, an HVR-H1 comprising the amino acid sequence of SEQ ID NO: 77, an HVR-H2 comprising the amino acid sequence of SEQ ID NO: 78 and an HVR-H3 comprising the amino acid sequence of SEQ ID NO: 79; or
(iii) an HVR-L1 comprising the amino acid sequence of SEQ ID NO: 74, an HVR-L2 comprising the amino acid sequence of SEQ ID NO: 80, an HVR-L3 comprising the amino acid sequence of SEQ ID NO: 81, an HVR-H1 comprising the amino acid sequence of SEQ ID NO: 77, an HVR-H2 comprising the amino acid sequence of SEQ ID NO: 78 and an HVR-H3 comprising the amino acid sequence of SEQ ID NO: 79.

14. The method of claim 13, wherein the antibody comprises:
(a) a CLL-1 binding domain comprising:
(i) a heavy chain variable region comprising the amino acid sequence of SEQ ID NO: 31 and a light chain comprising the amino acid sequence of SEQ ID NO: 30; or
(ii) a heavy chain variable region comprising the amino acid sequence of SEQ ID NO: 33 and a light chain comprising the amino acid sequence of SEQ ID NO: 32; or (iii) a heavy chain variable region comprising the amino acid sequence of SEQ ID NO: 34 and a light chain comprising the amino acid sequence of SEQ ID NO: 32; or
(iv) a heavy chain variable region comprising the amino acid sequence of SEQ ID NO: 36 and a light chain variable region comprising the amino acid sequence of SEQ ID NO: 35; or
(v) a heavy chain variable region comprising the amino acid sequence of SEQ ID NO: 38 and the light chain variable region comprising the amino acid sequence of SEQ ID NO: 37; or
(vi) a heavy chain variable region comprising the amino acid sequence of SEQ ID NO: 40 and a light chain comprising the amino acid sequence of SEQ ID NO: 39; or
(vii) a heavy chain variable region comprising the amino acid sequence of SEQ ID NO: 42 and the light chain variable region comprising the amino acid sequence of SEQ ID NO: 41; or
(viii) a heavy chain variable region comprising the amino acid sequence of SEQ ID NO: 46 and a light chain comprising the amino acid sequence of SEQ ID NO: 32;
and
(b) a CD3 binding domain comprising:
(i) a heavy chain variable region comprising the amino acid sequence of SEQ ID NO: 82 and the light chain variable region comprising the amino acid sequence of SEQ ID NO: 83; or
(ii) a heavy chain variable region comprising the amino acid sequence of SEQ ID NO: 84 and the light chain variable region comprising the amino acid sequence of SEQ ID NO: 93; or
(iii) a heavy chain variable region comprising the amino acid sequence of SEQ ID NO: 84 and the light chain variable region comprising the amino acid sequence of SEQ ID NO: 85.

15. The method of claim 13, wherein the CLL-1 binding domain comprises the following six hypervariable regions (HVRs): (a) an HVR-L1 comprising the amino acid sequence of SEQ ID NO:5; (b) an HVR-L2 comprising the amino acid sequence of SEQ ID NO:6; (c) an HVR-L3 comprising the amino acid sequence of SEQ ID NO:7; (d) an HVR-H1 comprising the amino acid sequence of SEQ ID NO:8; (e) an HVR-H2 comprising the amino acid sequence of SEQ ID NO:45; (f) an HVR-H3 comprising the amino acid sequence of SEQ ID NO:10.

16. The method of claim 15, wherein the CLL-1 binding domain comprises HVR-H2 comprising the amino acid sequence of SEQ ID NO:11.

17. The method of claim 13, wherein the CD3 binding domain comprises an HVR-H1 comprising the amino acid sequence of SEQ ID NO: 71, an HVR-H2 comprising the amino acid sequence of SEQ ID NO: 72, an HVR-H3 comprising the amino acid sequence of SEQ ID NO: 73, an HVR-L1 comprising the amino acid sequence of SEQ ID NO: 74, an HVR-L2 comprising the amino acid sequence of SEQ ID NO: 75, and an HVR-L3 comprising the amino acid sequence of SEQ ID NO: 76.

\* \* \* \* \*